(12) United States Patent
Barrett et al.

(10) Patent No.: US 7,482,017 B2
(45) Date of Patent: Jan. 27, 2009

(54) FLAVIVIRUS VARIANTS HAVING PHENOTYPIC VARIATION AND IMMUNOGENIC COMPOSITIONS THEREOF

(75) Inventors: Alan D. T. Barrett, Galveston, TX (US); Robert B. Tesh, Galveston, TX (US); C. Todd Davis, Decatur, GA (US); David W. C. Beasley, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 267 days.

(21) Appl. No.: 11/223,729

(22) Filed: Sep. 9, 2005

(65) Prior Publication Data

US 2006/0062806 A1 Mar. 23, 2006

Related U.S. Application Data

(60) Provisional application No. 60/608,344, filed on Sep. 9, 2004.

(51) Int. Cl.
*A61K 39/12* (2006.01)
*C12P 21/06* (2006.01)

(52) U.S. Cl. .................................. 424/218.1; 435/69.1

(58) Field of Classification Search ........................ None
See application file for complete search history.

(56) References Cited

U.S. PATENT DOCUMENTS

| | | |
|---|---|---|
| 6,576,757 B1 | 6/2003 | Punnonen et al. |
| 2003/0148261 A1 | 8/2003 | Fikrig et al. |
| 2003/0180329 A1 | 9/2003 | Monath et al. |
| 2003/0228327 A1 | 12/2003 | Lasher et al. |
| 2004/0037848 A1 | 2/2004 | Audonnet et al. |
| 2004/0052818 A1 | 3/2004 | Heinz et al. |
| 2005/0002968 A1 | 1/2005 | Monath et al. |
| 2005/0031641 A1 | 2/2005 | Loosmore et al. |
| 2005/0053624 A1 | 3/2005 | Arroyo et al. |
| 2005/0163804 A1 | 7/2005 | Chang |
| 2005/0164170 A1 | 7/2005 | Despres et al. |

FOREIGN PATENT DOCUMENTS

| | | |
|---|---|---|
| WO | WO- 01/60847 | 8/2001 |
| WO | WO- 02/072036 | 9/2002 |
| WO | WO- 02/081621 | 10/2002 |
| WO | WO- 03/048184 | 6/2003 |
| WO | WO- 03/061555 | 7/2003 |
| WO | WO- 03/103571 | 12/2003 |
| WO | WO- 2004/045529 | 6/2004 |
| WO | WO- 2005/042014 | 5/2005 |

OTHER PUBLICATIONS

Monath et al. PNAS USA, 2006, 103(17):6694-6699.*
Brinton, "The Molecular Biology of West Nile Virus: A New Invader of the Western Hemisphere," *Annu. Rev. Microbiol.*, 56: 371-402, 2002.
Markoff, "5'- and 3'-Noncoding Regions in Flavivirus RNA," *Advances in Virus Research*, 59: 177-228, 2003.
Tilgner et al., "The flavivirus-conserved penta-nucleotide in the 3' stem-loop of the West Nile virus genome requires a specific sequence and structure for RNA synthesis, but not for viral translation," *Virology*, 331: 375-386, 2005.
Whitehead et al., "A Live, Attenuated Dengue Virus Type 1 Vaccine Candidate with a 30-Nucleotide Deletion in the 3' Untranslated Region Is Highly Attenuated and Immunogenic in Monkeys," *Journal of Virology*, 77(2): 1653-1657, 2003.
Anderson et al., "A phylogenetic approach to following West Nile virus in Connecticut," *PNAS*, 98(23): 12885-12889, 2001.
Arroyo et al., "ChimeriVax-West Nile Virus Live-Attenuated Vaccine: Preclinical Evaluation of Safety, Immunogenicity, and Efficacy," *J. Virology*, 78(22): 12497-12507, 2004.
Bartelma et al., "Expression, Purification, and Characterization of the RNA 5'-Triphosphatase Activity of Dengue Virus Type 2 Nonstructural Protein 3," *Virology*, 299: 122-132, 2002.
Beasley et al., "Limited evolution of West Nile virus has occured during its southwesterly spread in the United States," *Virology*, 309: 190-195, 2003.
Beasley et al., "Molecular determinants of virulence of West Nile virus in North America," *Arch Virol Suppl.*, (18): 35-41, 2004.
Beasley et al., "Mouse neuroinvasive phenotype of West Nile virus strains varies depending upon virus genotype," *Virology*, 296: 17-23, 2002.
Ben-Nathan et al., "The influence of cold or isolation stress on neuroinvasiveness and virulence of an attenuated variant of West Nile virus," *Arch. Virol.*, 109: 1-10, 1989.
Berthet et al., "Extensive nucleotide changes and deletions within the envelope glycoprotein gene of Euro-African West Nile viruses," *J. General Virology*, 78: 2293-2297, 1997.
Blaney Jr., et al., "Temperature sensitive mutations in the genes encoding the NS1, NS2A, NS3, and NS5 nonstructural proteins of dengue virus type 4 restrict replication in the brains of mice," *Arch. Virol.*, 148: 999-1006, 2003.
Blitvich et al., "Serologic evidence of West Nile virus infection in horses, Coahuila State, Mexico," *Emerg. Infect. Dis.*, 9: 853-856, 2003.
Butrapet et al., "Attenuation Markers of a Candidate Dengue Type 2 Vaccine Virus, Strain 16681 (PDK-53), Are Defined by Mutations in the 5' Noncoding Region and Nonstructural Proteins 1 and 3," *J. Virology*, 74(7): 3011-3019, 2000.
Ceccaldi et al., "New insights on the neuropathogenicity of West Nile virus," *FEMS Microbiology Letters*, 233: 1-6, 2004.
CDC, "Provisional surveillance summary of the West Nile virus epidemic-United States, Jan.-Nov. 2002," *MMWR*, 51: 1129-1133, 2002.

(Continued)

*Primary Examiner*—Stacy B Chen
(74) *Attorney, Agent, or Firm*—Fulbright & Jaworski LLP

(57) ABSTRACT

The present invention concerns isolated attenuated flaviviruses, such as West Nile viruses, having modifications that provide phenotypic varation, particularly in comparison to a more virulent reference strains. The invention encompasses the isolated viruses and immunogenic compositions thereof, in addition to methods to produce and utilize same.

18 Claims, 8 Drawing Sheets

OTHER PUBLICATIONS

Chambers et al., "West Nile virus envelope proteins: nucleotide sequence analysis of strains differing in mouse neuroinvasiveness," *J. General Virology*, 79: 2375-2380, 1998.

Chappell et al., "Site-directed Mutagenesis and Kinetic Studies of the West Nile Virus NS3 Protease Identify Key Enzyme-Substrate Interactions," *J. Biol. Chem.*, 280(4): 2896-2903, 2005.

Charrel et al., "Evolutionary relationship between Old World West Nile virus strains Evidence for viral gene flow between Africa, the Middle East, and Europe," *Virology*, 315: 381-388, 2003.

Davis et al., "Emergence of attenuated West Nile virus variants in Texas, 2003," *Virology*, 330: 342-350, 2004.

Davis et al., "Genetic variation among temporally and geographically distinct West Nile virus isolates collected in the United States, 2001 and 2002," *Emerg. Infect. Dis.*, 9: 1423-1429, 2003.

Davis et al., Correction of "Genetic variation among temporally and geographically distinct West Nile virus isolates collected in the Unites States, 2001 and 2002," *Emerg. Infect. Dis.*, 10(1): 160, 2004.

Dockland et al., "West Nile Virus Core Protein: Tetramer Structure and Ribbon Formation," *Structure*, 12: 1157-1163, 2004.

Dunster et al., "Attenuation of virulence of flaviviurses following passage in HeLa cells," *J. Gen. Vir.*, 71: 601-607, 1990.

Dupuis et al., "Serological evidence of West Nile virus transmission, Jamaica, West Indies," *Emerg. Infect. Dis.*, 9: 860-863, 2003.

Ebel et al., "Genetic and Phenotypic Variation of West Nile Virus in New York, 2000-2003," *Am. J. Trop. Med. Hyg.*, 71(4): 493-500, 2004.

Egloff et al., "An RNA cap (nucleoside-2'-$O$-)-Methyltransferase in the flavivirus RNA polymerase NS5: crystal structure and functional characterization," *The EMBO Journal*, 21(11): 2757-2768, 2002.

Estrada-Franco et al., "West Nile virus in Mexico: evidence of widespread circulation since Jul. 2002," *Emerg. Infect. Dis.*, 9: 1604-1607, 2003.

Hall et al., "Loss of Dimerisation of the Nonstructural Protein NS1 or Kunjin Virus Delays Viral Replication and Reduces Virulence in Mice, but Still Allows Secretion of NS1," *Virology*, 264: 66-75, 1999.

Hall et al., "West Nile virus vaccines," *Expert Opin. Biol. Ther.*, 4(8): 1295-1305, 2004.

Hanley et al., "Paired charge-to-alanine mutagenesis of dengue virus type 4 NS5 generates mutants with temperature-sensitive, host range, and mouse attenuation phenotypes," *J. Virol.*, 76: 525-531, 2002.

Huang et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus," *J. Virology*, 79(12): 7300-7310, 2005.
Jones et al., "Flavivirus Capsid Is a Dimeric Alpha-Helical Protein," *J. Virology*, 77(12): 7143-7149, 2003.
Katz et al., "Isolation of an "Antigenic Variant" of West Nile Virus, Originating from a Chronic Infection of the Virus in LLC Cells," *Israel J. Med. Sci.*, 4(4): 911-913, 1968.
Kofler et al., "A novel principle of attenuation for the development of new generation live flavivirus vaccines," *Arch Virol Suppl*, (18): 191-200, 2004.
Kofler et al., "Mimicking live flavivirus immunization with a noninfectious RNA vaccine," *PNAS*, 101(7): 1951-1956, 2004.
Komar et al., "West Nile virus transmission in resident birds, Dominican Republic," *Emerg. Infect. Dis.*, 9: 1299-1302, 2003.
Lai et al., "Chimeric flaviviruses: novel vaccines against dengue fever, tick-borne encephalitis, and Japanese encephalitis," *Adv. Virus Res.*, 61: 469-509, 2003.
Lanciotti et al., "Complete Genome Sequences and Phylogenetic Analysis of West Nile Virus Strains Isolated from the United States, Europe, and the Middle East," *Virology*, 298: 96-105, 2002.
Lanciotti et al., "Nucleic Acid Sequence-Based Amplification Assays for Rapid Detection of West Nile and St. Louis Encephalitis Viruses," *J. Clinical Microbiology*, 39(12): 4506-4513, 2001.
Lanciotti et al., "Origin of the West Nile virus responsible for an outbreak of encephalitis in the northeastern U.S.," *Science*, 286: 2333-2337, 1999.
Lee et al., "Common E Protein Determinants for Attenuation of Glycosaminoglycan-Binding Variants of Japanese Encephalitis and West Nile Viruses," *J. Virology*, 78(15): 8271-8280, 2004.
Lustig et al., "A Live Attenuated West Nile Virus Strain as a Potential Veterinary Vaccine," *Viral Immunology*, 13(4): 401-410, 2000.
Lvov et al., "West Nile virus and other zoonotic viruses in Russia: examples of emerging-reemerging situations," *Arch Virol Suppl*, (18): 85-96, 2004.
Ma et al., "Solution structure of dengue virus capsid protein reveals another fold," *PNAS*, 101(10): 3414-3419, 2004.
Mashimo et al., "A nonsense mutation in the gene encoding 2'-5'-oligoadenylate synthetase/L1 isoform is associated with West Nile virus susceptibility in laboratory mice," *PNAS*, 99(17): 11311-11316, 2002.
McMinn, "The molecular basis of virulence of the encephalitogenic flaviviruses," *J. General Virology*, 78: 2711-2722, 1997.
Modis et al., "A ligand-binding pocket in the dengue virus envelope glycoprotein," *PNAS*, 100(12): 6986-6991, 2003.
Monath et al., *Flavivirus* es. In: Fields, B.N., Knipe, D.M., Howley, P.M. (Eds), Fields Virology. Lippincott-Raven, Philadelphia, pp. 961-1034, 1996.
Monath et al., "West Nile Virus Vaccine," *Current Drug Targets*, 1: 37-50, 2001.
Murgue et al., "The ecology and epidemiology of West Nile virus in Africa, Europe, and Asia," *Curr. Top. Microbiol. Immunol.*, 267: 195-221, 2002.
Murthy et al., "Crystal Structure of Dengue Virus NS3 Protease in Complex with a Bowman-Birk Inhibitors: Implications for Flaviviral Polyprotein Processing and Drug Design," *J. Mol. Biol.*, 301: 759-767, 2000.
Murthy et al., "Crystallization, characterization, and measurement of MAD data on crystals of dengue virus NS3 serine protease complexed with mung-bean Bowman-Birk inhibitor," *Acta Cryst.*, D55: 1370-1372, 1999.
Murthy et al., "Dengue Virus NS3 Serine Protease," *J. Biol. Chem.*, 274(9): 5573-5580, 1999.
Nall et al., "Enzymatic Characterisation and Homology Model Of A Catalytically Active Recombinant West Nile Virus NS3 Protease," *JBC Papers in Press*, published on Aug. 18, 2004 as Manuscript M406810200.
Papin et al., "SYBR Green-Based Real-Time Quantitative PCR Assay for Detection of West Nile Virus Circumvents False-Negative Results Due to Strain Variability," *J. Clinical Microbiology*, 42(4): 1511-1518, 2004.
Pletnev et al., "Molecularly engineered live-attenuated chimeric West Nile/dengue virus vaccines protect rhesus monkeys from West Nile virus," *Virology*, 314: 190-195, 2003.
Pletnev et al., "West Nile virus/dengue type 4 virus chimeras that are reduced in neurovirulence and peripheral virulence without loss of immunogenicity of protective efficacy," *PNAS*, 99(5): 3036-3041, 2002.
Quirin et al., "West Nile virus, Guadeloupe," *Emerg. Infect. Dis.*, 10: 706-708, 2004.
Rey et al., "The envelope glycoprotein from tick-borne encephalitis virus at 2 Å resolution," *Nature*, 375: 291-298, 1995.
Ryan et al., "Virus-encoded proteinases of the *Flaviviridae*," *J. General Virology*, 79: 947-959, 1998.
Shrestha et al., "infection and Injury of Neurons by West Nile Encephalitis Virus," *J. Virology*, 77(24): 13203-13213, 2003.
Solomon et al., "Pathogenesis and clinical features of Japanese encephalitis and West Nile virus infections," *Curr. Top. Micro. Immun.*, 267: 171-194, 2002.
van der Meulen et al., "West Nile virus in the vertebrate world," *Arch. Virol.*, 150: 637-657, 2005.
Volk et al., "Solution Structure and Antibody Binding Studies of the Envelope Protein Domain III from the New York strain of West Nile Virus," *JBC Papers in Press*, published on Jun. 9, 2004 as Manuscript M402385200.
Xie et al., "Mutation in NS5 protein attenuates mouse neurovirulence of yellow fever 17D vaccine virus," *J. General Virology*, 79: 1895-1899, 1998.

Yamshchikov et al., "An attenuated West Nile prototype virus is highly immunogenic and protects against the deadly NY99 strain: a candidate for live WN vaccine development," *Virology*, 330: 304-312, 2004.

Yu et al., "Solution Structure and Structural Dynamics of Envelope Protein Domain III of Mosquito- and Tick- Borne Flaviviruses," *Biochemistry*, 43: 9168-9176, 2004.

* cited by examiner

SEQUENCE LISTING

<160> NUMBER OF SEQ ID NOS: 52

<210> SEQ ID NO 1
<211> LENGTH: 11029
<212> TYPE: DNA
<213> ORGANISM: West Nile virus

<400> SEQUENCE: 1

| | | | | | |
|---|---|---|---|---|---|
| agtagttcgc | ctgtgtgagc | tgacaaactt | agtagtgttt | gtgaggatta | acaacaatta | 60 |
| acacagtgcg | agctgtttct | tagcacgaag | atctcgatgt | ctaagaaacc | aggagggccc | 120 |
| ggcaagagcc | gggctgtcaa | tatgctaaaa | cgcggaatgc | cccgcgtgtt | gtccttgatt | 180 |
| ggactgaaga | gggctatgtt | gagcctgatc | gacggcaagg | ggccaatacg | atttgtgttg | 240 |
| gctctcttgg | cgttcttcag | gttcacagca | attgctccga | cccgagcagt | gctggatcga | 300 |
| tggagaggtg | tgaacaaaca | aacagcgatg | aaacaccttc | tgagttttaa | gaaggaacta | 360 |
| gggaccttga | ccagtgctat | caatcggcgg | agctcaaaac | aaaagaaaag | aggaggaaag | 420 |
| accggaattg | cagtcatgat | tggcctgatc | gccagcgtag | gagcagttac | cctctctaac | 480 |
| ttccaaggga | aggtgatgat | gacggtaaat | gctactgacg | tcacagatgt | catcacgatt | 540 |
| ccaacagctg | ctggaaagaa | cctatgcatt | gtcagagcaa | tggatgtggg | atacatgtgc | 600 |
| gatgatacta | tcacttatga | atgcccagtg | ctgtcggctg | gtaatgatcc | agaagacatc | 660 |
| gactgttggt | gcacaaagtc | agcagtctac | gtcaggtatg | gaagatgcac | caagacacgc | 720 |
| cactcaagac | gcagtcggag | gtcactgaca | gtgcagacac | acggagaaag | cactctagcg | 780 |
| aacaagaagg | gggcttggat | ggacagcacc | aaggccacaa | ggtatttggt | aaaaacagaa | 840 |
| tcatggatct | tgaggaaccc | tggatatgcc | ctggtggcag | ccgtcattgg | ttggatgctt | 900 |
| gggagcaaca | ccatgcagag | agttgtgttt | gtcgtgctat | tgcttttggt | ggccccagct | 960 |
| tacagcttca | actgccttgg | aatgagcaac | agagacttct | ggaaggagt | gtctggagca | 1020 |
| acatgggtgg | atttggttct | cgaaggcgac | agctgcgtga | ctatcatgtc | taaggacaag | 1080 |
| cctaccatcg | atgtgaagat | gatgaatatg | gaggcggcca | acctggcaga | ggtccgcagt | 1140 |
| tattgctatt | tggctaccgt | cagcgatctc | tccaccaaag | ctgcgtgccc | gaccatggga | 1200 |
| gaagctcaca | atgacaaacg | tgctgaccca | gcttttgtgt | gcagacaagg | agtggtggac | 1260 |
| aggggctggg | gcaacggctg | cggactattt | ggcaaaggaa | gcattgacac | atgcgccaaa | 1320 |
| tttgcctgct | ctaccaaggc | aataggaaga | accatcttga | aagagaatat | caagtacgaa | 1380 |
| gtggccattt | ttgtccatgg | accaactact | gtggagtcgc | acgaaaacta | ctccacacag | 1440 |
| gttggagcca | ctcaggcagg | gagattcagc | atcactcctg | cggcgccttc | atacacacta | 1500 |
| aagcttggag | aatatggaga | ggtgacagtg | gactgtgaac | cacggtcagg | gattgacacc | 1560 |
| aatgcatact | acgtgatgac | tgttggaaca | aagacgttct | tggtccatcg | tgagtggttc | 1620 |
| atggacctca | acctcccttg | gagcagtgct | ggaagtactg | tgtggaggaa | cagagagacg | 1680 |
| ttaatggagt | ttgaggaacc | acacgccacg | aagcagtctg | tgatagcatt | gggctcacaa | 1740 |

```
gagggagctc tgcatcaagc tttggctgga gccattcctg tggaattttc aagcaacact    1800
gtcaagttga cgtcgggtca tttgaagtgt agagtgaaga tggaaaaatt gcagttgaag    1860
ggaacaacct atggcgtctg ttcaaaggct ttcaagtttc ttgggactcc cgcagacaca    1920
ggtcacggca ctgtggtgtt ggaattgcag tacactggca cggatggacc ttgcaaagtt    1980
cctatctcgt cagtggcttc attgaacgac ctaacgccag tgggcagatt ggtcactgtc    2040
aacccttttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag gagacacagc ttgggacttt ggatcagttg gaggggtgtt cacctcagtt    2280
gggaaggctg tccatcaagt gttcggagga gcattccgct cactgttcgg aggcatgtcc    2340
tggataacgc aaggattgct gggggctctc ctgttgtgga tgggcatcaa tgctcgtgat    2400
aggtccatag ctctcacgtt tctcgcagtt ggaggagttc tgctcttcct ctccgtgaac    2460
gtgcacgctg acactgggtg tgccatagac atcagccggc aagagctgag atgtggaagt    2520
ggagtgttca tacacaatga tgtggaggct tggatggacc ggtacaagta ttaccctgaa    2580
acgccacaag gcctagccaa gatcattcag aaagctcata ggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca cacctttgt ggttgatggt    2880
ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat tggaacggct gtcaagaaca acttggcgat ccacagtgac    3060
ctgtcctatt ggattgaaag caggctcaat gatacgtgga agcttgaaag gcagttctg    3120
ggtgaagtca atcatgtac gtggcctgag acgcatacct tgtggggcga tggaatcctt    3180
gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc caggaactac ggtcacccctg agtgagagct gcggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgaccctt ttcagttggg ccttctggtc gtgttcttgg ccacccagga ggtccttcgc    3600
aagaggtgga cagccaagat cagcatgcca gctatactga ttgctctgct agtcctggtg    3660
tttgggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca acgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagctgca aaaaagaaag gagcaagtct gctatgcttg    4140
```

-continued

```
gctctagcct caacaggact tttcaacccc atgatccttg ctgctggact gattgcatgt    4200
gatcccaacc gtaaacgcgg atggcccgca actgaagtga tgacagctgt cggcctaatg    4260
tttgccatcg tcggagggct ggcagagctt gacattgact ccatggccat tccaatgact    4320 atcgcgggc tcatgtttgc tgctttcgtg atttctggga aatcaacaga tatgtggatt    4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac ccctgggca    4560 atcttgccct cagtagttgg atttttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa    4740
ggtgttttcc acacctttg gcatacaaca aaaggagccg cttttgatgag cggagagggc    4800 cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg cgccggtaa acaaggagg    5220 attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc tagggaggc ggcggcaata ttcatgacag ccaccccacc aggcacttca    5580
gatccattcc cagagtccaa ttcaccaatt tccgacttac agactgagat cccggatcga    5640
gcttggaact ctggatacga atggatcaca gaatacaccg gaagacggt ttggtttgtg    5700 cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggga    6180 taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaaacacaat tttagaagaca acaacgaagt ggaagtcatc    6360
acgaagcttg gtgaaaggaa gattctgagg ccgcgctgga ttgacgccag ggtgtactcg    6420
gatcaccagg cactaaaggc gttcaaggac ttcgcctcgg gaaaacgttc tcagataggg    6480
```

```
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac ctttttctgt tggatggctg aagttccagg aacgaagatc    6780
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttttggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctggggacaa gtcacccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg gaattttgat cacggccgca gcggtgacgc tttgggagaa tggagcaagc    7560
tctgtttgga acgcaacaac tgccatcgga ctctgccaca tcatgcgtgg gggttggttg    7620
tcatgtctat ccataacatg gacactcata aagaacatgg aaaaaccagg actaaaaaga    7680
ggtggggcaa aaggacgcac cttgggagag gttggaaag aaagactcaa ccagatgaca    7740
aaagaagagt tcactaggta ccgcaaagag gccatcatcg aagtcgatcg ctcagcggca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtggagtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgcccta catgccgaaa gtcatagaga agatggagct gctccaacgc    8280
cggtatgggg gggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggacccccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atgagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa tgagaccacc    8820
aactggttgt gggcgttttt ggccagagaa aaacgtccca aatgtgctc tcgagaggaa    8880
```

```
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccggagagtt cggaaaggcc aagggaagca gagccatttg gttcatgtgg    9120
ctcggagctc gctttctgga gttcgaggct ctgggttttc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
ggggaacatc ggcgtcttgc cagggccatc attgagctca cctatcgtca caaagttgtg    9420
aaagtgatgc gcccggctgc tgatggaaga accgtcatgg atgttatctc cagagaagat    9480
cagagggggg gtggacaagt tgtcacctac gccctaaaca ctttcaccaa cctggccgtc    9540
cagctggtga ggatgatgga aggggaagga gtgattggcc cagatgatgt ggagaaactc    9600
acaaaaggga aggacccaa agtcaggacc tggctgtttg agaatgggga gaaagactc    9660
agccgcatgg ctgtcagtgg agatgactgt gtggtaaagc ccctggacga tcgctttgcc    9720
acctcgctcc acttcctcaa tgctatgtca aaggttcgca aagacatcca agagtggaaa    9780
ccgtcaactg gatggtatga ttggcagcag gttccatttt gctcaaacca tttcactgaa    9840
ttgatcatga agatggaag aacactggtg gttccatgcc gaggacagga tgaattggta    9900
ggcagagctc gcatatctcc aggggccgga tggaacgtcc gcgacactgc ttgtctggct    9960
aagtcttatg cccagatgtg gctgcttctg tacttccaca agagacct gcggctcatg   10020
gccaacgcca tttgctccgc tgtccctgtg aattgggtcc ctaccggaag aaccacgtgg   10080
tccatccatg caggaggaga gtggatgaca acagaggaca tgttggaggt ctggaaccgt   10140
gtttggatag aggagaatga atggatgaa gacaaaaccc cagtggagaa atggagtgac   10200
gtcccatatt caggaaaacg agaggacatc tggtgtggca gcctgattgg cacaagagcc   10260
cgagccacgt gggcagaaaa catccaggtg gctatcaacc aagtcagagc aatcatcgga   10320
gatgagaagt atgtggatta catgagttca ctaaagagat atgaagacac aactttggtt   10380
gaggacacag tactgtagat atttaatcaa ttgtaaatag acaatataag tatgcataaa   10440
agtgtagttt tatagtagta tttagtggtg ttagtgtaaa tagttaagaa aattttgagg   10500
agaaagtcag gccgggaagt tcccgccacc ggaagttgag tagacggtgc tgcctgcgac   10560
tcaaccccag gaggactggg tgaacaaagc cgcgaagtga tccatgtaag ccctcagaac   10620
cgtctcggaa ggaggacccc acatgttgta acttcaaagc ccaatgtcag accacgctac   10680
ggcgtgctac tctgcggaga gtgcagtctg cgatagtgcc ccaggaggac tgggttaaca   10740
aaggcaaacc aacgccccac gcggccctag ccccggtaat ggtgttaacc agggcgaaag   10800
gactagaggt tagaggagac cccgcggttt aaagtgcacg gcccagcctg actgaagctg   10860
taggtcaggg gaaggactag aggttagtgg agacccgtg ccacaaaaca ccacaacaaa   10920
acagcatatt gacacctggg atagactagg agatcttctg ctctgcacaa ccagccacac   10980
ggcacagtgc gccgacaatg gtggctggtg gtgcgagaac acaggatct                11029
```

<210> SEQ ID NO 2
<211> LENGTH: 3433
<212> TYPE: PRT
<213> ORGANISM: West Nile virus

<400> SEQUENCE: 2

```
Met Ser Lys Lys Pro Gly Gly Pro Gly Lys Ser Arg Ala Val Asn Met
  1               5                  10                  15

Leu Lys Arg Gly Met Pro Arg Val Leu Ser Leu Ile Gly Leu Lys Arg
             20                  25                  30

Ala Met Leu Ser Leu Ile Asp Gly Lys Gly Pro Ile Arg Phe Val Leu
         35                  40                  45

Ala Leu Leu Ala Phe Phe Arg Phe Thr Ala Ile Ala Pro Thr Arg Ala
     50                  55                  60

Val Leu Asp Arg Trp Arg Gly Val Asn Lys Gln Thr Ala Met Lys His
 65                  70                  75                  80

Leu Leu Ser Phe Lys Lys Glu Leu Gly Thr Leu Thr Ser Ala Ile Asn
                 85                  90                  95

Arg Arg Ser Ser Lys Gln Lys Lys Arg Gly Gly Lys Thr Gly Ile Ala
                100                 105                 110

Val Met Ile Gly Leu Ile Ala Ser Val Gly Ala Val Thr Leu Ser Asn
            115                 120                 125

Phe Gln Gly Lys Val Met Met Thr Val Asn Ala Thr Asp Val Thr Asp
        130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
                180                 185                 190

Thr Lys Ser Ala Val Tyr Val Arg Tyr Gly Arg Cys Thr Lys Thr Arg
            195                 200                 205

His Ser Arg Arg Ser Arg Arg Ser Leu Thr Val Gln Thr His Gly Glu
        210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Val Leu Leu Leu Leu Val Ala Pro Ala
        275                 280                 285

Tyr Ser Phe Asn Cys Leu Gly Met Ser Asn Arg Asp Phe Leu Glu Gly
    290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
    370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415
```

```
Gly Arg Thr Ile Leu Lys Glu Asn Ile Lys Tyr Glu Val Ala Ile Phe
            420                 425                 430

Val His Gly Pro Thr Thr Val Glu Ser His Gly Asn Tyr Ser Thr Gln
            435                 440                 445

Val Gly Ala Thr Gln Ala Gly Arg Phe Ser Ile Thr Pro Ala Ala Pro
            450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
            485                 490                 495

Gly Thr Lys Thr Phe Leu Val His Arg Glu Trp Phe Met Asp Leu Asn
            500                 505                 510

Leu Pro Trp Ser Ser Ala Gly Ser Thr Val Trp Arg Asn Arg Glu Thr
            515                 520                 525

Leu Met Glu Phe Glu Glu Pro His Ala Thr Lys Gln Ser Val Ile Ala
            530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
            565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
            595                 600                 605

Gly His Gly Thr Val Val Leu Glu Leu Gln Tyr Thr Gly Thr Asp Gly
            610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
            645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
            675                 680                 685

Lys Ser Gly Ser Ser Ile Gly Lys Ala Phe Thr Thr Thr Leu Lys Gly
            690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
            725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
            770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
            805                 810                 815

Glu Ala Trp Met Asp Arg Tyr Lys Tyr Tyr Pro Glu Thr Pro Gln Gly
            820                 825                 830
```

-continued

```
Leu Ala Lys Ile Ile Gln Lys Ala His Lys Glu Gly Val Cys Gly Leu
        835                 840                 845
Arg Ser Val Ser Arg Leu Glu His Gln Met Trp Glu Ala Val Lys Asp
    850                 855                 860
Glu Leu Asn Thr Leu Leu Lys Glu Asn Gly Val Asp Leu Ser Val Val
865                 870                 875                 880
Val Glu Lys Gln Glu Gly Met Tyr Lys Ser Ala Pro Lys Arg Leu Thr
                885                 890                 895
Ala Thr Thr Glu Lys Leu Glu Ile Gly Trp Lys Ala Trp Gly Lys Ser
            900                 905                 910
Ile Leu Phe Ala Pro Glu Leu Ala Asn Asn Thr Phe Val Val Asp Gly
        915                 920                 925
Pro Glu Thr Lys Glu Cys Pro Thr Gln Asn Arg Ala Trp Asn Ser Leu
    930                 935                 940
Glu Val Glu Asp Phe Gly Phe Gly Leu Thr Ser Thr Arg Met Phe Leu
945                 950                 955                 960
Lys Val Arg Glu Ser Asn Thr Thr Glu Cys Asp Ser Lys Ile Ile Gly
                965                 970                 975
Thr Ala Val Lys Asn Asn Leu Ala Ile His Ser Asp Leu Ser Tyr Trp
            980                 985                 990
Ile Glu Ser Arg Leu Asn Asp Thr Trp Lys Leu Glu Arg Ala Val Leu
        995                 1000                1005
Gly Glu Val Lys Ser Cys Thr Trp Pro Glu Thr His Thr Leu Trp Gly
    1010                1015                1020
Asp Gly Ile Leu Glu Ser Asp Leu Ile Ile Pro Val Thr Leu Ala Gly
1025                1030                1035                1040
Pro Arg Ser Asn His Asn Arg Arg Pro Gly Tyr Lys Thr Gln Asn Gln
                1045                1050                1055
Gly Pro Trp Asp Glu Gly Arg Val Glu Ile Asp Phe Asp Tyr Cys Pro
            1060                1065                1070
Gly Thr Thr Val Thr Leu Ser Glu Ser Cys Gly His Arg Gly Pro Ala
        1075                1080                1085
Thr Arg Thr Thr Thr Glu Ser Gly Lys Leu Ile Thr Asp Trp Cys Cys
    1090                1095                1100
Arg Ser Cys Thr Leu Pro Pro Leu Arg Tyr Gln Thr Asp Ser Gly Cys
1105                1110                1115                1120
Trp Tyr Gly Met Glu Ile Arg Pro Gln Arg His Asp Glu Lys Thr Leu
                1125                1130                1135
Val Gln Ser Gln Val Asn Ala Tyr Asn Ala Asp Met Ile Asp Pro Phe
            1140                1145                1150
Gln Leu Gly Leu Leu Val Val Phe Leu Ala Thr Gln Glu Val Leu Arg
        1155                1160                1165
Lys Arg Trp Thr Ala Lys Ile Ser Met Pro Ala Ile Leu Ile Ala Leu
    1170                1175                1180
Leu Val Leu Val Phe Gly Gly Ile Thr Tyr Thr Asp Val Leu Arg Tyr
1185                1190                1195                1200
Val Ile Leu Val Gly Ala Ala Phe Ala Glu Ser Asn Ser Gly Gly Asp
                1205                1210                1215
Val Val His Leu Ala Leu Met Ala Thr Phe Lys Ile Gln Pro Val Phe
            1220                1225                1230
Met Val Ala Ser Phe Leu Lys Ala Arg Trp Thr Asn Gln Glu Asn Ile
        1235                1240                1245
Leu Leu Met Leu Ala Ala Val Phe Phe Gln Met Ala Tyr His Asp Ala
```

-continued

```
              1250                1255                1260
Arg Gln Ile Leu Leu Trp Glu Ile Pro Asp Val Leu Asn Ser Leu Ala
1265                1270                1275                1280

Val Ala Trp Met Ile Leu Arg Ala Ile Thr Phe Thr Thr Thr Ser Asn
              1285                1290                1295

Val Val Val Pro Leu Leu Ala Leu Leu Thr Pro Gly Leu Arg Cys Leu
              1300                1305                1310

Asn Leu Asp Val Tyr Arg Ile Leu Leu Leu Met Val Gly Ile Gly Ser
                1315                1320                1325

Leu Ile Arg Glu Lys Arg Ser Ala Ala Ala Lys Lys Lys Gly Ala Ser
      1330                1335                1340

Leu Leu Cys Leu Ala Leu Ala Ser Thr Gly Leu Phe Asn Pro Met Ile
1345                1350                1355                1360

Leu Ala Ala Gly Leu Ile Ala Cys Asp Pro Asn Arg Lys Arg Gly Trp
              1365                1370                1375

Pro Ala Thr Glu Val Met Thr Ala Val Gly Leu Met Phe Ala Ile Val
              1380                1385                1390

Gly Gly Leu Ala Glu Leu Asp Ile Asp Ser Met Ala Ile Pro Met Thr
        1395                1400                1405

Ile Ala Gly Leu Met Phe Ala Ala Phe Val Ile Ser Gly Lys Ser Thr
      1410                1415                1420

Asp Met Trp Ile Glu Arg Thr Ala Asp Ile Ser Trp Glu Ser Asp Ala
1425                1430                1435                1440

Glu Ile Thr Gly Ser Ser Glu Arg Val Asp Val Arg Leu Asp Asp
              1445                1450                1455

Gly Asn Phe Gln Leu Met Asn Asp Pro Gly Ala Pro Trp Lys Ile Trp
              1460                1465                1470

Met Leu Arg Met Val Cys Leu Ala Ile Ser Ala Tyr Thr Pro Trp Ala
              1475                1480                1485

Ile Leu Pro Ser Val Val Gly Phe Trp Ile Thr Leu Gln Tyr Thr Lys
      1490                1495                1500

Arg Gly Gly Val Leu Trp Asp Thr Pro Ser Pro Lys Glu Tyr Lys Lys
1505                1510                1515                1520

Gly Asp Thr Thr Thr Gly Val Tyr Arg Ile Met Thr Arg Gly Leu Leu
              1525                1530                1535

Gly Ser Tyr Gln Ala Gly Ala Gly Val Met Val Glu Gly Val Phe His
              1540                1545                1550

Thr Leu Trp His Thr Thr Lys Gly Ala Ala Leu Met Ser Gly Glu Gly
        1555                1560                1565

Arg Leu Asp Pro Tyr Trp Gly Ser Val Lys Glu Asp Arg Leu Cys Tyr
      1570                1575                1580

Gly Gly Pro Trp Lys Leu Gln His Lys Trp Asn Gly Gln Asp Glu Val
1585                1590                1595                1600

Gln Met Ile Val Val Glu Pro Gly Lys Asn Val Lys Asn Val Gln Thr
              1605                1610                1615

Lys Pro Gly Val Phe Lys Thr Pro Glu Gly Glu Ile Gly Ala Val Thr
              1620                1625                1630

Leu Asp Phe Pro Thr Gly Thr Ser Gly Ser Pro Ile Val Asp Lys Asn
        1635                1640                1645

Gly Asp Val Ile Gly Leu Tyr Gly Asn Gly Val Ile Met Pro Asn Gly
      1650                1655                1660

Ser Tyr Ile Ser Ala Ile Val Gln Gly Glu Arg Met Asp Glu Pro Ile
1665                1670                1675                1680
```

-continued

```
Pro Ala Gly Phe Glu Pro Glu Met Leu Arg Lys Lys Gln Ile Thr Val
            1685                1690                1695

Leu Asp Leu His Pro Gly Ala Gly Lys Thr Arg Arg Ile Leu Pro Gln
            1700                1705                1710

Ile Ile Lys Glu Ala Ile Asn Arg Arg Leu Arg Thr Ala Val Leu Ala
        1715                1720                1725

Pro Thr Arg Val Val Ala Ala Glu Met Ala Glu Ala Leu Arg Gly Leu
    1730                1735                1740

Pro Ile Arg Tyr Gln Thr Ser Ala Val Pro Arg Glu His Asn Gly Asn
1745                1750                1755                1760

Glu Ile Val Asp Val Met Cys His Ala Thr Leu Thr His Arg Leu Met
            1765                1770                1775

Ser Pro His Arg Val Pro Asn Tyr Asn Leu Phe Val Met Asp Glu Ala
            1780                1785                1790

His Phe Thr Asp Pro Ala Ser Ile Ala Ala Arg Gly Tyr Ile Ser Thr
        1795                1800                1805

Lys Val Glu Leu Gly Glu Ala Ala Ala Ile Phe Met Thr Ala Thr Pro
    1810                1815                1820

Pro Gly Thr Ser Asp Pro Phe Pro Glu Ser Asn Ser Pro Ile Ser Asp
1825                1830                1835                1840

Leu Gln Thr Glu Ile Pro Asp Arg Ala Trp Asn Ser Gly Tyr Glu Trp
            1845                1850                1855

Ile Thr Glu Tyr Thr Gly Lys Thr Val Trp Phe Val Pro Ser Val Lys
            1860                1865                1870

Met Gly Asn Glu Ile Ala Leu Cys Leu Gln Arg Ala Gly Lys Lys Val
        1875                1880                1885

Val Gln Leu Asn Arg Lys Ser Tyr Glu Thr Glu Tyr Pro Lys Cys Lys
    1890                1895                1900

Asn Asp Asp Trp Asp Phe Val Ile Thr Thr Asp Ile Ser Glu Met Gly
1905                1910                1915                1920

Ala Asn Phe Lys Ala Ser Arg Val Ile Asp Ser Arg Lys Ser Val Lys
            1925                1930                1935

Pro Thr Ile Ile Thr Glu Gly Glu Gly Arg Val Ile Leu Gly Glu Pro
        1940                1945                1950

Ser Ala Val Thr Ala Ala Ser Ala Ala Gln Arg Arg Gly Arg Ile Gly
        1955                1960                1965

Arg Asn Pro Ser Gln Val Gly Asp Glu Tyr Cys Tyr Gly Gly His Thr
    1970                1975                1980

Asn Glu Asp Asp Ser Asn Phe Ala His Trp Thr Glu Ala Arg Ile Met
1985                1990                1995                2000

Leu Asp Asn Ile Asn Met Pro Asn Gly Leu Ile Ala Gln Phe Tyr Gln
            2005                2010                2015

Pro Glu Arg Glu Lys Val Tyr Thr Met Asp Gly Glu Tyr Arg Leu Arg
        2020                2025                2030

Gly Glu Glu Arg Lys Asn Phe Leu Glu Leu Leu Arg Thr Ala Asp Leu
    2035                2040                2045

Pro Val Trp Leu Ala Tyr Lys Val Ala Ala Ala Gly Val Ser Tyr His
    2050                2055                2060

Asp Arg Arg Trp Cys Phe Asp Gly Pro Arg Thr Asn Thr Ile Leu Glu
2065                2070                2075                2080

Asp Asn Asn Glu Val Glu Val Ile Thr Lys Leu Gly Glu Arg Lys Ile
            2085                2090                2095
```

```
Leu Arg Pro Arg Trp Ile Asp Ala Arg Val Tyr Ser Asp His Gln Ala
        2100                2105                2110

Leu Lys Ala Phe Lys Asp Phe Ala Ser Gly Lys Arg Ser Gln Ile Gly
        2115                2120                2125

Leu Ile Glu Val Leu Gly Lys Met Pro Glu His Phe Met Gly Lys Thr
    2130                2135                2140

Trp Glu Ala Leu Asp Thr Met Tyr Val Val Ala Thr Ala Glu Lys Gly
2145                2150                2155                2160

Gly Arg Ala His Arg Met Ala Leu Glu Glu Leu Pro Asp Ala Leu Gln
            2165                2170                2175

Thr Ile Ala Leu Ile Ala Leu Leu Ser Val Met Thr Met Gly Val Phe
            2180                2185                2190

Phe Leu Leu Met Gln Arg Lys Gly Ile Gly Lys Ile Gly Leu Gly Gly
        2195                2200                2205

Ala Val Leu Gly Val Ala Thr Phe Phe Cys Trp Met Ala Glu Val Pro
    2210                2215                2220

Gly Thr Lys Ile Ala Gly Met Leu Leu Leu Ser Leu Leu Leu Met Ile
2225                2230                2235                2240

Val Leu Ile Pro Glu Pro Glu Lys Gln Arg Ser Gln Thr Asp Asn Gln
        2245                2250                2255

Leu Ala Val Phe Leu Ile Cys Val Met Thr Leu Val Ser Ala Val Ala
        2260                2265                2270

Ala Asn Glu Met Gly Trp Leu Asp Lys Thr Lys Ser Asp Ile Ser Ser
        2275                2280                2285

Leu Phe Gly Gln Arg Ile Glu Val Lys Glu Asn Phe Ser Met Gly Glu
        2290                2295                2300

Phe Leu Leu Asp Leu Arg Pro Ala Thr Ala Trp Ser Leu Tyr Ala Val
2305                2310                2315                2320

Thr Thr Ala Val Leu Thr Pro Leu Leu Lys His Leu Ile Thr Ser Asp
            2325                2330                2335

Tyr Ile Asn Thr Ser Leu Thr Ser Ile Asn Val Gln Ala Ser Ala Leu
        2340                2345                2350

Phe Thr Leu Ala Arg Gly Phe Pro Phe Val Asp Val Gly Val Ser Ala
        2355                2360                2365

Leu Leu Leu Ala Ala Gly Cys Trp Gly Gln Val Thr Leu Thr Val Thr
        2370                2375                2380

Val Thr Ala Ala Thr Leu Leu Phe Cys His Tyr Ala Tyr Met Val Pro
2385                2390                2395                2400

Gly Trp Gln Ala Glu Ala Met Arg Ser Ala Gln Arg Arg Thr Ala Ala
            2405                2410                2415

Gly Ile Met Lys Asn Ala Val Val Asp Gly Ile Val Ala Thr Asp Val
        2420                2425                2430

Pro Glu Leu Glu Arg Thr Thr Pro Ile Met Gln Lys Lys Val Gly Gln
        2435                2440                2445

Ile Met Leu Ile Leu Val Ser Leu Ala Ala Val Val Val Asn Pro Ser
        2450                2455                2460

Val Lys Thr Val Arg Glu Ala Gly Ile Leu Ile Thr Ala Ala Ala Val
2465                2470                2475                2480

Thr Leu Trp Glu Asn Gly Ala Ser Ser Val Trp Asn Ala Thr Thr Ala
            2485                2490                2495

Ile Gly Leu Cys His Ile Met Arg Gly Gly Trp Leu Ser Cys Leu Ser
        2500                2505                2510

Ile Thr Trp Thr Leu Ile Lys Asn Met Glu Lys Pro Gly Leu Lys Arg
```

-continued

```
            2515                2520                2525
Gly Gly Ala Lys Gly Arg Thr Leu Gly Glu Val Trp Lys Glu Arg Leu
        2530                2535                2540

Asn Gln Met Thr Lys Glu Glu Phe Thr Arg Tyr Arg Lys Glu Ala Ile
2545                2550                2555                2560

Ile Glu Val Asp Arg Ser Ala Ala Lys His Ala Arg Lys Glu Gly Asn
            2565                2570                2575

Val Thr Gly Gly His Pro Val Ser Arg Gly Thr Ala Lys Leu Arg Trp
        2580                2585                2590

Leu Val Glu Arg Arg Phe Leu Glu Pro Val Gly Lys Val Ile Asp Leu
    2595                2600                2605

Gly Cys Gly Arg Gly Gly Trp Cys Tyr Tyr Met Ala Thr Gln Lys Arg
    2610                2615                2620

Val Gln Glu Val Arg Gly Tyr Thr Lys Gly Gly Pro Gly His Glu Glu
2625                2630                2635                2640

Pro Gln Leu Val Gln Ser Tyr Gly Trp Asn Ile Val Thr Met Lys Ser
            2645                2650                2655

Gly Val Asp Val Phe Tyr Arg Pro Ser Glu Cys Cys Asp Thr Leu Leu
        2660                2665                2670

Cys Asp Ile Gly Glu Ser Ser Ser Ala Glu Val Glu Glu His Arg
    2675                2680                2685

Thr Ile Arg Val Leu Glu Met Val Glu Asp Trp Leu His Arg Gly Pro
    2690                2695                2700

Arg Glu Phe Cys Val Lys Val Leu Cys Pro Tyr Met Pro Lys Val Ile
2705                2710                2715                2720

Glu Lys Met Glu Leu Leu Gln Arg Arg Tyr Gly Gly Gly Leu Val Arg
            2725                2730                2735

Asn Pro Leu Ser Arg Asn Ser Thr His Glu Met Tyr Trp Val Ser Arg
        2740                2745                2750

Ala Ser Gly Asn Val Val His Ser Val Asn Met Thr Ser Gln Val Leu
    2755                2760                2765

Leu Gly Arg Met Glu Lys Arg Thr Trp Lys Gly Pro Gln Tyr Glu Glu
    2770                2775                2780

Asp Val Asn Leu Gly Ser Gly Thr Arg Ala Val Gly Lys Pro Leu Leu
2785                2790                2795                2800

Asn Ser Asp Thr Ser Lys Ile Lys Asn Arg Ile Glu Arg Leu Arg Arg
            2805                2810                2815

Glu Tyr Ser Ser Thr Trp His His Asp Glu Asn His Pro Tyr Arg Thr
        2820                2825                2830

Trp Asn Tyr His Gly Ser Tyr Asp Val Lys Pro Thr Gly Ser Ala Ser
    2835                2840                2845

Ser Leu Val Asn Gly Val Val Arg Leu Leu Ser Lys Pro Trp Asp Thr
    2850                2855                2860

Ile Thr Asn Val Thr Thr Met Ala Met Thr Asp Thr Thr Pro Phe Gly
2865                2870                2875                2880

Gln Gln Arg Val Phe Lys Glu Lys Val Asp Thr Lys Ala Pro Glu Pro
            2885                2890                2895

Pro Glu Gly Val Lys Tyr Val Leu Asn Glu Thr Thr Asn Trp Leu Trp
        2900                2905                2910

Ala Phe Leu Ala Arg Glu Lys Arg Pro Arg Met Cys Ser Arg Glu Glu
    2915                2920                2925

Phe Ile Arg Lys Val Asn Ser Asn Ala Ala Leu Gly Ala Met Phe Glu
2930                2935                2940
```

-continued

Glu Gln Asn Gln Trp Arg Ser Ala Arg Glu Ala Val Glu Asp Pro Lys
2945                2950                2955                2960

Phe Trp Glu Met Val Asp Glu Arg Glu Ala His Leu Arg Gly Glu
        2965                2970                2975

Cys His Thr Cys Ile Tyr Asn Met Met Gly Lys Arg Glu Lys Lys Pro
            2980                2985                2990

Gly Glu Phe Gly Lys Ala Lys Gly Ser Arg Ala Ile Trp Phe Met Trp
        2995                3000                3005

Leu Gly Ala Arg Phe Leu Glu Phe Glu Ala Leu Gly Phe Leu Asn Glu
    3010                3015                3020

Asp His Trp Leu Gly Arg Lys Asn Ser Gly Gly Gly Val Glu Gly Leu
3025                3030                3035                3040

Gly Leu Gln Lys Leu Gly Tyr Ile Leu Arg Glu Val Gly Thr Arg Pro
        3045                3050                3055

Gly Gly Lys Ile Tyr Ala Asp Asp Thr Ala Gly Trp Asp Thr Arg Ile
        3060                3065                3070

Thr Arg Ala Asp Leu Glu Asn Glu Ala Lys Val Leu Glu Leu Leu Asp
    3075                3080                3085

Gly Glu His Arg Arg Leu Ala Arg Ala Ile Ile Glu Leu Thr Tyr Arg
    3090                3095                3100

His Lys Val Val Lys Val Met Arg Pro Ala Ala Asp Gly Arg Thr Val
3105                3110                3115                3120

Met Asp Val Ile Ser Arg Glu Asp Gln Arg Gly Ser Gly Gln Val Val
            3125                3130                3135

Thr Tyr Ala Leu Asn Thr Phe Thr Asn Leu Ala Val Gln Leu Val Arg
        3140                3145                3150

Met Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn Gly
    3170                3175                3180

Glu Glu Arg Leu Ser Arg Met Ala Val Ser Gly Asp Asp Cys Val Val
3185                3190                3195                3200

Lys Pro Leu Asp Asp Arg Phe Ala Thr Ser Leu His Phe Leu Asn Ala
        3205                3210                3215

Met Ser Lys Val Arg Lys Asp Ile Gln Glu Trp Lys Pro Ser Thr Gly
        3220                3225                3230

Trp Tyr Asp Trp Gln Gln Val Pro Phe Cys Ser Asn His Phe Thr Glu
        3235                3240                3245

Leu Ile Met Lys Asp Gly Arg Thr Leu Val Val Pro Cys Arg Gly Gln
    3250                3255                3260

Asp Glu Leu Val Gly Arg Ala Arg Ile Ser Pro Gly Ala Gly Trp Asn
3265                3270                3275                3280

Val Arg Asp Thr Ala Cys Leu Ala Lys Ser Tyr Ala Gln Met Trp Leu
        3285                3290                3295

Leu Leu Tyr Phe His Arg Arg Asp Leu Arg Leu Met Ala Asn Ala Ile
        3300                3305                3310

Cys Ser Ala Val Pro Val Asn Trp Val Pro Thr Gly Arg Thr Thr Trp
    3315                3320                3325

Ser Ile His Ala Gly Gly Glu Trp Met Thr Thr Glu Asp Met Leu Glu
    3330                3335                3340

Val Trp Asn Arg Val Trp Ile Glu Glu Asn Glu Trp Met Glu Asp Lys
3345                3350                3355                3360

```
Thr Pro Val Glu Lys Trp Ser Asp Val Pro Tyr Ser Gly Lys Arg Glu
            3365                3370                3375
Asp Ile Trp Cys Gly Ser Leu Ile Gly Thr Arg Ala Arg Ala Thr Trp
        3380                3385                3390
Ala Glu Asn Ile Gln Val Ala Ile Asn Gln Val Arg Ala Ile Ile Gly
            3395                3400                3405
Asp Glu Lys Tyr Val Asp Tyr Met Ser Ser Leu Lys Arg Tyr Glu Asp
    3410                3415                3420
Thr Thr Leu Val Glu Asp Thr Val Leu
3425                3430

<210> SEQ ID NO 3
<211> LENGTH: 11029
<212> TYPE: DNA
<213> ORGANISM: West Nile virus

<400> SEQUENCE: 3
agtagttcgc ctgtgtgagc tgacaaactt agtagtgttt gtgaggatta acaacaatta     60
acacagtgcg agctgtttct tagcacgaag atctcgatgt ctaagaaacc aggagggccc    120
ggcaagagcc gggctgtcaa tatgctaaaa cgcggaatgc cccgcgtgtt gtccttgatt    180
ggactgaaga gggctatgtt gagcctgatc gacggcaagg gccaatacg atttgtgttg     240 gctctcttgg cgttcttcag gttcacagca attgctccga cccgagcagt gctggatcga    300
tggagaggtg tgaacaaaca aacagcgatg aaacaccttc tgagttttaa gaaggaacta    360
gggaccttga ccagtgctat caatcggcgg agctcaaaac aaaagaaaag aggaggaaag    420
accggaattg cagtcatgat tggcctgatc gccagcgtag gagcagttac cctctctaac    480
ttccaaggga aggtgatgat gacggtaaat gctactgacg tcacagatgt catcacgatt    540
ccaacagctg ctggaaagaa cctatgcatt gtcagagcaa tggatgtggg atacatgtgc    600
gatgatacta tcacttatga atgcccagtg ctgtcggctg gtaatgatcc agaagacatt    660
gactgttggt gcacaaagtc agcagtctac gtcaggtatg aagatgcac aagacacgc     720 cactcaagac gcagtcggag gtcactgaca gtgcagacac acgagaaaag cactctagcg    780
aacaagaagg gggcttggat ggacagcacc aaggccacaa ggtatttggt aaaaacagaa    840
tcatggatct tgaggaaccc tggatatgcc tggtggcag ccgtcattgg ttggatgctt     900
gggagcaaca ccatgcagag agttgtgttt atcgtgctat tgcttttggt ggccccagct    960
tacagcttca actgccttgg aatgagcaac agagacttct ggaaggagt gtctggagca   1020 acatgggtgg atttggttct cgaaggcgac agctgcgtga ctattatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc gaccatggga   1200
gaagctcaca tgacaaacg tgctgaccca gcttttgtgt gcagacaagg agtggtggac    1260
aggggctggg gcaacggctg cggactattt ggcaaaggaa gcattgacac atgcgccaaa   1320
tttgcctgct ctaccaaggc aataggaaga accatcttga agagaatat caagtacgaa    1380 gtggccattt ttgtccatgg accaactact gtggagtcgc acggaaacta ctccacacag   1440
gctggagcca ctcaggcagg agattcagc atcactcctg cggcgccttc atacacacta    1500
aagcttggag aatatggaga ggtgacagtg gactgtgaac acggtcagg gattgacacc   1560 aatgcatact acgtgatgac tgttggaaca aagacgttct ggtccatcg tgagtggttc   1620 atggacctca acctcccttg gagcagtgct ggaagtactg tgtggaggaa cagagagacg   1680
```

```
ttaatggagt tgaggaacc acacgccacg aagcagtctg tgatagcatt gggctcacaa    1740
gagggagctc tgcatcaagc tttggctgga gccattcctg tggaattttc aagcaacact    1800
gtcaagttga cgtcgggtca tttgaagtgt agagtgaaga tggaaaaatt acagttgaag    1860
ggaacaacct atggcgtctg ttcaaaggct ttcaagtttc ttgggactcc cgcagacaca    1920
ggtcacggca ctgtggtgtt ggaattgcag tacactggca cggatggacc ttgcaaagtt    1980
cctatctcgt cagtggcttc attgaacgac ctaacgccag tgggcagatt ggtcactgtc    2040
aacccttttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc cagagacta    2220 gccgctctag gagacacagc ttgggacttt ggatcagttg gaggggtgtt cacctcagtt    2280
gggaaggctg tccatcaagt gttcggagga gcattccgct cactgttcgg aggcatgtcc    2340
tggataacgc aaggattgct gggggctctc ctgttgtgga tgggcatcaa tgctcgtgat    2400
aggtccatag ctctcacgtt tctcgcagtt ggaggagttc tgctcttcct ctccgtgaac    2460
gtgcatgctg acactgggtg tgccatagac atcagccggc aagagctgag atgtggaagt    2520
ggagtgttca tacacaatga tgtggaggct tggatggacc ggtacaagta ttaccctgaa    2580
acgccacaag gcctagccaa gatcattcag aaagctcata aggaaggagt gtgcggtcta    2640
cgatcagttt ccagattgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca caccttttgt ggttgatggt    2880
ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat ggaacggct gtcaagaaca acttggcgat ccacagtgac    3060
ctgtcctatt ggattgaaag caggctcaat gatacgtgga agcttgaaag gcagttctg    3120 ggtgaagtca atcatgtac gtggcctgag acgcatacct tgtggggcga tggaatcctt    3180
gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc aggaactac ggtcaccctg agtgagagct gcggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgaccctt tcagttgggg ccttctggtc gtgttcttgg ccacccagga ggtccttcgc    3600
aagaggtgga cagccaagat cagcatgcca gctatactga ttgctctgct agtcctggtg    3660
tttgggggca ttacttacac tgatgtgtta cgctatgtca tcttggtggg ggcagctttc    3720
gcagaatcta ttcgggagg agacgtggta cacttggcgc tcatggcgac ctttaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
```

```
ttgatcaggg agaagaggag tgcagctgca aaaaagaaag gagcaagtct gctatgcttg    4140
gctctggcct caacaggact tttcaacccc atgatccttg ctgctggact gattgcatgt    4200
gatcccaacc gtaaacgcgg atggcccgca actgaagtga tgacagctgt cggcctaatg    4260
tttgccatcg tcggagggct ggcagagctt gacattgact ccatggccat tccaatgact    4320 atcgcgggc tcatgtttgc tgctttcgtg atttctggga aatcaacaga tatgtggatt    4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac cccctgggca    4560
atcttgccct cagtagttgg attttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa    4740
ggtgttttcc acacccttg gcatacaaca aaaggagccg ctttgatgag cggagagggc    4800
cgtctggacc catactgggg cagtgtcaag gaggatcgac tttgttacgg aggacccctgg   4860 aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa aacaaggagg    5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc tagggaggc ggcggcaata ttcatgacag ccaccccacc aggcacttca    5580
gatccattcc cagagtccaa ttcaccaatt tccgacttac agactgagat cccagatcga    5640
gcttggaact ccggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atggggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattta ccaaccagag cgtgagaagg tatataccat ggatgggga    6180 taccggctca gaggagaaga gaggaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaaacacaat ttagaagaca caacgaagt ggaagtcatc    6360 acgaagcttg gtgaaaggaa gattctgagg ccgcgctgga ttgacgccag ggtgtactcg    6420
```

```
gatcatcagg cactaaaggc gttcaaggac ttcgcctcgg gaaaacgttc tcagataggg      6480
ctcattgagg ttctgggaaa gatgcctgag cacttcatgg ggaagacatg ggaagcactt      6540
gacaccatgt acgttgtggc cactgcagag aaaggaggaa gagctcacag aatggccctg      6600
gaggaactgc cagatgctct tcagacaatt gccttgattg ccttattgag tgtgatgacc      6660
atggagtat tcttcctcct catgcagcgg aagggcattg aaagatagg tttgggaggc       6720
gctgttttgg gagtcgcgac ctttttctgt tggatggccg aagttccagg aacgaagatc      6780
gccggaatgt tgctgctctc ccttctcttg atgattgtgc taattcctga gccagagaag      6840
caacgttcgc agacagacaa ccagctagcc gtgttcctga tttgtgtcat gacccttgtg      6900
agcgcagtgg cagccaacga gatgggttgg ctagataaga ccaagagtga cataagcagt      6960
ttgtttgggc aaagaattga ggtcaaggag aattttagca tgggagagtt tcttctggac      7020
ttgaggccgg caacagcctg gtcactgtac gctgtgacaa cagcggtcct cactccactg      7080
ctaaagcatt tgatcacgtc agattacatc aacacctcat tgacctcaat aaacgttcag      7140
gcaagtgcac tattcacact cgcgcgaggc ttccccttcg tcgatgttgg agtgtcggct      7200
ctcctgctag cagccggatg ctggggacaa gtcaccctca ccgttacggt aacagcggca      7260
acactccttt tttgccacta tgcctacatg gttcccggtt ggcaagctga ggcaatgcgc      7320
tcagcccagc ggcggacagc ggccggaatc atgaagaacg ctgtagtgga tggcatcgtg      7380
gccacggacg tcccagaatt agagcgcacc acacccatca tgcagaagaa agttggacag      7440
atcatgctga tcttggtgtc tctagctgca gtagtagtga acccgtctgt gaagacagta      7500
cgagaagccg gaattttgat cacggccgca gcggtaacgc tttgggagaa tggagcaagc      7560
tctgtttgga acgcaacaac tgccatcgga ctctgccaca tcatgcgtgg gggttggttg      7620
tcatgtctat ccataacatg gacactcata aagaacatgg gaaaaccagg actaaaaaga      7680
ggtgggcaa aaggacgcac cttgggagag gtttggaaag aaagactcaa ccagatgaca      7740
aaagaagagt tcactaggta ccgcaaagag gccatcatcg aagtcgatcg ctcagcggca      7800
aaacacgcca ggaaagaagg caatgtcact ggagggcatc cagtctctag ggcacagca       7860
aaactgagat ggctggtcga acggaggttt ctcgaaccgg tcggaaaagt gattgacctt      7920
ggatgtggaa gaggcggctg tgttactat atggcaaccc aaaaaagagt ccaagaagtc       7980
agagggtaca caaagggcgg tcccggacat gaagagcccc aactagtgca aagttatgga      8040
tggaacattg tcaccatgaa gagtggagtg gatgtgttct acagaccttc tgagtgttgt      8100
gacacccctc tttgtgacat cggagagtcc tcgtcaagtg ctgaggttga agagcatagg      8160
acgattcggg tccttgaaat ggttgaggac tggctgcacc gagggccaag ggaattttgc      8220
gtgaaggtgc tctgcccta catgccgaaa gtcatagaga gatgagct gctccaacgc        8280
cggtatgggg ggggactggt tagaaaccca ctctcacgga actccacgca cgagatgtat      8340
tgggtgagtc gagcttcagg caatgtggta cattcagtga atatgaccag ccaggtgctc      8400
ctaggaagaa tggaaaaaag gacctggaag ggaccccaat acgaggaaga tgtaaacttg      8460
ggaagtggaa ccagggcggt gggaaaaccc ctgctcaact cggacaccag taaaatcaag      8520
aacaggattg aacgactcag gcgtgagtac agttcgacgt ggcaccacga tgagaaccac      8580
ccatatagaa cctggaacta tcacggcagt tatgatgtga agcccacagg ctccgccagt      8640
tcgctggtca atggagtggt caggctcctc tcaaaaccat gggacaccat cacgaatgtt      8700
accaccatgg ccatgactga cactactccc ttcgggcagc agcgagtgtt caaagagaag      8760
gtggacacga agctcctga accgccagaa ggagtgaagt acgtgctcaa cgagaccacc      8820
```

```
aactggttgt gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccgagagtt cggaaaggcc aagggaagca gagccatttg gttcatgtgg    9120
ctcggagctc gctttctgga gttcgaggct ctgggtttcc tcaatgaaga ccactggctt    9180
ggaagaaaga actcaggagg aggtgtcgag ggcttgggcc tccaaaaact gggttacatc    9240
ctgcgtgaag ttggcacccg gcctggggc aagatctatg ctgatgacac agctggctgg    9300
gacacccgca tcacgagagc tgacttggaa aatgaagcta aggtgcttga gttgcttgat    9360
ggggaacatc ggcgtcttgc cagggccatc attgagctca cctatcgtca caaagttgtg    9420
aaagtgatgc gcccggctgc tgatggaaga accgtcatgg atgttatctc tagagaagat    9480
cagaggggga gtggacaagt tgtcacctac gccctaaaca ctttcaccaa cctggccgtc    9540
cagctggtga ggatgatgga aggggaagga gtgattggcc cagatgatgt ggagaaactc    9600
acaaaaggga aggacccaa agtcaggacc tggctgtttg agaatgggga agaaagactc    9660
agccgcatgg ctgtcagtgg agatgactgt gtggtaaagc ccctggacga tcgctttgcc    9720
acctcgctcc acttcctcaa tgctatgtca aaggttcgca aagacatcca agagtggaaa    9780
ccgtcaactg gatggtatga ttggcagcag gttccatttt gctcaaacca tttcactgaa    9840
ttgatcatga aagatggaag aacactggtg gttccatgcc gaggacagga tgaattgta    9900 ggcagagctc gcatatctcc aggggccgga tggaacgtcc gcgacactgc ttgtctggct    9960
aagtcttatg cccagatgtg gctgcttctg tactttcaca gaagagacct gcggctcatg   10020
gccaacgcca tttgctccgc tgtccctgtg aattgggtcc ctaccggaag aaccacgtgg   10080
tccatccatg taggaggaga gtggatgaca acagaggaca tgttggaggt ctggaaccgt   10140
gtttggatag aggagaatga atggatggaa gacaaaaccc cagtggagaa atggagtgac   10200
gtcccatatt caggaaaacg agaggacatc tggtgtggca gcctgattgg cacaagagcc   10260
cgagccacgt gggcagaaaa catccaggtg gctatcaacc aagttagagc aatcatcgga   10320
gatgagaagt atgtggatta catgagttca ctaaagagat atgaagacac aactttggtt   10380
gaggacacag tactgtagat atttaatcaa ttgtaaatag acaatataag tatgcataaa   10440
agtgtagttt tatagtagta tttagtggtg ttagtgtaaa tagttaagaa aattttgagg   10500
agaaagtcag gccgggaagt tcccgccacc ggaagttgag tagacggtgc tgcctgcgac   10560
tcaaccccag gaggactggg tgaacaaagc cgcgaggtga tccatgtaag ccctcagaac   10620
cgtctcggaa ggaggacccc acatgttgta acttcaaagc ccaatgtcag accacgctac   10680
ggcgtgctac tctgcggaga gtgcagtctg cgatagtgcc ccaggaggac tgggttaaca   10740
aaggcaaacc aacgccccac gcggccctag ccctggtaat ggtgttaacc agggcgaagg   10800
gactagaggt tagaggagac cccgcggttt aaagtgcacg gcccagcctg gctgaagctg   10860
taggtcaggg gaaggactag aggttagtgg agacccgtg ccacaaaaca ccacaacaaa   10920
acagcatatt gacacctggg atagactagg agatcttctg ctctgcacaa ccagccacac   10980
ggcacagtgc gccgacaatg gtggctggtg gtgcgagaac acaggatct                11029
```

<210> SEQ ID NO 4
<211> LENGTH: 11029
<212> TYPE: DNA

<213> ORGANISM: West Nile virus

<400> SEQUENCE: 4

```
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agctcaaaac aaaagaaaag aggaggaaag     420
accggaattg cagtcatgat tggcctgatc gccagcgtag gagcagttac cctctctaac     480
ttccaaggga aggtgatgat gacggtaaat gctactgacg tcacagatgt catcacgatt     540
ccaacagctg ctggaaagaa cctatgcatt gtcagagcaa tggatgtggg atacatgtgc     600
gatgatacta tcacttatga atgcccagtg ctgtcggctg gtaatgatcc agaagacatt     660
gactgttggt gcacaaagtc agcagtctac gtcaggtatg aagatgcac caagacacgc     720
cactcaagac gcagtcggag gtcactgaca gtgcagacac acggagaaag cactctagcg     780
aacaagaagg gggcttggat ggacagcacc aaggccacaa gtatttggt aaaaacagaa     840
tcatggatct tgaggaaccc tggatatgcc ctggtggcag ccgtcattgg ttggatgctt     900
gggagcaaca ccatgcagag agttgtgttt atcgtgctat tgcttttggt ggccccagct     960
tacagcttca actgccttgg aatgagcaac agagacttct tggaaggagt gtctggagca    1020
acatgggtgg atttggttct cgaaggcgac agctgcgtga ctattatgtc taaggacaag    1080
cctaccatcg atgtgaagat gatgaatatg gaggcggcca acctggcaga ggtccgcagt    1140
tattgctatt tggctaccgt cagcgatctc tccaccaaag ctgcgtgccc gaccatggga    1200
gaagctcaca atgacaaacg tgctgaccca gcttttgtgt gcagacaagg agtggtggac    1260
aggggctggg gcaacggctg cggactattt ggcaaaggaa gcattgacac atgcgccaaa    1320
tttgcctgct ctaccaaggc aataggaaga accatcttga agagaatat caagtacgaa    1380
gtggccattt tgtccatgg accaactact gtggagtcgc acggaaacta ctccacacag    1440
gctggagcca ctcaggcagg agattcagc atcactcctg cggcgccttc atacacacta    1500
aagcttggag aatatggaga ggtgacagtg gactgtgaac cacggtcagg gattgacacc    1560
aatgcatact acgtgatgac tgttggaaca aagacgttct ggtccatcg tgagtggttc    1620
atggacctca acctcccttg gagcagtgct ggaagtactg tgtggaggaa cagagagacg    1680
ttaatggagt tgaggaacc acacgccacg aagcagtctg tgatagcatt gggctcacaa    1740
gagggagctc tgcatcaagc tttggctgga gccattcctg tggaattttc aagcaacact    1800
gtcaagttga cgtcgggtca tttgaagtgt agagtgaaga tggaaaaatt acagttgaag    1860
ggaacaacct atgcgtcgtg ttcaaaggct ttcaagtttc ttgggactcc cgcagacaca    1920
ggtcacggca ctgtggtgtt ggaattgcag tacactggca cggatggacc ttgcaaagtt    1980
cctatctcgt cagtggcttc attgaacgac ctaacgccag tgggcagatt ggtcactgtc    2040
aaccctttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag agacacagc ttgggactttt ggatcagttg gaggggtgtt cacctcagtt    2280
```

```
gggaaggctg tccatcaagt gttcggagga gcattccgct cactgttcgg aggcatgtcc  2340
tggataacgc aaggattgct gggggctctc ctgttgtgga tgggcatcaa tgctcgtgat  2400
aggtccatag ctctcacgtt tctcgcagtt ggaggagttc tgctcttcct ctccgtgaac  2460
gtgcatgctg acactgggtg tgccatagac atcagccggc aagagctgag atgtggaagt  2520
ggagtgttca tacacaatga tgtggaggct tggatggacc ggtacaagta ttaccctgaa  2580
acgccacaag gcctagccaa gatcattcag aaagctcata aggaaggagt gtgcggtcta  2640
cgatcagttt ccagattgga gcatcaaatg tgggaagcag tgaaggacga gctgaacact  2700
cttttgaagg agaatggtgt ggaccttagt gtcgtggttg agaaacagga gggaatgtac  2760
aagtcagcac ctaaacgcct caccgccacc acggaaaaat tggaaattgg ctggaaggcc  2820
tggggaaaga gtatttttatt tgcaccagaa ctcgccaaca cacctttgt ggttgatggt  2880 ccggagacca aggaatgtcc gactcagaat cgcgcttgga atagcttaga agtgaggat  2940 tttggatttg gtctcaccag cactcggatg ttcctgaagg tcagagagag caacacaact  3000
gaatgtgact cgaagatcat ggaacggct gtcaagaaca acttggcgat ccacagtgac  3060
ctgtcctatt ggattgaaag caggctcaat gatacgtgga agcttgaaag ggcagttctg  3120
ggtgaagtca atcatgtac gtggcctgag acgcatacct tgtggggcga tggaatcctt  3180
gagagtgact tgataatacc agtcacactg gcgggaccac gaagcaatca caatcggaga  3240
cctgggtaca agacacaaaa ccagggccca tgggacgaag gccgggtaga gattgacttc  3300
gattactgcc caggaactac ggtcaccctg agtgagagct cgggacaccg tggacctgcc  3360
actcgcacca ccacagagag cggaaagttg ataacagatt ggtgctgcag gagctgcacc  3420
ttaccaccac tgcgctacca aactgacagc ggctgttggt atggtatgga gatcagacca  3480
cagagacatg atgaaaagac cctcgtgcag tcacaagtga atgcttataa tgctgatatg  3540 attgacccctt ttcagttggg ccttctggtc gtgttcttgg ccacccagga ggtccttcgc  3600
aagaggtgga cagccaagat cagcatgcca gctatactga ttgctctgct agtcctggtg  3660
tttgggggca ttacttacac tgatgtgtta cgctatgtca tcttggtggg ggcagctttc  3720
gcagaatcta attcgggagg agacgtggta cacttggcgc tcatggcgac ctttaagata  3780
caaccagtgt ttatggtggc atcgtttctc aaagcgagat ggaccaacca ggagaacatt  3840
ttgttgatgt tggcggctgt tttctttcaa atggcttatc acgatgcccg ccaaattctg  3900
ctctgggaga tccctgatgt gttgaattca ctggcggtag cttggatgat actgagagcc  3960
ataacattca caacgacatc aaacgtggtt gttccgctgc tagccctgct aacacccggg  4020
ctgagatgct tgaatctgga tgtgtacagg atactgctgt tgatggtcgg aataggcagc  4080
ttgatcaggg agaagaggag tgcagctgca aaaaagaaag gagcaagtct gctatgcttg  4140
gctctggcct caacaggact tttcaacccc atgatccttg ctgctggact gattgcatgt  4200
gatcccaacc gtaaacgcgg atggcccgca actgaagtga tgacagctgt cggcctaatg  4260
tttgccatcg tcgagggct ggcagagctt gacattgact ccatggccat tccaatgact  4320 atcgcgggc tcatgtttgc tgctttcgtg atttctggga aatcaacaga tatgtggatt  4380
gagagaacgg cggacatttc ctgggaaagt gatgcagaaa ttacaggctc gagcgaaaga  4440
gttgatgtgc ggcttgatga tgatggaaac ttccagctca tgaatgatcc aggagcacct  4500
tggaagatat ggatgctcag aatggtctgt ctcgcgatta gtgcgtacac ccctgggca  4560 atcttgccct cagtagttgg attttggata actctccaat acacaaagag aggaggcgtg  4620
```

```
ttgtgggaca ctccctcacc aaaggagtac aaaaaggggg acacgaccac cggcgtctac    4680
aggatcatga ctcgtgggct gctcggcagt tatcaagcag gagcgggcgt gatggttgaa    4740
ggtgttttcc acacccttg gcatacaaca aaaggagccg ctttgatgag cggagagggc    4800
cgtctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga cttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg cgccggtaa acaaggagg    5220 attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400 gctacccta cccacaggct gatgtctcct cacaggtgc cgaactacaa cctgttcgtg    5460
atggatgagg ctcatttcac cgacccagct agcattgcag caagaggtta catttccaca    5520
aaggtcgagc tagggggagc ggcggcaata ttcatgacag ccaccccacc aggcacttca    5580
gatccattcc cagagtccaa ttcaccaatt tccgacttac agactgagat cccagatcga    5640
gcttggaact ccggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaatttta ccaaccagag cgtgagaagg tatataccat ggatgggaa    6180 taccggctca gaggagaaga gaggaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg gtgaaaggaa gattctgagg ccgcgctgga ttgacgccag ggtgtactcg    6420
gatcatcagg cactaaaggc gttcaaggac ttcgcctcgg gaaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggcctg    6600 gaggaactgc cagatgctct tcagacaatt gccttgattg ccttattgag tgtgatgacc    6660
atgggagtat tcttcctcct catgcagcgg aagggcattg aaagataggt ttgggaggc    6720 gctgttttgg gagtcgcgac cttttctgt tggatggccg aagttccagg aacgaagatc    6780
gccggaatgt tgctgctctc ccttctcttg atgattgtgc taattcctga gccagagaag    6840
caacgttcgc agacagacaa ccagctagcc gtgttcctga tttgtgtcat gaccccttgtg    6900 agcgcagtgc cagccaacga gatgggttgg ctagataaga ccaagagtga cataagcagt    6960
ttgtttgggc aaagaattga ggtcaaggag aattttagca tgggagagtt tcttctggac    7020
```

```
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg aattttgat cacggccgca gcggtaacgc tttgggagaa tggagcaagc    7560
tctgtttgga acgcaacaac tgccatcgga ctctgccaca tcatgcgtgg gggttggttg    7620
tcatgtctat ccataacatg gacactcata agaacatgg gaaaaccagg actaaaaaga    7680
ggtggggcaa aaggacgcac cttgggagag gtttggaaag aaagactcaa ccagatgaca    7740
aaagaagagt tcactaggta ccgcaaagag gccatcatcg aagtcgatcg ctcagcggca    7800
aaacacgcca ggaaagaagg caatgtcact ggagggcatc cagtctctag gggcacagca    7860
aaactgagat ggctggtcga acggaggttt ctcgaaccgg tcggaaaagt gattgacctt    7920
ggatgtggaa gaggcggctg tgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtggagtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgccccta catgccgaaa gtcatagaga agatggagct gctccaactc    8280
cggtatgggg ggggactggt tagaaaccca ctctcacgga actccacgca cgagatgtat    8340
tgggtgagtc gagcttcagg caatgtggta cattcagtga atatgaccag ccaggtgctc    8400
ctaggaagaa tggaaaaaag gacctggaag ggaccccaat acgaggaaga tgtaaacttg    8460
ggaagtggaa ccagggcggt gggaaaaccc ctgctcaact cggacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atggagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccgagagtt cggaaaggcc aagggaagca gagccatttg gttcatgtgg    9120
ctcgagctc gctttctgga gttcgaggct ctgggtttcc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gttgcttgat    9360
```

-continued

```
ggggaacatc ggcgtcttgc cagggccatc attgagctca cctatcgtca caaagttgtg    9420
aaagtgatgc gcccggctgc tgatggaaga accgtcatgg atgttatctc tagagaagat    9480
cagaggggga gtggacaagt tgtcacctac gccctaaaca cttttcaccaa cctggccgtc   9540 cagctggtga ggatgatgga aggggaagga gtgattggcc cagatgatgt ggagaaactc    9600
acaaaaggga aggacccaa agtcaggacc tggctgtttg agaatgggga agaaagactc    9660
agccgcatgg ctgtcagtgg agatgactgt gtggtaaagc ccctggacga tcgctttgcc    9720
acctcgctcc acttcctcaa tgatatgtca aaggttcgca agacatcca agagtggaaa    9780 ccgtcaactg gatggtatga ttggcagcag gttccatttt gctcaaacca tttcactgaa    9840
ttgatcatga agatggaag aacactggtg gttccatgcc gaggacagga tgaattggta    9900
ggcagagctc gcatatctcc aggggccgga tggaacgtcc gcgacactgc ttgtctggct    9960
aagtcttatg cccagatgtg gctgcttctg tactttcaca agagacct gcggctcatg    10020 gccaacgcca tttgctccgc tgtccctgtg aattgggtcc ctaccggaag aaccacgtgg    10080
tccatccatg taggaggaga gtggatgaca acagaggaca tgttggaggt ctggaaccgt    10140
gtttggatag aggagaatga atggatgaa acaaaaccc cagtggagaa atggagtgac    10200
gtcccatatt caggaaaacg agaggacatc tggtgtggca gcctgattgg cacaagagcc    10260
cgagccacgt gggcagaaaa catccaggtg gctatcaacc aagttagagc aatcatcgga    10320
gatgagaagt atgtggatta catgagttca ctaaagagat atgaagacac aacttttggtt    10380 gaggacacag tactgtagat atttaatcaa ttgtaaatag acaatataag tatgcataaa    10440
agtgtagttt tatagtagta tttagtggtg ttagtgtaaa tagttaagaa aattttgagg    10500
agaaagtcag gccgggaagt tcccgccacc ggaagttgag tagacggtgc tgcctgcgac    10560
tcaaccccag gaggactggg tgaacaaagc cgcgaggtga tccatgtaag ccctcagaac    10620
cgtctcggaa ggaggacccc acatgttgta acttcaaagc ccaatgtcag accacgctac    10680
ggcgtgctac tctgcggaga gtgcagtctg cgatagtgcc ccaggaggac tgggttaaca    10740
aaggcaaacc aacgccccac gcggccctag ccctggtaat ggtgttaacc agggcgaagg    10800
gactagaggt tagaggagac cccgcggttt aaagtgcacg gcccagcctg ctgaagctg    10860 taggtcaggg gaaggactag aggttagtgg agacccgtg ccacaaaaca ccacaacaaa    10920
acagcatatt gacacctggg atagactagg agatcttctg ctctgcacaa ccagccacac    10980
ggcacagtgc gccgacaatt gtggctggtg gtgcgagaac acaggatct             11029
```

<210> SEQ ID NO 5
<211> LENGTH: 11029
<212> TYPE: DNA
<213> ORGANISM: West Nile virus

<400> SEQUENCE: 5

```
agtagttcgc ctgtgtgagc tgacaaactt agtagtgttt gtgaggatta caacaatta    60 acacagtgcg agctgtttct tagcacgaag atctcgatgt ctaagaaacc aggagggccc   120
ggcaagagcc gggctgtcaa tatgctaaaa cgcggaatgc cccgcgtgtt gtccttgatt    180
ggactgaaga gggctatgtt gagcctgatc gacggcaagg ggccaatacg atttgtgttg    240
gctctcttgg cgttcttcag gttcacagca attgctccga cccgagcagt gctggatcga    300
tggagaggtg tgaacaaaca aacagcgatg aaacaccttc tgagttttaa gaaggaacta    360
gggaccttga ccagtgctat caatcggcgg agctcaaaac aaaagaaaag aggaggaaag    420
accggaattg cagtcatgat tggcctgatc gccagcgtag gagcagttac cctctctaac    480
```

```
ttccaaggga aggtgatgat gacggtaaat gctactgacg tcacagatgt catcacgatt    540
ccaacagctg ctggaaagaa cctatgcatt gtcagagcaa tggatgtggg atacatgtgc    600
gatgatacta tcacttatga atgcccagtg ctgtcggctg gtaatgatcc agaagacatt    660
gactgttggt gcacaaagtc agcagtctac gtcaggtatg aagatgcac caagacacgc     720 cactcaagac gcagtcggag gtcactgaca gtgcagacac acggagaaag cactctagcg    780
aacaagaagg gggcttggat ggacagcacc aaggccacaa ggtatttggt aaaaacagaa    840
tcatggatct tgaggaaccc tggatatgcc ctggtggcag ccgtcattgg ttggatgctt    900
gggagcaaca ccatgcagag agttgtgttt gtcgtgctat tgcttttggt ggccccagct    960
tacagcttca actgccttgg aatgagcaac agagacttct ggaaggagt gtctggagca    1020 acatgggtgg atttggttct cgaaggcgac agctgcgtga ctatcatgtc taaggacaag    1080
cctaccatcg atgtgaagat gatgaatatg gaggcggcca acctggcaga ggtccgcagt    1140
tattgctatt tggctaccgt cagcgatctc tccaccaaag ctgcgtgccc gaccatggga    1200
gaagctcaca atgacaaacg tgctgaccca gcttttgtgt gcagacaagg agtggtggac    1260
aggggctggg gcaacggctg cggactattt ggcaaaggaa gcattgacac atgcgccaaa    1320
tttgcctgct ctaccaaggc aataggaaga accatcttga aagagaatat caagtacgaa    1380
gtggccattt ttgtccatgg accaactact gtggagtcgc acggaaacta ctccacacag    1440
gctggagcca tcaggcagg gagattcagc atcactcctg cggcgccttc atacacacta    1500
aagcttggag aatatggaga ggtgacagtg gactgtgaac cacggtcagg gattgacacc    1560
aatgcatact acgtgatgac tgttggaaca aagacgttct tggtccatcg tgagtggttc    1620
atggacctca acctcccttg gagcagtgct ggaagtactg tgtggaggaa cagagagacg    1680
ttaatggagt ttgaggaacc acacgccacg aagcagtctg tgatagcatt gggctcacaa    1740
gagggagctc tgcatcaagc tttggctgga gccattcctg tggaatttc aagcaacact    1800 gtcaagttga cgtcgggtca tttgaagtgt agagtgaaga tggaaaaatt gcagttgaag    1860
ggaacaacct atgcgtctg ttcaaaggct ttcaagtttc ttgggactcc cgcagacaca    1920
ggtcacggca ctgtggtgtt ggaattgcag tacactggca cggatggacc ttgcaaagtt    1980
cccatctcgt cagtggcttc attgaacgac ctaacgccag tgggcagatt ggtcactgtc    2040
aacccttttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag agacacagc ttgggacttt ggatcagttg gagggggtgtt cacctcagtt    2280 gggaaggctg tccatcaagt gttcggagga gcattccgct cactgttcgg aggcatgtcc    2340
tggataacgc aaggattgct gggggctctc ctgttgtgga tgggcatcaa tgctcgtgat    2400
aggtccatag ctctcacgtt tctcgcagtt ggaggagttc tgctcttcct ctccgtgaac    2460
gtgcatgctg acactgggtg tgccatagac atcagccggc aagagctgag atgtggaagt    2520
ggagtgttca tacacaatga tgtggaggct tggatggacc ggtacaagta ctaccctgaa    2580
acgccacaag gcctagccaa gatcattcag aaagctcata aggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
```

```
tggggaaaga gtattttatt tgcaccagaa ctcgccaaca acacctttgt ggttgatggt   2880
ccggagacca aggaatgtcc gactcagaat cgcgcttgga atagcttaga agtggaggat   2940
tttggatttg gtctcaccag cactcggatg ttcctgaagg tcagagagag caacacaact   3000
gaatgtgact cgaagatcat tggaacggct gtcaagaaca acttggcgat ccacagtgac   3060
ctgtcctatt ggattgaaag caggctcaat gatacgtgga agcttgaaag ggcagttctg   3120
ggtgaagtca atcatgtac gtggcctgag acgcatacct tgtggggcga tggaatcctt    3180
gagagtgact tgataatacc agtcacactg gcgggaccac gaagcaatca caatcggaga   3240
cctgggtaca agacacaaaa ccaaggccca tgggacgaag gccgggtaga gattgacttc   3300
gattactgcc caggaactac ggtcaccctg agtgagagct gcggacaccg tggacctgcc   3360
actcgcacca ccacagagag cggaaagttg ataacagatt ggtgctgcag gagctgcacc   3420
ttaccaccac tgcgctacca aactgacagc ggctgttggt atggtatgga gatcagacca   3480
cagagacatg atgaaaagac cctcgtgcag tcacaagtga atgcttataa tgctgatatg   3540
attgaccctt ttcagttggg ccttctggtc gtgttcttgg ccacccagga ggtccttcgc   3600
aagaggtgga cagccaagat cagcatgcca gctatactga ttgctctgct agtcctggtg   3660
tttgggggca ttacttacac tgatgtgtta cgctatgtca tcttggtggg ggcagctttc   3720
gcagaatcta attcgggagg agacgtggta cacttggcgc tcatggcgac cttcaagata   3780
caaccagtgt ttatggtggc atcgtttctc aaagcgagat ggaccaacca ggagaacatt   3840
ttgttgatgt tggcggctgt tttctttcaa atggcttatc acgatgcccg ccaaattctg   3900
ctctgggaga tccctgatgt gttgaattca ctggcggtag cttggatgat actgagagcc   3960
ataacattca aacgacatc aaacgtggtt gttccgctgc tagccctgct aacacccggg   4020
ctgagatgct tgaatctgga tgtgtacagg atactgctgt tgatggtcgg aataggcagc   4080
ttgatcaggg agaagaggag tgcagctgca aaaaagaaag gagcaagtct gctatgcttg   4140
gctctggcct caacaggact tttcaacccc atgatccttg ctgctggact gattgcatgt   4200
gatcccaacc gtaaacgcgg atggcccgca actgaagtga tgcagctgt cggcctaatg   4260
tttgccatcg tcggagggct ggcagagctt gacattgact ccatggccat tccaatgact   4320
atcgcgggc tcatgtttgc tgctttcgtg atttctggga atcaacaga tatgtggatt   4380
gagagaacgg cggacatttc ctgggaaagt gatgcagaaa ttacaggctc gagcgaaaga   4440
gttgatgtgc ggcttgatga tgatggaaac ttccagctca tgaatgatcc aggagcacct   4500
tggaagatat ggatgctcag aatggtctgt ctcgcgatta gtgcgtacac ccctgggca    4560
atcttgccct cagtagttgg atttggata actctccagt acacaaagag aggaggcgtg   4620
ttgtgggaca ctcccctcacc aaaggagtac aaaaagggg acacgaccac cggcgtctac   4680
aggatcatga ctcgtgggct gctcggcagt tatcaagcag gagcgggcgt gatggttgaa   4740
ggtgttttcc acacccttg gcatacaaca aaggagccg ctttgatgag cggagagggc    4800
cgtctggacc catactgggg cagtgtcaag gaggatcgac tttgttacgg aggaccctgg   4860
aaattgcagc acaagtggaa cgggcaggat gaggtgcaga tgattgtggt ggaacctggc   4920
aagaacgtta agaacgtcca gacgaaacca ggggtgttca aaacacctga aggagaaatc   4980
ggggccgtga ctttggactt ccccactgga acatcaggct caccaatagt ggacaaaaac   5040
ggtgatgtga ttgggcttta tggcaatgga gtcataatgc caacggctc atacataagc    5100
gcgatagtgc agggtgaaag gatggatgag ccaatcccag ccggattcga tcctgagatg   5160
ctgaggaaaa aacagatcac tgtactggac ctccatcccg gcgccggtaa aacaaggagg   5220
```

```
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagc tcatttcac cgacccagct agcattgcag caagaggtta catttccaca    5520
aaggtcgagc taggggaggc ggcggcaata ttcatgacag ccaccccacc aggcacttca    5580
gatccattcc caaagtccaa ttcaccaatt tccgacttac agactgagat cccggatcga    5640
gcttggaact ctggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg    5820
gactttgtta tcacaacaga catatctgaa atgggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaatttta ccaaccagag cgtgagaagg tatataccat ggatgggaa    6180
taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg tgaaaggaa gattctgagg ccgcgctgga ttgacgccag ggtgtactcg    6420
gatcatcagg cactaaaggc gttcaaggac ttcgcctcgg gaaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac cttttttctgt tggatggctg aagttccagg aacgaagatc    6780
gccggaatgt tgctgctctc ccttctcttg atgattgtgc taattcctga gccagagaag    6840
caacgttcgc agacagacaa ccagctagcc atgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttagca tgggagagtt tcttctggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctgggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcattgtg    7380
gccacggacg tcccagaatt agagcgcacc acacccatca tgcagaagaa agttggacag    7440
atcatgctga tctcttggtgtc tctagctgca gtagtagtga acccgtctgt gaagacagta    7500
cgagaagccg gaatttttgat cacggccgca gcggtgacgc tttgggagaa tggagcaagc    7560
```

```
tctgtttgga acgcaacaac tgccatcgga ctctgccaca tcatgcgtgg gggttggttg   7620
tcatgtctat ccataacatg gacactcata agaacatgg aaaaaccagg actaaaaga    7680 ggtggggcaa aaggacgcac cttgggagag gtttggaaag aaagactcaa ccagatgaca   7740
aaagaagagt tcactaggta ccgcaaagag gccatcatcg aagtcgatcg ctcagcggca   7800
aaacacgcta ggaaagaagg caatgtcact ggagggcatc cagtctctag ggcacagca    7860 aaactgagat ggctggtcga acggaggttt ctcgaaccgg tcggaaaagt gattgacctt   7920
ggatgtggaa gaggcggctg tgttactat atggcaaccc aaaaagagt ccaagaagtc    7980 agagggtaca caaagggcgg tcccggacat gaagagcccc aactagtgca aagttatgga   8040
tggaacattg tcaccatgaa gagtggagtg gatgtgttct acagaccttc tgagtgttgt   8100
gacaccctcc tttgtgacat cggagagtcc tcgtcaagtg ctgaggttga agagcatagg   8160
acgattcggg tccttgaaat ggttgaggac tggctgcacc gagggccaag ggaattttgc   8220
gtgaaggtgc tctgcccta catgccgaaa gtcatagaga gatggagct gctccaacgc    8280 cggtatgggg gggactggt cagaaaccca ctctcacgga attccacgca cgagatgtat   8340
tgggtgagtc gagcttcagg caatgtggta cattcagtga atatgaccag ccaggtgctc   8400
ctaggaagaa tggaaaaaag gacctggaag ggaccccaat acgaggaaga tgtaaacttg   8460
ggaagtggaa ccagggcggt gggaaaaccc ctgctcaact cagacaccag taaaatcaag   8520
aacaggattg aacgactcag gcgtgagtac agttcgacgt ggcaccacga tgagaaccac   8580
ccatatagaa cctggaacta tcacggcagt tatgatgtga agcccacagg ctccgccagt   8640
tcgctggtca atggagtggt caggctcctc tcaaaaccat gggacaccat cacgaatgtt   8700
accaccatgg ccatgactga cactactccc ttcgggcagc agcgagtgtt caaagagaag   8760
gtggacacga aagctcctga accgccagaa ggagtgaagt acgtgctcaa cgagaccacc   8820
aactggttgt gggcgttttt ggccagagaa aaacgtccca gaatgtgctc tcgagaggaa   8880
ttcataagaa aggtcaacag caatgcagct ttgggtgcca tgtttgaaga gcagaatcaa   8940
tggaggagcg ccagagaagc agttgaagat ccaaaattt gggagatggt ggatgaggag   9000
cgcgaggcac atctgcgggg ggaatgtcac acttgcattt acaacatgat gggaaagaga   9060
gagaaaaaac ccgagagtt cggaaaggcc aagggaagca gagccatttg gttcatgtgg   9120
ctcggagctc gctttctgga gttcgaggct ctggttttc tcaatgaaga ccactggctt   9180
ggaagaaaga actcaggagg aggtgtcgag ggcttgggcc tccaaaagct gggttacatc   9240
ctgcgtgaag ttggcacccg gcctgggggc aagatctatg ctgatgacac agctggctgg   9300
gacacccgca tcacgagagc tgacttggaa aatgaagcta aggtgcttga gttgcttgat   9360
ggggaacatc ggcgtcttgc cagggccatc attgagctca cctatcgtca caaagttgtg   9420
aaagtgatgc gcccggctgc tgatggaaga accgtcatgg atgttatctc cagagaagat   9480
cagaggggga gtggacaagt tgtcacctac gcccctaaaca cttccaccaa cctgtccgtc   9540
cagctggtga ggatgatgga agggaagga gtgattggcc cagatgatgt ggagaaactc   9600
acaaagggga aaggacccaa agtcaggacc tggctgtttg agaatgggga agaaagactc   9660
agccgcatgg ctgtcagtgg agatgactgt gtggtaaagc ccctggacga tcgctttgcc   9720
acctcgctcc acttcctcaa tgctatgtca aaggttcgca aggacatcca agagtggaaa   9780
ccgtcaactg gatggtatga ttggcagcag gttccatttt gctcaaacca tttcactgaa   9840
ttgatcatga aagatggaag aacactggtg gttccatgcc gaggacagga tgaattggta   9900
ggcagagctc gcatatctcc aggagccgga tggaacgtcc gcgacactgc ttgtctggct   9960
```

-continued

| | |
|---|---|
| aagtcttatg cccagatgtg gctgcttctg tacttccaca gaagagacct gcggctcatg | 10020 |
| gccaacgcca tttgctccgc tgtccctgtg aattgggtcc ctaccggaag aaccacgtgg | 10080 |
| tccatccatg caggaggaga gtggatgaca acagaggaca tgttggaggt ctggaaccgt | 10140 |
| gtttggatag aggagaatga atggatggaa gacaaaaccc cagtggagaa atggagtgac | 10200 |
| gtcccatatt caggaaaacg agaggacatc tggtgtggca gcctgattgg cacaagagcc | 10260 |
| cgagccacgt gggcagaaaa catccaggtg gctatcaacc aagtcagagc aatcatcgga | 10320 |
| gatgagaagt atgtggatta catgagttca ctaaagagat atgaagacac aactttggtt | 10380 |
| gaggacacag tactgtagat atttaattaa ttgtaaatag acaatataag tatgcataaa | 10440 |
| agtgtagttt tatagtagta tttagtggtg ttagtgtaaa tagttaagaa aattttgagg | 10500 |
| agaaagtcag gccgggaagt tcccgccacc ggaagttgag tagacggtgc tgcctgcgac | 10560 |
| tcaaccccag gaggactggg tgaacaaagc cgcgaagtga tccatgtaag ccctcagaac | 10620 |
| cgtctcggaa ggaggacccc acatgttgta acttcaaagc ccaatgtcag accacgctac | 10680 |
| ggcgtgctac tctgcggaga gtgcagtctg cgatagtgcc ccaggaggac tgggttaaca | 10740 |
| aaggcaaacc aacgccccac gcggccctag ccccggtaat ggtgttaacc agggcgaaag | 10800 |
| gactagaggt tagaggagac cccgcggttt aaagtgcacg gcccagcctg gctgaagctg | 10860 |
| taggtcaggg gaaggactag aggttagtgg agaccccgtg ccacaaaaca ccacaacaaa | 10920 |
| acagcatatt gacacctggg atagactagg agatcttctg ctctgcacaa ccagccacac | 10980 |
| ggcacagtgc gccgacaatg gtggctggtg gtgcgagaac acaggatct | 11029 |

<210> SEQ ID NO 6
<211> LENGTH: 11029
<212> TYPE: DNA
<213> ORGANISM: West Nile virus

<400> SEQUENCE: 6

| | |
|---|---|
| agtagttcgc ctgtgtgagc tgacaaactt agtagtgttt gtgaggatta acaacaatta | 60 |
| acacagtgcg agctgtttct tagcacgaag atctcgatgt ctaagaaacc aggagggccc | 120 |
| ggcaagagcc gggctgtcaa tatgctaaaa cgcggaatgc cccgcgtgtt gtccttgatt | 180 |
| ggactgaaga gggctatgtt gagcctgatc gacggcaagg ggccaatacg atttgtgttg | 240 |
| gctctcttgg cgttcttcag gttcacagca attgctccga cccgagcagt gctggatcga | 300 |
| tggagaggtg tgaacaaaca aacagcgatg aaacaccttc tgagttttaa gaaggaacta | 360 |
| gggaccttga ccagtgctat caatcggcgg agctcaaaac aaaagaaaag aggaggaaag | 420 |
| accggaattg cagtcatgat tggcctgatc gccagcgtag gagcagttac cctctctgac | 480 |
| ttccaaggga aggtgatgat gacggtaaat gctactgacg tcacagatgt catcacgatt | 540 |
| ccaacagctg ctggaaagaa cctatgcatt gtcagagcaa tggatgtggg atacatgtgc | 600 |
| gatgatacta tcacttatga atgcccagtg ctgtcggctg gtaatgatcc agaagacatt | 660 |
| gactgttggt gcacaaagtc agcagtctac gtcaggtatg aagatgcac caagacacgc | 720 |
| cactcaagac gcagtcggag gtcactgaca gtgcagacac acggagaaag cactctagcg | 780 |
| aacaagaagg gggcttggat ggacagcacc aaggccacaa gtatttggt aaaaacagaa | 840 |
| tcatggatct tgaggaaccc tggatatgcc ctggtggcag ccgtcattgg ttggatgctt | 900 |
| gggagcaaca ccatgcagag agttgtgttt gtcgtgctat tgcttttggt ggccccagct | 960 |
| tacagcttca actgccttgg aatgagcaac agagacttct tggaaggagt gtctggagca | 1020 |

```
acatgggtgg atttggttct cgaaggcgac agctgcgtga ctatcatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc gaccatggga   1200
gaagctcaca atgacaaacg tgctgaccca gcttttgtgt gcagacaagg agtggtggac   1260
aggggctggg gcaacggctg cggactattt ggcaaaggaa gcattgacac atgcgccaaa   1320
tttgcctgct ctaccaaggc aataggaaga accatcttga aagagaatat caagtacgaa   1380
gtggccattt ttgtccatgg accaactact gtggagtcgc acggaaacta ctccacacag   1440
gctggagcca ctcaggcagg gagattcagc atcactcctg cggcgccttc atacacacta   1500
aagcttggag aatatggaga agtgacagtg gactgtgaac cacggtcagg gattgacacc   1560
aatgcatact acgtgatgac tgttggaaca aagacgttct tggtccatcg tgagtggttc   1620
atggacctca acctcccttg gagcagtgct ggaagtactg tgtggaggaa cagagagacg   1680
ttaatggagt tgaggaacc acacgccacg aagcagtctg tatagcatt gggctcacaa   1740
gagggagctc tgcatcaagc tttggctgga gccattcctg tggaattttc aagcaacact   1800
gtcaagttga cgtcgggtca tttgaagtgt agagtgaaga tggaaaaatt gcagttgaag   1860
ggaacaacct atggcgtctg ttcaaaggct ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tgggcagatt ggtcactgtc   2040
aacccttttg tttcagtggc cacgccaac gctaaggtcc tgattgaatt ggaaccaccc   2100
tttggagact catacatagt ggtgggcaga ggagaacaac agatcaatca ccattggcac   2160
aagtctggaa gcagcattgg caaagccttt acaaccaccc tcaaaggagc gcagagacta   2220
gccgctctag agacacagc ttgggacttt ggatcagttg aggggtgtt cacctcagtt   2280
gggaaggctg tccatcaagt gttcggagga gcattccgct cactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcatgctg acactgggtg tgccatagac atcagccggc aagagctgag atgtggaagt   2520
ggagtgttca tacacaatga tgtggaggct tggatggacc ggtacaagta ttaccctgaa   2580
acgccacaag gcctagccaa gatcattcag aaagctcata aggaaggagt gtgcggtcta   2640
cgatcagttt ccagactgga gcatcaaatg tgggaagcag tgaaggacga gctgaacact   2700
cttttgaagg agaatggtgt ggaccttagt gtcgtggttg agaaacagga gggaatgtac   2760
aagtcagcac ctaaacgcct caccgccacc acggaaaaat tggaaattgg ctggaaggcc   2820
tggggaaaga gtatttatt tgcaccagag ctcgccaaca acacctttgt ggttgatggt   2880
ccggagacca aggaatgtcc gactcagaat cgcgcttgga atagcttaga agtggaggat   2940
tttgatttg gtctcaccag cactcggatg ttcctgaagg tcagagagag caacacaact   3000
gaatgtgact cgaagatcat tggaacggct gtcaagaaca acttggcgat ccacagtgac   3060
ctgtcctatt ggattgaaag caggctcaat gatacgtgga agcttgaaag gcagttctg   3120
ggtgaagtca aatcatgtac gtggcctgag acgcatacct tgtggggcga tggaatcctt   3180
gagagtgact tgataatacc agtcacactg gcgggaccac gaagcaatca caatcggaga   3240
cctgggtaca agacacaaaa ccagggccca tgggacgaag gccgggtaga gattgacttc   3300
gattactgcc caggaactac ggtcaccctg agtgagagct cgcgacaccg tggacctgcc   3360
actcgcacca ctacagagag cggaaagttg ataacagatt ggtgctgcag gagctgcacc   3420
```

```
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgacccct ttcagttggg ccttctggtc gtgttcttgg ccacccagga ggtccttcgc    3600
aagaggtgga cagccaagat cagcatgcca gctatactga ttgctctgct agtcctggtg    3660
tttggggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagctgca aaaagaaag gagcaagtct gctatgcttg    4140
gctctggcct caacaggact tttcaacccc atgatccttg ctgctggact gattgcatgt    4200
gatcccaacc gtaaacgcgg atggcccgca actgaagtga tgacagctgt cggcctaatg    4260
tttgccatcg tcggagggct ggcagagctt gacattgact ccatggccat tccaatgact    4320
atcgcggggc tcatgtttgc tgcttttcgtg atttctggga aatcaacaga tatgtggatt    4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac cccctgggca    4560
atcttgccct cagtagttgg atttggata actctccaat acacaaagag aggaggcgtg    4620
ttgtgggaca ctccctcacc aaaggagtac aaaaaggggg acacgaccac cggcgtctac    4680
aggatcatga ctcgtgggct gctcggcagt tatcaagcag gagcgggcgt gatggttgaa    4740
ggtgttttcc acacccttg gcatacaaca aaaggagccg ctttgatgag cggagagggc    4800
cgtctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggctta tggcaatgga gtcataatgc caacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa acaaggagg    5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc tagggggaggc ggcggcaata ttcatgacag ccacccccac aggcacttca    5580
gatccattcc cagtccaa ttcaccaatt tccgacttac agactgagat cccggatcga    5640
gcttggaact ctggatacga atggatcaca gaatacaccg ggaagacggt ttggtttgtg    5700
cctagtgtca agatggggaa tgagattgcc ctttgcctac aacgtgctgg aaagaaagta    5760
```

```
gtccaattga acagaaagtc gtacgagacg gagtacccaa aatgtaagaa cgatgattgg   5820
gactttgtta tcacaacaga catatctgaa atggggggcta acttcaaggc gagcagggtg   5880
attgacagcc ggaagagtgt gaaaccaacc atcataacag aaggagaagg gagagtgatc   5940
ctgggagaac catctgcagt gacagcagct agtgccgccc agagacgtgg acgtatcggt   6000
agaaatccgt cgcaagttgg tgatgagtac tgttatgggg ggcacacgaa tgaagacgac   6060
tcgaacttcg cccattggac tgaggcacga atcatgctgg acaacatcaa catgccaaac   6120
ggactgatcg ctcaatttta ccaaccagag cgtgagaagg tatataccat ggatggggaa   6180
taccggctca gaggagaaga gagaaaaaac tttctggaac tgttgaggac tgcagatttg   6240
ccagtttggc tggcttacaa ggttgcagcg gctggagtgt cataccacga ccggaggtgg   6300
tgctttgatg tcctaggac aaacacaatt ttagaagaca caacgaagt ggaagtcatc   6360 acgaagcttg gtgaaaggaa gattctgagg ccgcgctgga ttgacgccag ggtgtactcg   6420
gatcatcagg cactaaaggc gttcaaggac ttcgcctcgg aaaacgttc tcagataggg   6480 ctcattgagg ttctgggaaa gatgcctgag cacttcatgg ggaagacatg gaagcactt   6540 gacaccatgt acgttgtggc cactgcagag aaaggaggaa gagctcacag aatggccctg   6600
gaggaactgc cagatgctct tcagacaatt gccttgattg ccttattgag tgtgatgacc   6660
atgggagtat tcttcctcct catgcagcgg aagggcattg gaaagatagg tttgggaggc   6720
gctgtcttgg gagtcgcgac ctttttctgt tggatggctg aagttccagg aacgaagatc   6780 gccgaatgt tgctgctctc ccttctcttg atgattgtgc taattcctga gccagagaag   6840
caacgttcgc agacagacaa ccagctagcc gtgttcctga tttgtgtcat gacccttgtg   6900
agcgcagtgg cagccaatga gatgggttgg ctagataaga ccaagagtga cataagcagt   6960
ttgtttgggc aaagaattga ggtcaaggag aattttagca tgggagagtt tcttctggac   7020
ttgaggccgg caacagcctg gtcactgtac gctgtgacaa cagcggtcct cactccactg   7080
ctaaagcatt tgatcacgtc agattacatc aacacctcat tgacctcaat aaacgttcag   7140
gcaagtgcac tattcacact cgcgcgaggc ttcccccttcg tcgatgttgg agtgtcggct   7200
ctcctgctag cagccggatg ctggggacaa gtcacccctca ccgttacggt aacagcggca   7260
acactccttt tttgccacta tgcctacatg gttccggtt ggcaagctga ggcaatgcgc   7320
tcagcccagc ggcggacagc ggccggaatc atgaagaacg ctgtagtgga tggcatcgtg   7380 gccacgacg tcccagaatt agagcgaacc acacccatca tgcagaagaa agttggacag   7440
atcatgctga tcttggtgtc tctagctgca gtagtagtga acccgtctgt gaagacagta   7500
cgagaagccg gaatttttgat cacggccgca gcggtgacgc tttgggagaa tggagcaagc   7560
tctgtttgga acgcaacaac tgccatcgga ctctgccaca tcatgcgtgg gggttggttg   7620
tcatgtctat ccatagcatg gacactcata aagaacatgg aaaaaccagg actaaaaga   7680 ggtgggcaa aaggacgcac cttgggagag gtttggaaag aaagactcaa ccagatgaca   7740
aaagaagagt tcactaggta ccgcaaagag gccatcatcg aagtcgatcg ctcagcggca   7800
aaacacgcca ggaagaagg caatgtcact ggagggcatc cagtctctag ggcacagca   7860 aaactgagat ggctggtcga acggaggttt ctcgaaccgg tcggaaaagt gattgacctt   7920
ggatgtggaa gaggcggctg gtgttactat atggcaaccc aaaaaagagt ccaagaagtc   7980
agagggtaca caagggcgg tccccggacat gaagagcccc aactagtgca aagttatgga   8040
tggaacattg ttaccatgaa gagtggagtg gatgtgttct acagaccttc tgagtgttgt   8100 gacacccctcc tttgtgacat cggagagtcc tcgtcaagtg ctgaggttga agagcatagg   8160
```

```
acgattcggg tccttgaaat ggttgaggac tggctgcacc gagggccaag ggaattttgc   8220
gtgaaggtgc tctgcccta catgccgaaa gtcatagaga agatggagct gctccaacgc    8280
cggtatgggg gggactggt cagaaaccca ctctcacgga attccacgca cgagatgtat    8340
tgggtgagtc gagcttcagg caatgtggta cattcagtga atatgaccag ccaggtgctc   8400
ctaggaagaa tggaaaaaag gacttggaag ggaccccaat acgaggaaga tgtaaacttg   8460
ggaagtggaa ccagggcggt gggaaaaccc ctgctcaact cagacaccag taaaatcaag   8520
aacaggattg aacgactcag gcgtgagtac agttcgacgt ggcactacga tgagaaccac   8580
ccatatagaa cctggaacta tcacggcagt tatgatgtga agcccacagg ctccgccagt   8640
tcgctggtca atggagtggt caggctcctc tcaaaaccat gggacaccat cacgaatgtt   8700
accaccatgg ccatgactga cactactccc ttcgggcagc agcgagtgtt caaagagaag   8760
gtggacacga aagctcctga accgccagaa ggagtgaagt acgtgctcaa cgagaccacc   8820
aactggttgt gggcgttttt ggccagagaa aaacgtccca gaatgtgctc tcgagaggaa   8880
ttcataagaa aggtcaacag caatgcagct ttgggtgcca tgtttgaaga gcagaatcaa   8940
tggaggagcg ccagagaagc agttgaagat ccaaaatttt gggagatggt ggatgaggag   9000
cgcgaggcac atctgcgggg ggaatgtcac acttgcattt acaacatgat gggaaagaga   9060
gagaaaaaac ccggagagtt cggaaaggcc aagggaagca gagccatttg gttcatgtgg   9120
ctcggagctc gctttctgga gttcgaggct ctgggttttc tcaatgaaga ccactggctt   9180
ggaagaagaa actcaggagg aggtgtcgag ggcttgggcc tccaaaaact gggttacatc   9240
ctgcgtgaag ttggcacccg gcctgggggc aagatctatg ctgatgacac agctggctgg   9300
gacacccgca tcacgagagc tgacttggaa aatgaagcta aggtgcttga gttgcttgat   9360
ggggaacatc ggcgtcttgc cagggccatc attgagctca cctatcgtca caaagttgtg   9420
aaagtgatgc gcccggctgc tgatggaaga accgtcatgg atgttatctc cagagaagat   9480
cagaggggga gtggacaagt tgtcacctac gccctaaaca ctttcaccaa cctggccgtc   9540
cagctggtaa ggatgatgga aggggaagga gtgattggcc cagatgatgt ggagaaactc   9600
acaaaaggga aaggacccaa agtcaggacc tggctgtttg agaatgggga agaaagactc   9660
agccgcatgg ctgtcagtgg agatgactgt gtggtaaagc ccctggacga tcgctttgcc   9720
acctcgctcc acttcctcaa tgctatgtca aaggttcgca aagacatcca agagtggaaa   9780
ccgtcaactg gatggtatga ttggcagcag gttccatttt gctcaaacca tttcactgaa   9840
ttgatcatga agatggaag aacactggtg gttccatgcc gaggacagga tgaattggta   9900
ggcagagctc gcatatctcc agggggccga tggaacgtcc gcgacactgc ttgtctggct   9960
aagtcttatg cccagatgtg gctgcttctg tacttccaca aagagagacct gcggctcatg  10020
gccaacgcca tttgctccgc tgtccctgtg aattgggtcc ctaccggaag aaccacgtgg  10080
tccatccatg caggaggaga gtggatgaca acagaggaca tgttggaggt ctggaaccgt  10140
gtttggatag aggagaatga atggatgaa gacaaaaccc cagtggagaa atggagtgac  10200
gtcccatatt caggaaaacg agaggacatc tggtgtggca gcctgattgg cacaagagcc  10260
cgagccacgt gggcagaaaa catccaggtg gctatcaacc aagtcagagc aatcatcgga  10320
gatgagaagt atgtggatta catgagttca ctaaagagat atgaagacac aacttttggtt  10380
gaggacacag tattgtagat atttaatcaa ttgtaaatag acaatataag tatgcataaa  10440
agtgtagttt tatagtagta tttagtggtg ttagtgtaaa tagttaagaa aattttgagg  10500
```

-continued

```
agaaagtcag gccgggaagt tcccgccacc ggaagttgag tagacggtgc tgcctgcgac    10560 tcaacccccag gaggactggg tgaacaaagc cgcgaagtga tccatgtaag ccctcagaac    10620
cgtctcggaa ggaggacccc acatgttgta acttcaaagc ccaatgtcag accacgctac    10680
ggcgtgctac tctgcggaga gtgcagtctg cgatagtgcc ccaggaggac tgggttaaca    10740
aaggcaaacc aacgccccac gcggccctag ccccggtaat ggtgttaacc agggcgaaag    10800
gactagaggt tagaggagac cccgcggttt aaagtgcacg gcccagcctg gctgaagctg    10860
taggtcaggg gaaggactag aggttagtgg agaccccgtg ccacaaaaca ccacaacaaa    10920
acagcatatt gacacctggg atagactagg agatcttctg ctctgcacaa ccagccacac    10980
ggctcagtgc gccgacaatg gtggctggtg gtgcgagaac acaggatct              11029
```

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ctcataaaga acatgggaaa accaggacta aaaagaggtg gggc                   44

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gccccacctc tttttagtcc tggttttccc atgttcttta tgag                   44

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gcagagagtt gtgtttatcg tgctattgct tttggtggcc ccagc                  45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gctggggcca ccaaaagcaa tagcacgata aacacaactc tctgc                  45

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 11
gccagcgtag gagcagttac cctctctgac ttccaaggga agg                    43

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ccttcccttg gaagtcagag agggtaactg ctcctacgct ggc                    43

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ggttggttgt catgtctatc catagcatgg acactc                            36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gagtgtccat gctatggata gacatgacaa ccaacc                            36

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
cgtgagtaca gttcgacgtg gcactacgat gagaaccacc c                      41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gggtggttct catcgtagtg ccacgtcgaa ctgtactcac g                      41

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
```

```
ccacgtggtc catccatgta ggaggagagt gg                                    32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ccactctcct cctacatgga tggaccacgt gg                                    32

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
caactttggt cgacgacaca gtactgt                                          27

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
tctagaagat cctgtgttct cgcacc                                           26

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
aaaagaaaag aggaggaaag                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gtttgtcatt gtgagcttct                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
```

-continued

```
gatgaatatg gaggcggtca                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ccgacgtcaa cttgacagtg                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
tgcatcaagc tttggctgga                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
tcttgccggc tgatgtctat                                          20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
agtagttcgc ctgtgtga                                            18

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
cagcagctgt tggaat                                              16

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gaaaacatca agtatgagg                                           19
```

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 30
gaggttcttc aaactccat                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 31
tggaggagtt ttgctcttc                                                19

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 32
tgtaccctgg tctcctgt                                                 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 33
gaagtcaaat catgcacc                                                 18

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 34
ctgtacacat caaggtttaa g                                             21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35
tttcttccaa atggcttac                                                19

```
<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ctcctctctt tgtgtactga                                              20

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
gatgatgatg gaaattttc                                               19

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
ggagacatca gcctg                                                   15

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
tgagatcgtt gatgtc                                                  16

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
cgtgatgact tcaac                                                   15

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
cataccatga ccggaaat                                                18
```

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ccatgtaagc atagtggc                                              18

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
acgtcagact acatcaacac tt                                         22

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
actccactct tcatggtaa                                             19

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
catgaagaac cacaactggt                                            20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
ccatcatgtt gtagatgca                                             19

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
ttttgggaga tggtggatga ggag                                       24

<210> SEQ ID NO 48

```
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 48
aacctgctgc cagtcatacc acccc                                       25

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 49
aatgctatgt caaaggtcc                                              19

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 50
cctggggcac tatcg                                                  15

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 51
gccaccggaa gttgagta                                               18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 52
cctgtgttct agcaccac                                               18
```

FLAVIVIRUS VARIANTS HAVING PHENOTYPIC VARIATION AND IMMUNOGENIC COMPOSITIONS THEREOF

The present invention claims priority to U.S. Provisional Patent Application Ser. No. 60/608,344, filed Sep. 9, 2004, which is incorporated by reference herein in its entirety.

The present invention was generated at least in part by funds from the National Institutes of Health grant number N01-AI25489. The United States Government may have certain rights in the invention.

FIELD OF THE INVENTION

The present invention generally concerns at least the fields of public health, virology, molecular biology, and cell biology. In particular, the field of the invention relates to members of the genus *Flavivirus*, such as West Nile viruses, comprising modifications that produce phenotypic variation, such as attenuation.

BACKGROUND OF THE INVENTION

West Nile virus (WNV) is a single stranded, positive-sense RNA virus belonging to the genus *Flavivirus* (family Flaviviridae). Historically, human infections with WNV, a member of the Japanese encephalitis serocomplex, usually were associated with a mild undifferentiated fever (Monath and Heinz, 1996). However, recent outbreaks in Europe, Israel, and North America involving humans, equines, and birds have been associated with significant rates of neurological disease (Lanciotti et al., 1999; Solomon and Vaughn, 2002). Until 1999, the geographical distribution of the virus was limited to Africa, the Middle East, India, and western and central Asia with occasional epizootics and epidemics in Europe (Murgue et al., 2002). But since the summer of 1999, the distribution of WNV has expanded to include 46 states of the continental U.S. and seven Canadian provinces, as well as Mexico and most likely a number of Caribbean Islands (Estrada-Franco et al., 2003; Komar et al., 2003; Blitvich et al., 2003; Dupuis et al., 2003; Quirin et al., 2004). As WNV has spread across North America, the number of human and veterinary cases and deaths has continued to rise, resulting in the largest recorded epidemic of arboviral encephalitis in the western hemisphere during 2002 (CDC, 2002). Because of its relatively recent introduction, studies concerning the evolution of WNV are important to understand the extent to which the virus has mutated as its temporal and geographic distributions have expanded. Nucleic acid sequencing studies of WNV isolates collected across the U.S. since 1999 have identified mutations to the genome when compared to the prototype New York strain, WN-NY99, which may also be referred to as 382-99 (GenBank Accession No. AF196835; SEQ ID NO:1), which reveal the presence of distinct genetic variants that group in a temporally- and geographically-dependent manner (Beasley et al., 2003; Davis et al., 2003).

Following the introduction of WNV into Texas during 2002, studies were initiated to determine if phenotypic changes also occurred among the genetic variants. Although genetically distinct on a microevolutionary scale, previous studies indicated that the phenotypic characteristics (i.e., plaque morphology, in vitro growth kinetics, neuroinvasiveness and neurovirulence in a mouse model) of WNV isolates collected in 2002 were not significantly different from isolates collected in 1999 (Beasley et al., 2003).

U.S. 2004/0052818 relates to attenuated live vaccines comprising *flavivirus* mutants, of which West Nile virus is a specific embodiment. In a further specific embodiment, the *flavivirus* mutant has a deletion in the capsid protein of at least more than 4 successive amino acids such that the carboxy-terminal hydrophobic region is not affected by the deletion.

U.S. 2004/0037848 describes an immunogenic or vaccine composition for induction of an immune response or protective immune response against WNV in an animal. The compositions comprise a vector containing a heterologous nucleic acid molecule that expresses in vivo a WNV antigen, immunogen, or epitope, such as WNV E; WNV prM and E; WNV M and E; WNV prM; WNV prM-E; WMV M-E; or WMV prM-M-E. In specific embodiments, the vector is a recombinant viral vector.

U.S. Pat. No. 6,576,757 is directed to nucleic acids encoding a recombinant multivalent antigenic polypeptide that comprises multiple non-contiguous subsequences of at least a first antigenic *flavivirus* polypeptide and multiple non-contiguous subsequences of at least a second antigenic *flavivirus* polypeptide, wherein the recombinant antigenic polypeptide induces a immune response greater than one induced by any one of the first or second polypeptides.

WO 03/061555 describes West Nile virus vaccines, particularly for horses, wherein the vaccine comprises an immunogenically active component such as a live attenuated, inactivated, or killed whole or subunit WN virus; an antigen derived therefrom; DNA derived therefrom, such as plasmid DNA; and a mixture thereof.

Thus, the present invention addresses a need in the art to identify *Flavivirus* variants comprising phenotypic changes that result in attenuation, and particularly for their use in immunogenic compositions for therapeutic purpose.

SUMMARY OF THE INVENTION

The present invention relates to specific sequence(s) in the viral genome West Nile Virus, phenotypic variation as a result therefrom, and corresponding immunogenic compositions.

The present invention provides the first evidence of phenotypic variation in the North American WNV population by the characterization of isolates exhibiting small plaque morphology, temperature-sensitivity, and/or attenuation in a mouse model. Previous mouse virulence studies have shown that both lineage 1 and 2 WNV isolates made from nature (i.e., mosquito pools, birds, horses, humans) differ in their ability to replicate in peripheral tissues, induce viremia, and invade the CNS (neuroinvasiveness), but that all strains are able to initiate a cytopathic infection in the CNS and cause encephalitis (neurovirulence) if virus is delivered directly to the brain via intracranial inoculation (Beasley et al., 2002). The present studies have shown similar findings in that naturally acquired isolates, which were attenuated for neuroinvasiveness, were not attenuated for neurovirulence.

Analysis of multiple variants is likely to identify multiple mutations that affect a range of phenotypic properties, including mouse virulence phenotypes. For those isolates that exhibited a temperature sensitive (ts) phenotype, it is possible that the mechanism of attenuation was the result of viral replication being sensitive to the temperature of the mouse following infection and induction of fever. Although ts variants of WNV and other *flaviviruses* have been produced in vitro by either cell culture passage or chemical mutagenesis (Blaney et al., 2003; Dunster et al., 1990; Hanley et al., 2002), to the knowledge of the present inventors, the natural occurrence of WNV isolates exhibiting temperature sensitivity has not been previously reported. It would be expected that variants will arise that are attenuated for a variety of hosts, including birds, equines, and/or humans, for example.

The present invention generally regards isolated *Flavivirus* variants, such as West Nile virus variants, having one or more modifications that produce phenotypic variation compared to a reference strain. In a particular embodiment, there is an isolated *Flavivirus* having one or more corresponding modifications in the *Flavivirus* genome in a structurally-related region to the North American West Nile virus.

In specific aspects of the invention, the modifications comprise mutations in the WNV genome relative to a prototypical reference strain, such as the highly virulent WN-NY99 strain, for example. In specific embodiments, the variants are identified in a North American geographical distribution, such as a United States geographical distribution, including a Texas geographical distribution, such as a south Texas geographical distribution, and including a Houston, Tex. metropolitan geographical distribution.

The virus variants may be obtained from any source, including, for example, isolated from an arthropod, such as an insect, including a mosquito; a tick; or a mammal or bird, such as from their blood or other organs. The virus variants may be naturally-occurring or they may be synthetic. The term "synthetic" as used herein refers to a virus isolate made by the hand of man, wherein a WNV, such as NY-99, was modified by molecular biological manipulation; this may be performed by standard means in the art, including by site-directed mutagenesis. In a particular aspect of the invention, part or all of the WNV genome is not part of a chimeric genome, such as those wherein the prM-E regions of WNV are swapped into other *Flavivirus* backbones (see Lai and Monath, 2003, for review).

The one or more modifications to the strain may be of any kind such that they result in phenotypic variation, particularly compared to a more virulent reference strain. Exemplary phenotypic varation may relate to attenuation of multiplication compared to a reference strain; small plaque phenotype; temperature-sensitive phenotype; reduced replication in cell culture; attenuation of neuroinvasiveness; attenuation of neurovirulence; reduced replication in vertebrates; reduced replication in arthropods; a combination thereof; and so forth. Modifications to the strain may occur in any region of the viral genome, for example including within any of the structural or nonstructural protein coding regions, and/or within the 5' or 3' non-coding regions.

All WNV, and indeed all *flaviviruses*, are relatively small, enveloped viruses that comprise a single-stranded RNA molecule with mRNA polarity as its genome. The genome has a long open reading frame that codes for all proteins in the form of a polyprotein. The individual mature virus proteins are formed by the activity of viral and cellular proteases. The arrangement of the individual virus proteins in the genome is the same for all *flaviviruses* and starts at the 5' end with the capsid protein, the surface proteins and a series of non-structural proteins, the last of which is the viral polymerase. The nucleocapsid of the *flaviviruses* is formed by just one single viral protein, i.e. the capsid protein, and surrounds the viral genome. The capsid is assumed to have an icosahedral symmetry. For reference, *Flavivirus* genomes comprise the following, in order from a 5' to 3' direction: prM; E; NS1, NS2A, NS2B, NS3, NS4A, NS4B, and NS5.

In certain aspects of the invention, one or more of the alterations may comprise one or more of the following: NS4B E249G, NS5 A804V, 3'UTR A10596G, 3' UTR C10774U, and 3' UTR A10799G. In some embodiments, the alteration is in a coding region for a nonstructural protein and/or in a noncoding region. In specific embodiments, the alteration is not in a E protein coding region.

The present invention provides particular mutations compared to the NY99 strain, although others not listed herein are within the scope of the invention. The mutations may be present in at least part of a β-sheet, an α-helix, a β-turn, a β-barrel, a β-hairpin, or a helix-turn-helix, or a combination thereof, for example. Exemplary differences between the WNV variant strains and the reference strain are included in Table 1, and in particular embodiments one or more of these alterations imparts one or more phenotypic variation characteristics to the virus.

TABLE 1

Exemplary Alterations of WNV Variants

| Location | Alteration |
|---|---|
| 3' UTR | nucleotide 10408 |
| 3' UTR | nucleotide 10851 |
| 3' UTR | nucleotide 10494 |
| 3' UTR | nucleotide 10596 |
| 3' UTR | nucleotide 10768 |
| 3' UTR | nucleotide 10774 |
| 3' UTR | nucleotide 10799 |
| 3' UTR | nucleotide 10851 |
| 3' UTR | nucleotide 10984 |
| 3' UTR | nucleotide 11000 |
| prM Protein | amino acid N4D |
| prM Protein | amino acid V156I |
| E Protein | amino acid T76A |
| NS1 Protein | amino acid E94G |
| NS2A Protein | amino acid V138I |
| NS3 Protein | amino acid E180D |
| NS3 Protein | amino acid E327K |
| NS4A Protein | amino acid V134M |
| NS4B Protein | amino acid V173I |
| NS4B Protein | amino acid T240A |
| NS5 Protein | amino acid T526I |
| NS5 Protein | amino acid A618S |
| NS5 Protein | amino acid A804V |
| NS5 Protein | amino acid R199L |
| NS5 Protein | amino acid A687D |
| NS5 Protein | amino acid A804V |
| NS5 Protein | amino acid H295Y |
| NS5 Protein | amino acid T6P |

Methods of utilizing WNV variants having phenotypic variation may employ one or more of the alterations provided in Table 1. In a specific embodiment, the variants further include one or more of the following alterations in Table 2.

TABLE 2

Additional Exemplary Amino Acid Alterations of WNV Variants

| Location | Alteration |
|---|---|
| prM Protein | amino acid V19I[1] |
| prM Protein | amino acid I141T[4] |
| prM Protein | amino acid K9R[5] |
| E Protein | amino acid A51V[5] |
| E Protein | amino acid K71N[5] |
| E Protein | amino acid T76A[5] |
| E Protein | amino acid R93K[1,2,3] |
| E Protein | amino acid I126T[1,2,3] |
| E Protein | amino acid N154K[2] |
| E Protein | amino acid N154S[1] |
| E Protein | amino acid S156P[2,3,4] |
| E Protein | amino acid V159A[This application] |
| E Protein | amino acid V159I[1,2,3] |
| E Protein | amino acid V159M[3] |
| E Protein | amino acid Y176H[2,3] |

TABLE 2-continued

Additional Exemplary Amino Acid Alterations of WNV Variants

| Location | Alteration |
| --- | --- |
| E Protein | amino acid A269T[3] |
| E Protein | amino acid V364M[2,3] |
| E Protein | amino acid V442I[2,3] |
| E Protein | amino acid S452L[2,3] |
| E Protein | amino acid I474V[1] |
| E Protein | amino acid A476T[5] |
| NS1 Protein | amino acid D7N[2,3] |
| NS1 Protein | amino acid S9T[2,3] |
| NS1 Protein | amino acid S17N[2,3] |
| NS1 Protein | amino acid E26K[3] |
| NS1 Protein | amino acid P36L[3] |
| NS1 Protein | amino acid I45V[3] |
| NS1 Protein | amino acid A70S[2,3] |
| NS1 Protein | amino acid L78P[2,3] |
| NS1 Protein | amino acid E109D[1] |
| NS1 Protein | amino acid M276I[1] |
| NS1 Protein | amino acid S174G[2,3] |
| NS1 Protein | amino acid L206F[2,3] |
| NS1 Protein | amino acid D234E[2,3] |
| NS2A Protein | amino acid A19V[1] |
| NS2A Protein | amino acid M34L[2,3] |
| NS2A Protein | amino acid T52A[3] |
| NS2A Protein | amino acid V112A[2,3] |
| NS2A Protein | amino acid H119Y[1,2,3] |
| NS2A Protein | amino acid E128G[3] |
| NS2A Protein | amino acid G165R[2,3] |
| NS2A Protein | amino acid A224T[2,3] |
| NS2B Protein | amino acid D82G[2,3] |
| NS2B Protein | amino acid G83E[2,3] |
| NS2B Protein | amino acid V103A[1,2,3] |
| NS2B Protein | amino acid I107V[2,3] |
| NS2B Protein | amino acid V120I[2,3] |
| NS2B Protein | amino acid T125S[1] |
| NS3 Protein | amino acid Q244H[3] |
| NS3 Protein | amino acid P249T[1,3] |
| NS3 Protein | amino acid P249I[2] |
| NS3 Protein | amino acid T356I[1,2,3] |
| NS3 Protein | amino acid G440A[2,3] |
| NS3 Protein | amino acid I462V[2] |
| NS3 Protein | amino acid L496P[2,3] |
| NS3 Protein | amino acid N503S[3] |
| NS3 Protein | amino acid D521E[2,3] |
| NS3 Protein | amino acid S557P[2,3] |
| NS4A Protein | amino acid A85V[1,2,3] |
| NS4A Protein | amino acid M141L[1,2] |
| NS4B Protein | amino acid S11N[1,2,3] |
| NS4B Protein | amino acid I13V[2,3] |
| NS4B Protein | amino acid V23A[1,2,3] |
| NS4B Protein | amino acid T165A[2,3] |
| NS4B Protein | amino acid I245M[2,3] |
| NS4B Protein | amino acid E249G[This application] |
| NS4B Protein | amino acid E249D[2,3] |
| NS5 Protein | amino acid P54S[2,3] |
| NS5 Protein | amino acid R177K[1,2,3] |
| NS5 Protein | amino acid V258A[1] |
| NS5 Protein | amino acid K280N[2,3] |
| NS5 Protein | amino acid V372A[2,3] |
| NS5 Protein | amino acid R403K[2,3] |
| NS5 Protein | amino acid P431L[2,3] |
| NS5 Protein | amino acid H450Y[1] |
| NS5 Protein | amino acid T681I[3] |
| NS5 Protein | amino acid V731A[1] |
| NS5 Protein | amino acid A860T[2,3] |
| NS5 Protein | amino acid T898I[2,3] |

The noted mutations are listed in at least the following references or references cited therein:
[1] Beasley et al., unpublished;
[2] Lanciotti et al. (2002);
[3] Charrel et al. (2003);
[4] Estrada-Franco et al. (2003);
[5] Davis et al. (2003)

Previous studies indicated that the phenotypic characteristics (i.e., plaque morphology, in vitro growth kinetics, neuroinvasiveness and neurovirulence in a mouse model, for example) of WNV isolates collected in 2002 were not significantly different from isolates collected in 1999 (Beasley et al., 2003). During the 2003 transmission season, however, isolates of WNV from both birds and mosquitoes collected in Texas were recovered that produced small plaque (sp) morphology and reduced virus yield at 72 hours following infection in Vero cells in comparison to isolates of WNV from previous transmission seasons. Several of these isolates displayed a temperature-sensitive (ts) phenotype and were attenuated for neuroinvasiveness in a mouse model in comparison to the prototype WN-NY99 strain. Complete genome sequencing of several exemplary phenotypically distinct isolates was undertaken by the present inventors to identify potential mutations in the WNV genome conferring these changes. This was directed to the first description of phenotypic variation among WNV isolates in North America.

Given the public health issues associated with *flaviviruses* including, WNV, in particular aspects of the invention the compositions and methods described herein regard immunogenic compositions, such as vaccines. Prophylactic or therapeutic methods utilizing the WNV variants of the invention include those wherein the attenuated WNV variants are administered to an individual and an immune response is thereby evoked. In particular embodiments, the immune response provides sufficient magnitude such that upon challenge immunity is achieved or retained. Any immunogenic composition is suitable such that it produces an immune response upon introduction to an individual. Any vaccine is suitable such that it produces at least partial protection from subsequent challenge by the same or a related pathogen. In particular embodiments of the invention, a related pathogen refers to another *Flavivirus*. In specific embodiments, an infectious clone of a WNV variant is utilized in an immunogenic composition.

In a particular aspect of the invention, the immunogenic composition or vaccine may be unable to cause one or more symptoms of severe, fulminant disease but still retains the antigens responsible for inducing an immune response in a host. A skilled artisan recognizes this can be achieved in a variety of ways. For example, in one embodiment, a WNV variant of the invention is killed, such as by using formalin, and is thus referred to as an "inactivated" or "killed" vaccine. Another embodiment for immunogenic composition/vaccine production utilizes one or more antigenic parts of the disease-causing organism, such as, for example, the one or more parts comprising the one or more modifications that result in the phenotypic variation, and these types of vaccines are referred to as "subunit vaccines." Subunit vaccines exhibit some similarities to killed vaccines in that neither killed nor subunit vaccines generally induce the strongest immune responses and may therefore require a "booster" every few years to ensure their continued effectiveness. In addition, neither killed nor subunit vaccines can cause disease and are therefore considered to be safe for use in immunocompromised patients.

Another embodiment of producing an immunogenic composition or vaccine is to "attenuate" or weaken a live microorganism by aging it or altering its growth conditions. Vaccines made in this way are often the most successful vaccines, probably because they multiply in the body, thereby causing a large immune response. Although these live, attenuated vaccines also carry risk because they can mutate back to the virulent form at any time, immunity is often lifelong with attenuated vaccines and does not require booster shots.

An additional method of making an immunogenic composition or vaccine is to use an organism that is similar to the virulent organism but that does not cause serious disease. For example, an immunogenic composition or vaccine of the present invention may comprise a WNV variant, and the composition or vaccine is introduced to an individual for the purpose of inducing an antibody response and/or protection against any *Flavivirus*, including Dengue virus, Japanese encephalitis, St. Louis Encephalitis, Kunjin virus, Yellow Fever virus, and so forth.

The present invention also provides methods of generating immunogenic compositions, such as vaccines, comprising the WNV variants of the invention. In specific embodiments, the immunogenic compositions further comprise an adjuvant.

In one embodiment of the present invention, there is a composition comprising at least part of an isolated North American West Nile virus having one or more modifications in the viral genome, wherein the genome comprises one or more coding regions, non-coding regions, or both, wherein the one or more modifications produce one or more phenotypic variations to the West Nile virus; and/or at least part of an isolated *Flavivirus* having one or more corresponding modifications in the *Flavivirus* genome, wherein the genome comprises one or more coding regions, non-coding regions, or both, wherein the modification is in a structurally-related region to the North American West Nile virus, and wherein the one or more modifications produce one or more phenotypic variations to the *Flavivirus*.

The modifications may be in a coding region of the genome or in a non-coding region of the genome. The one or more corresponding modifications in the structurally-related *Flavivirus* may be an identical or conservative modification. In specific embodiments, the structurally-related region comprises at least part of a β-sheet, an α-helix, a β-turn, a β-barrel, a β-hairpin, a helix-turn-helix, or a combination thereof.

In other specific embodiments, the phenotypic variation comprises attenuation compared to the multiplication of a reference strain; a small plaque phenotype; a temperature-sensitive phenotype; reduced replication in cell culture; attenuation of neuroinvasiveness; attenuation of neurovirulence; reduced replication in vertebrates; reduced replication in arthropods; or a combination thereof. In a particular embodiment, the phenotypic variation comprises attenuation compared to the multiplication of a corresponding reference strain, such as, for example, NY99. In a particular embodiment, the *Flavivirus* is dengue-1, dengue-2, dengue-3, dengue-4, Usutu, Japanese encephalitis, St. Louis Encephalitis, Kunjin, Yellow Fever virus, or tick-borne encephalitis serocomplex virus.

In further specific embodiments, one or more of the modifications in the West Nile virus comprises one or more of the exemplary alterations identified in Table 1. In a specific embodiment, the composition comprises an additional modification comprising amino acids E159 or NSB4249. The composition may also further comprise one or more of the exemplary amino acid modifications identified in Table 2, for example.

In particular embodiments, compositions of the present invention may be further defined as being an immunogenic composition and may also be further defined as comprising an adjuvant. In a further embodiment, the immunogenic composition is further defined as a vaccine, such as, for example, one comprising an adjuvant. The vaccine may be further defined as a live vaccine, a killed vaccine, an attenuated vaccine, a chimeric vaccine, or a subunit vaccine.

In another embodiment of the present invention, there is a method of preparing an immunogenic composition, by providing a composition of the present invention; providing a suitable excipient; and mixing the composition with the suitable excipient.

In an additional embodiment, there is a method of inducing an immune response in an individual, comprising delivering to the individual any one of the compositions of the present invention.

In another embodiment, there is a method of vaccinating an animal against West Nile virus infection or preventing such infection comprising administering to the animal a vaccine of the present invention.

In additional embodiments of the present invention, there is an isolated polynucleotide comprising SEQ ID NO:3; an isolated polynucleotide comprising SEQ ID NO:4; an isolated polynucleotide comprising SEQ ID NO:5; and an isolated polynucleotide comprising SEQ ID NO:6. These may be further defined as immunogenic compositions comprising at least part of one or more of these polynucleotides, and they may also further comprise an adjuvant.

In an additional embodiment, there is a method of inducing an immune response in an individual, comprising delivering to the individual one or more of the following alterations:

TABLE 3

Exemplary WNV Alterations Useful in the Invention

| Location | Alteration |
| --- | --- |
| 3' UTR | Nucleotide 10408 |
| 3' UTR | Nucleotide 10494 |
| 3' UTR | Nucleotide 10596 |
| 3' UTR | Nucleotide 10768 |
| 3' UTR | Nucleotide 10774 |
| 3' UTR | Nucleotide 10799 |
| 3' UTR | Nucleotide 10851 |
| 3' UTR | Nucleotide 10851 |
| 3' UTR | Nucleotide 10984 |
| 3' UTR | Nucleotide 11000 |
| prM Protein | amino acid I141T |
| prM Protein | amino acid K9R |
| prM Protein | amino acid N4D |
| prM Protein | amino acid V156I |
| prM Protein | amino acid V19I |
| E Protein | amino acid A269T |
| E Protein | amino acid A476T |
| E Protein | amino acid A51V |
| E Protein | amino acid I126T |
| E Protein | amino acid I474V |
| E Protein | amino acid K71N |
| E Protein | amino acid N154K |
| E Protein | amino acid N154S |
| E Protein | amino acid R93K |
| E Protein | amino acid S156P |
| E Protein | amino acid S452L |
| E Protein | amino acid T76A |
| E Protein | amino acid V159A |
| E Protein | amino acid V159I |
| E Protein | amino acid V159M |
| E Protein | amino acid V364M |
| E Protein | amino acid V442I |
| E Protein | amino acid Y176H |
| NS1 Protein | amino acid A70S |
| NS1 Protein | amino acid D234E |
| NS1 Protein | amino acid D7N |
| NS1 Protein | amino acid E109D |
| NS1 Protein | amino acid E26K |
| NS1 Protein | amino acid E94G |
| NS1 Protein | amino acid I45V |
| NS1 Protein | amino acid L206F |
| NS1 Protein | amino acid L78P |
| NS1 Protein | amino acid M276I |
| NS1 Protein | amino acid P36L |
| NS1 Protein | amino acid S174G |
| NS1 Protein | amino acid S17N |
| NS1 Protein | amino acid S9T |

TABLE 3-continued

Exemplary WNV Alterations Useful in the Invention

| Location | Alteration |
| --- | --- |
| NS2A Protein | amino acid A19V |
| NS2A Protein | amino acid A224T |
| NS2A Protein | amino acid E128G |
| NS2A Protein | amino acid G165R |
| NS2A Protein | amino acid H119Y |
| NS2A Protein | amino acid M34L |
| NS2A Protein | amino acid T52A |
| NS2A Protein | amino acid V112A |
| NS2A Protein | amino acid V138I |
| NS2B Protein | amino acid D82G |
| NS2B Protein | amino acid G83E |
| NS2B Protein | amino acid I107V |
| NS2B Protein | amino acid T125S |
| NS2B Protein | amino acid V103A |
| NS2B Protein | amino acid V120I |
| NS3 Protein | amino acid D521E |
| NS3 Protein | amino acid E180D |
| NS3 Protein | amino acid E327K |
| NS3 Protein | amino acid G440A |
| NS3 Protein | amino acid I462V |
| NS3 Protein | amino acid L496P |
| NS3 Protein | amino acid N503S |
| NS3 Protein | amino acid P249I |
| NS3 Protein | amino acid P249T |
| NS3 Protein | amino acid Q244H |
| NS3 Protein | amino acid S557P |
| NS3 Protein | amino acid T356I |
| NS4A Protein | amino acid A85V |
| NS4A Protein | amino acid M141L |
| NS4A Protein | amino acid V134M |
| NS4B Protein | amino acid E249D |
| NS4B Protein | amino acid E249G |
| NS4B Protein | amino acid I13V |
| NS4B Protein | amino acid I245M |
| NS4B Protein | amino acid S11N |
| NS4B Protein | amino acid T165A |
| NS4B Protein | amino acid T240A |
| NS4B Protein | amino acid V173I |
| NS4B Protein | amino acid V23A |
| NS5 Protein | amino acid A618S |
| NS5 Protein | amino acid A687D |
| NS5 Protein | amino acid A804V |
| NS5 Protein | amino acid A804V |
| NS5 Protein | amino acid A860T |
| NS5 Protein | amino acid H295Y |
| NS5 Protein | amino acid H450Y |
| NS5 Protein | amino acid K280N |
| NS5 Protein | amino acid P431L |
| NS5 Protein | amino acid P54S |
| NS5 Protein | amino acid R177K |
| NS5 Protein | amino acid R199L |
| NS5 Protein | amino acid R403K |
| NS5 Protein | amino acid T526I |
| NS5 Protein | amino acid T681I |
| NS5 Protein | amino acid T6P |
| NS5 Protein | amino acid T898I |
| NS5 Protein | amino acid V258A |
| NS5 Protein | amino acid V372A |
| NS5 Protein | amino acid V731A |

In a particular embodiment, there is a method of vaccinating an animal against West Nile virus infection or preventing such infection comprising administering to the animal a vaccine comprising at least part of a West Nile virus having one or more of the alterations presented in Table 3.

In certain aspects of the invention, a sample from an individual is collected from an individual for the determination of the presence of WNV, including a WNV having an alteration of the invention. Samples may be collected from individuals for such determination, and such samples may include, for example, blood, plasma, serum, cerebrospinal fluid, and so forth. The WNV may be identified by routine methods in the art, such as by culturing of the virus and sequencing of part or all of its genome, for example. In certain embodiments, region(s) of the genome that are sequenced include those that comprise one or more alterations of the invention.

In other embodiments, individuals are provided a WNV of the invention, including one suitable for use as an immunogenic composition, such as a vaccine. In specific embodiments, the individual receiving the composition is a mammal, such as a human, horse, dog, cat, pig, cow, goat, bird, sheep, and so forth, for example.

In one embodiment of the invention, there is an immunogenic virus, which may also be referred to as an immunogenic viral composition, that comprises at least part of an isolated North American West Nile virus genome, said genome having at least two alterations therein and comprising one or more coding regions, non-coding regions, or both, wherein said at least two alterations produce one or more phenotypic variations to the West Nile virus and wherein at least one of the alterations is not in a coding region for a structural protein. In a specific embodiment, the virus comprises all of the isolated North American West Nile virus genome. In another specific embodiment the virus comprises part of the isolated North American West Nile virus genome.

In particular embodiments of the virus, there is an alteration in a coding region for NS4B; in a coding region for NS5; and/or in the 3' UTR. At least one of the alterations may be selected from the group consisting of: NS4B E249, NS5 A804, 3'UTR A10596, 3' UTR C10774, and 3' UTR A10799. At least one of the alterations may be selected from the group consisting of: NS4B E249G, NS5 A804V, 3'UTR A10596G, 3' UTR C10774U, and 3' UTR A10799G. In further specific embodiments, at least one of the alterations is NS4B E249G; at least one of the alterations is NS5 A804V; at least one of the alterations is 3'UTR A10596G; at least one of the alterations is 3' UTR C10774U; and/or at least one of the alterations is 3' UTR A10799G.

In another embodiment of the invention, there is a method of manufacturing an immunogenic composition, the method comprising providing a virus of the invention and mixing said virus with a suitable excipient. There is also a method of inducing an immune response in an individual, comprising delivering to the individual an immunogenically effective amount of a virus of the invention. In specific aspects, the individual is a human, horse, cow, dog, cat, bird, pig, sheep, goat, monkey, gorilla, tiger, lion, elephant, giraffe, buffalo, camel, jaguar, puma, or bear, for example. In a further embodiment of the invention, there is a method of vaccinating an animal against West Nile virus infection comprising administering to the animal an immunogenically effective amount of a vaccine of the invention.

In a further embodiment of the invention, there is a composition comprising at least part of an isolated North American West Nile virus having at least two alterations in the viral genome, said genome comprising one or more coding regions, non-coding regions, or both, wherein said at least two alterations produce one or more phenotypic variations to the West Nile virus and wherein at least one of the alterations is not in a coding region for a structural protein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying FIGS. It is to be expressly understood, however, that each of the FIGS. is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1 illustrates homology between the E protein domain III (approximately 100 amino acids) of representative mosquito- and tick-borne viruses: DEN1 (SEQ ID NO: 53) DEN3 (SEQ ID NO: 55) DEN2 (SEQ ID NO: 54) DEN4 (SEQ ID NO: 56) JE (SEQ ID NO: 57) MV (SEQ ID NO: 58) KUN (SEQ ID NO: 59) WN (SEQ ID NO: 60) SLE (SEQ ID NO: 61) YF (SEQ ID NO: 62) TBE (SEQ ID NO: 63) KFD (SEQ ID NO: 64) KUM (SEQ ID NO: 65) LI (SEQ ID NO: 66) LGT (SEQ ID NO: 67) OHF (SEQ ID NO: 68) POW (SEQ ID NO: 69). The symbol * indicates homologous amino acids across the different *flaviviruses*.

FIG. 4 shows plaque morphology of NY99 infectious clone mutants.

FIG. 5 demonstrates viral growth curve of attenuated infectious clone mutants in comparison to NY99ic and a non-attenuated infectious clone mutant.

FIG. 8 provides a cartoon of an exemplary WN-NY99 infectious clone.

DETAILED DESCRIPTION OF THE INVENTION

Figure 2:
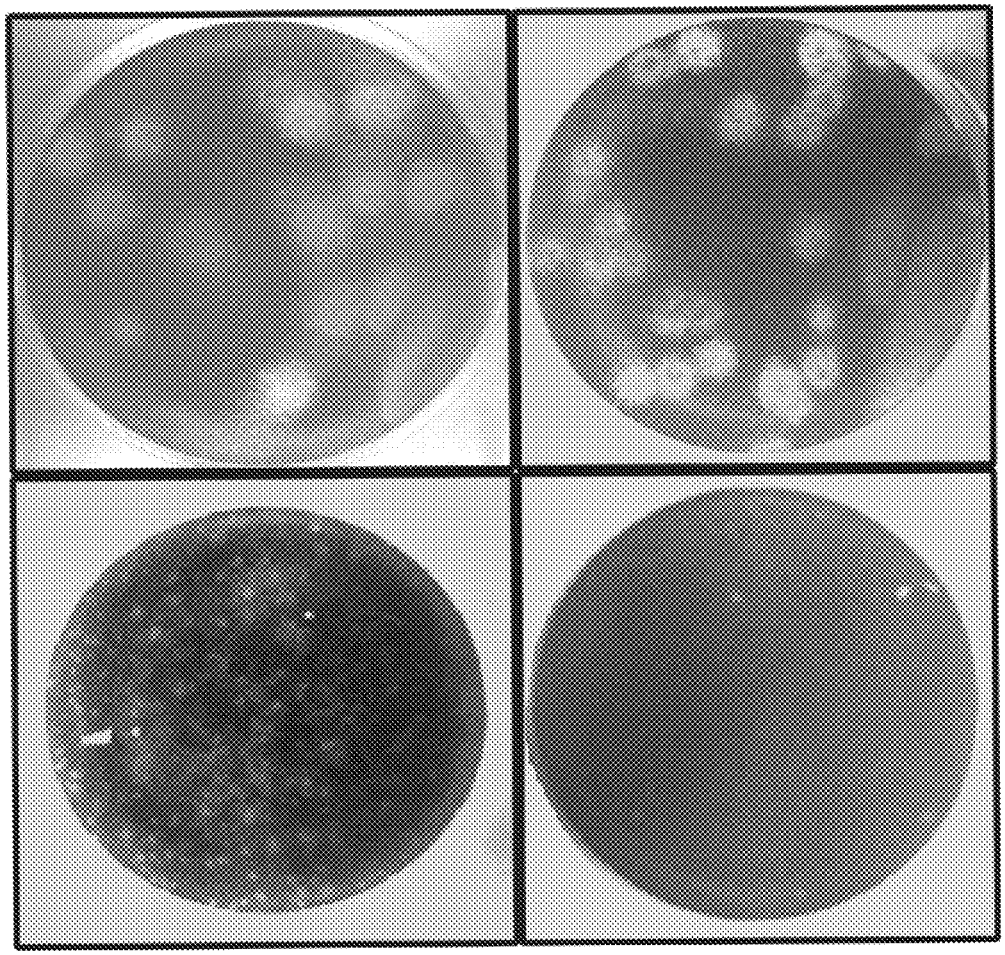
FIG. 2 is a plaque morphology of exemplary WNV isolates. Vero cells in 6-well plates were infected with WN-NY99, WNV 2002, WNV 2003 small plaques (sp). Plaques were visualized 3 days postinoculation by staining with crystal violet. Images from pictures were copied to Microsoft Photoshop and measured for plaque diameter. Small plaque morphology measured as <1 mm. Large plaque morphology was measured as >1.5 mm. (A) WN-NY99, strain 382-99. (B) WNV 2002. (C) Bird 1153 (2003). (D) Bird 1771 (2003).

As used herein the specification, "a" or "an" may mean one or more. As used herein in the claim(s), when used in conjunction with the word "comprising", the words "a" or "an" may mean one or more than one. As used herein "another" may mean at least a second or more. In certain aspects, one or more compositions and/or methods of the invention may consist of or consist essentially of one or more embodiments. Also, one of skill in the art recognizes that a particular embodiment of the invention is exemplary in nature and will apply to other embodiments of the invention.

I. Definitions

The term "adjuvant" as used herein refers to an immunological agent that increases an antigenic response.

The term "antibody" as used herein refers an immunoglobulin molecule, which is able to specifically bind to a specific epitope on an antigen. Antibodies can be intact immunoglobulins derived from natural sources or from recombinant sources and can be immunoactive portions of intact immunoglobulins.

The term "immunogenic composition" or "immunogen" as used herein refers to a substance that is capable of provoking an immune response.

The term "immunogenically effective amount" as used herein refers to the amount of a composition that at least induces an immune response in an individual administered thereto.

The term "neuroinvasive" as used herein refers to the ability of a virus to replicate in peripheral tissues, induce viraemia, and invade the central nervous system.

The term "neurovirulent" as used herein refers to the ability of a virus to initiate cytopathic infection in the central nervous system and to cause encephalitis.

The term "phenotypic variation" as used herein refers to an observable difference in a biological property, for example temperature sensitivity, for example, of a virus strain compared to a parental or reference strain, such as the prototype West Nile strain New York 99, for example.

The term "small plaque phenotype" as used herein refers to phenotype for a virus variant that produces a plaque diameter measured as <1 mm in a Vero cell plaque assay.

The term "structurally-related" as used herein refers to at least one region of a West Nile virus having one or more modifications (wherein the modification results in phenotypic variation, particularly in reference to a prototypical strain) that is related in structure, configuration, and the like to the corresponding region of another *Flavivirus* species, a genus of which West Nile virus is a species member. That is, although West Nile virus is, of course, not identical to other *Flavivirus es*, there is considerable identity and similarity between at least the secondary and/or tertiary structure of at least some analogous regions therein. For example, although a valine at 138 of the NS3 protein in West Nile is present, there may or may not be a valine at 138 of the NS3 protein in another *Flaviviruses*. However, the secondary and/or tertiary structure of at least this region of NS3 from West Nile and another *Flavivirus* is conserved, and therefore a modification at or near an analogous site in the corresponding NS3 region of the *Flavivirus* would also provide a modification resulting in phenotypic variation of the *Flavivirus*

The term "temperature-sensitive phenotype" as used herein refers to reduced replication of virus at temperatures above 37.0° C., for example about 39.5° C., about 40° C., about 41.0° C., etc.

The term "vaccine" as used herein refers to a formulation that comprises the composition of the present invention and that is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a subject, the vaccine is able to provoke an immune response including, but not limited to, the production of antibodies, cytokines and/or other cellular responses.

The term "West Nile Virus variant" as used herein refers to at least part of an isolated West Nile Virus having one or more alterations or modifications in its genome compared to a reference strain, such as the exemplary WNV-NY99 strain. In specific embodiments, an alteration comprises one or more mutations compared to the NY99 strain. In further specific embodiments, the alteration resides in either a coding sequence or a noncoding sequence. In additional specific embodiments, the modification results in phenotypic variation of the virus or part thereof.

The term "viremia" or "viraemia" as used herein refers to presence of a virus in the bloodstream.

II. The Present Invention

The present invention regards isolated *flaviviruses* having modifications that result in phenotypic variation, including attenuation in neuroinvasiveness and/or attenuation in neurovirulence, for example. Although in one particular aspect of the invention there is a WNV variant having one or more modifications resulting in phenotypic variation, in other aspects there are additional *flaviviruses* within the scope of the invention, including Dengue virus, Japanese encephalitis virus, St. Louis Encephalitis virus, Kunjin virus, Yellow Fever virus, tick-borne encephalitis virus, and so forth.

In order to understand how West Nile virus (WNV) has evolved since its introduction into North America, the present inventors characterized the genetic and phenotypic variation among WNV isolates collected in various areas during consecutive transmission seasons. The present invention describes for the first time phenotypic changes occurring in the North American WNV population. Several isolates collected in Texas during 2003, for example, display a small plaque (sp) and temperature sensitive (ts) phenotype, as well as reduced replication in cell culture, in comparison to isolates collected in 2002 and New York in 1999; at least several of these isolates were also attenuated in mouse neuroinvasiveness, but not for neurovirulence, although in alternative embodiments WNV isolates or variants comprise attenuation in neurovirulence. The complete genome and deduced amino acid sequences of several of these isolates have been determined in order to map the one or more mutations responsible for this phenotypic variation. These data indicate microevolution of WNV and the emergence of isolates exhibiting phenotypic variation.

III. West Nile Virus

West Nile viruses comprise a single stranded, positive-sense RNA virus belonging to the genus *Flavivirus*. The prototypical strain in the context of this invention is NY99; its genomic sequence is provided in GenBank Accession No. AF196835 (SEQ ID NO:1), and the deduced amino acid sequence is provided in AAF20092 (SEQ ID NO:2). There is a common coding order of proteins in WNV, including the capsid protein (C), the membrane protein (prM) and the major envelope glycoprotein (E) occupying approximately 25% of the ORF of the 5' end, and the rest of the ORF comprising non-structural (NS) proteins: NS1, NS2A, NS2B, NS3, NS4A, NS4B, and NS5. Their functions are reviewed, for example, in McMinn (1997): NS1 is a membrane-associated glycoprotein involved in RNA synthesis and the replication complex; NS3 may have tripartite functions, including protease, helicase, and RNA/NTP triphosphatase activities; NS2B may function in polyprotein cleavage in association with NS3; NS5 contains the viral RNA polymerase and methyltransferase. NS2A likely has a function in viral assembly (Liu et al., 2003), NS4A is part of the replication complex, and NS4B includes interferon antagonist activity.

Protein E, which is the major envelope protein glycoprotein, is the dominant antigen responsible for eliciting neutralizing antibodies and protective immune responses in the host. It is also the presumed cell receptor binding protein and mediator of membrane fusion and cell entry. Thus, in a particular embodiment of the invention, protein E is one of the proteins important for neurovirulence and neuroinvasiveness of the viruses.

Pathogenesis of WNV may follow that of *flavivirus* encephalitis, wherein after subcutaneous inoculation, virus replication is identified in typical draining lymph nodes, followed by development of a plasma viraemia (the presence of a virus in the blood stream). During viraemia, many extraneural tissues may be infected, in addition to there possibly being viral entry into the brain. Neuroinvasion may ensue, wherein the virus replicates in peripheral tissues, induces viraemia, and invades the central nervous system (CNS); this is in contrast to neurovirulence, wherein the virus initiates cytopathic infection in the CNS and causes encephalitis.

Clinically, the incubation of WNV is about 1 to 6 days, and the infected individual may exhibit one or more of the following symptoms, for example: fever (which may be biphasic); headache; backache; generalized myalgia; anorexia; generalized lymphadenopathy; pharyngitis; gastrointestinal symptoms, or a rash that is roseolar or maculopapular and usually localized to the chest, back, and upper extremities.

IV. Structural Similarity Among *Flaviviruses*

It is well-known in the art that the Flavivirus family comprises substantially similar structural and functional similarities, and indeed the family members all retain the same single polyprotein precursor having successively positioned structural and non-structural proteins cleaved therefrom.

As an example of conserved structure among *Flaviviruses*, Rey et al. (1999) generated a model for the folded structure of all *Flavivirus* E proteins based on crystallography of the tick-borne encephalitis virus protein E, and it is provided therein to analyze properties such as antigenicity. Rey et al. describe three domains of the E protein that correspond to the antigenic domains C, A, and B, respectively, all of which have predominately β-strand secondary structure: domain I—a central β-barrel; domain II—an elongated dimerization region; and domain III—a C-terminal immunoglobulin-like module. Domain I, the central domain, comprises about 120 amino acids in three segments (amino acids 1-51, 137-189, and 285-302, wherein the fold of the central domain is an 8-strand up and down β-barrel, and the axis of the barrel lies roughly parallel to the viral membrane. Two disulfide bonds reside in Domain I.

Domain II, comprising the two large loops connecting the segments between the segments of Domain I, fold together to form a dimerization domain of residues 52-136 and 190-284. Domain II comprises an extended, finger-like structure having a base of an antiparallel β-sheet of five short strands, with two α-helices packed against one surface. The elongated part of the domain comprises a three-stranded β-sheet, having three disulfide bridges, and a β-hairpin. It also comprises a cd loop at the tip of the domain, and the loop is contained within a hydrophobic glycine-rich sequence (amino acids 98-113) that is almost fully conserved in all *flaviviruses* and may be responsible for the fusogenic activity of the virus.

Domain III of the C-terminus has an IgC-like fold and is linked to Domain I by a 15-amino acid linking region and is anchored to the end of the linking region by a disulfide bridge. The axis of the β-barrel characteristic of immunoglobulins is perpendicular to the viral surface. Moreover, Rey et al. note that single mutations of a number of *flavivirus* strains are responsible for changes in the properties of host range and cell tropism, and virulence or attenuation, and they cluster into three distinct regions, including the distal face of domain III (sheet CFG); the base of domain II (between sheets gfeah and $klD_0$); and the contact between the domain I/domain III interface and the cde loop of the opposite subunit.

Modis et al. (2003) utilize a crystal structure of Dengue virus type 2 major envelope glycoprotein E to identify a hydrophobic pocket that opens and closes through a conformational shift in a β-hairpin at the interface between two domains, and they indicate that the feature provides a means for finding inhibitors of dengue and other *flaviviruses*.

Murthy et al. (1999a and 1999b) provide crystal structure of the NS3 serine protease domain of Dengue virus, although it is noted that it is useful as a model for the whole *Flavivirus* family and provides a structural basis for several mutational effects on enzyme activity. The NS3 protease comprises trypsin-like specificity, and there is a catalytic triad comprised of His51, Asp75, and Ser135, cleaving the polyprotein precursor at the junctions of NS2A-NS2B, NS2B-NS3, NS3-NS4A, and NS4B-NS5. The protease domain is comprised of residues 1-185. Specifically, both the amino- and carboyxl-terminal β barrels are six-stranded. Furthermore, it is noted therein that there is sequence similarity around the *flavivirus* serine protease cleavage sites and in residues that form the S1 pocket (specificity pocket) being conserved among a variety of *Flaviviruses*, and they acknoweldge that the model for substrate binding is applicable to other *flavivirus* serine proteases.

Murthy et al. (2000) expand on this work by providing the structure of a complex of NS3-pro (the protease domain) with an inhibitor from mung beans. They teach that the structure provided therein is prototypical of all *flavivirus* NS3-protease interactions with analogous inhibitors, given that residues that interact with the P1 Arg/Lys residue in the complex (Asp129, Tyr150, and Ser163) are conserved among *flaviviruses* and given that the sequences around the polyprotein cleavages sites poses either an Arg or a Lys at the P1 position.

Also, Bartelma and Padmanabhan (2002) describe characterization of Dengue virus type 2 NS3 protein and determine that the nucleoside triphosphatase and 5'-RNA triphosphatase activities share a common active site. Furthermore, they indicate that the crystal structure of NS3 would provide beneficial information to identify drugs for the therapeutic use against *flaviviruses*.

Egloff et al. (2002) describe the crystal structure of the methyltransferase/RNA-dependent RNA polymerase NS5 complexed with S-adenosyl-L-homocysteine. Specifically, NS5 has a globular fold comprising three subdomains: subdomain 2 (amino acids 55-222) folds into a seven-stranded β-sheet surrounded by 4 α-helices and closely resembles the catalytic domain of other AdoMet-dependent MTases, subdomain 1 (amino acids 7-54) is appended to the core as an N-terminal extension having a helix-turn-helix motif followed by a β-strand and an α-helix, and subdomain 3 (amino acids 223-267) is appended to the core as a C-terminal extension having an α-helix and two β-strands. Egloff et al. note that the structural features provide a unique basis for rational drug design against *flaviviruses* in general.

Jones et al. (2003) studied capsid proteins from yellow fever virus and dengue virus and determine that the secondary structure of the two proteins is predominately alpha-helical, and they are very similar in both their extent and position within their respective primary amino acid sequences, with only a minor exception.

Yu et al. (2004) reported structural characteristics of domain III of the envelope protein from a variety of *flaviviruses*, and they each comprise either β-sheets or β-turns; there was particular conformity between the respective mosquito-borne (WNV and dengue 2 viruses) and tick-borne *flaviviruses* (Langat and Omsk hemorrhagic fever viruses).

Dokland et al. (2004) describe the crystal structure of the core protein (C) of the Kunjin subtype of WNV, which forms the internal core that is surrounded by the envelope in the virion. It comprises four α-helices and forms dimers that are organized into tetramers, which themselves form extended filamentous ribbons resembling stacked α-helices. The authors note that only four of 105 amino acid residues in the mature C protein are nonidentical between Kunjin and WNV NY99 strains, and reference is made therein to the dengue virus C protein also forming dimers and having 4 α-helices (Ma et al., 2004). In Ma et al. (2004), the solution structure of the dengue virus capsid protein identifies a fold including a large dimerization surface contributed by two pairs of helices, one of which resembles a coiled coil. There is an asymmetric distribution of basic resides over the protein surface, with nearly half of them poised along one face of the dimer. Furthermore, the conserved hydrophobic region forms an apolar surface at the interface of the dimer. The authors propose therein that other *flavivirus* C proteins should have a similar fold given the sequence conservation among the C proteins.

Volk et al. (2004) determined the NMR solution structure of domain III of the WNV E protein and identified similarities to both the Dengue 2 type virus and Japanese encephalitis virus domain III proteins, although there are some differences that are likely responsible for strain-specific tropism and virulence.

Nall et al. (2004) describe a putative three-dimensional structure of the WNV protease (NS2B-NS3) based on the WNV and Dengue virus sequences (see FIGS. 2 and 8 therein). The authors note that the homology model facilitates design of inhibitors selective for *flavivirus* proteases as a whole and also note that antiviral treatments, including perhaps for inhibition of *flaviviruses* in general, may be realized as a result.

Amino acid sequence alignments of the mosquito and tick-borne *flavivirus* envelope protein have indicated that there is considerable sequence and structure similarity among *Flaviviruses*. Approximate positions of domains I, II, and III have been predicted based on the DEN2 and TBE crystal structures. DEN2 domain I spans residues 1-51, 132-192, and 280-295; domain II spans residues 52-131 and 193-279; domain III spans residues 296-394. TBE domain I spans residues 1-51, 137-189, and 285-302; domain II spans residues 52-136 and 190-284; domain III spans residues 303-395. The predicted residues making up the putative fusion peptide loop approximately spans residues 100-110, receptor-binding loop (mosquito-borne viruses only) approximately spans residues 404-407, and transmembrane region approximately spans residues 470-495. DEN2 domain positions are described by Modis et at (2003), and TBE positions are described by Rey et al. (1995).

Figure 1:
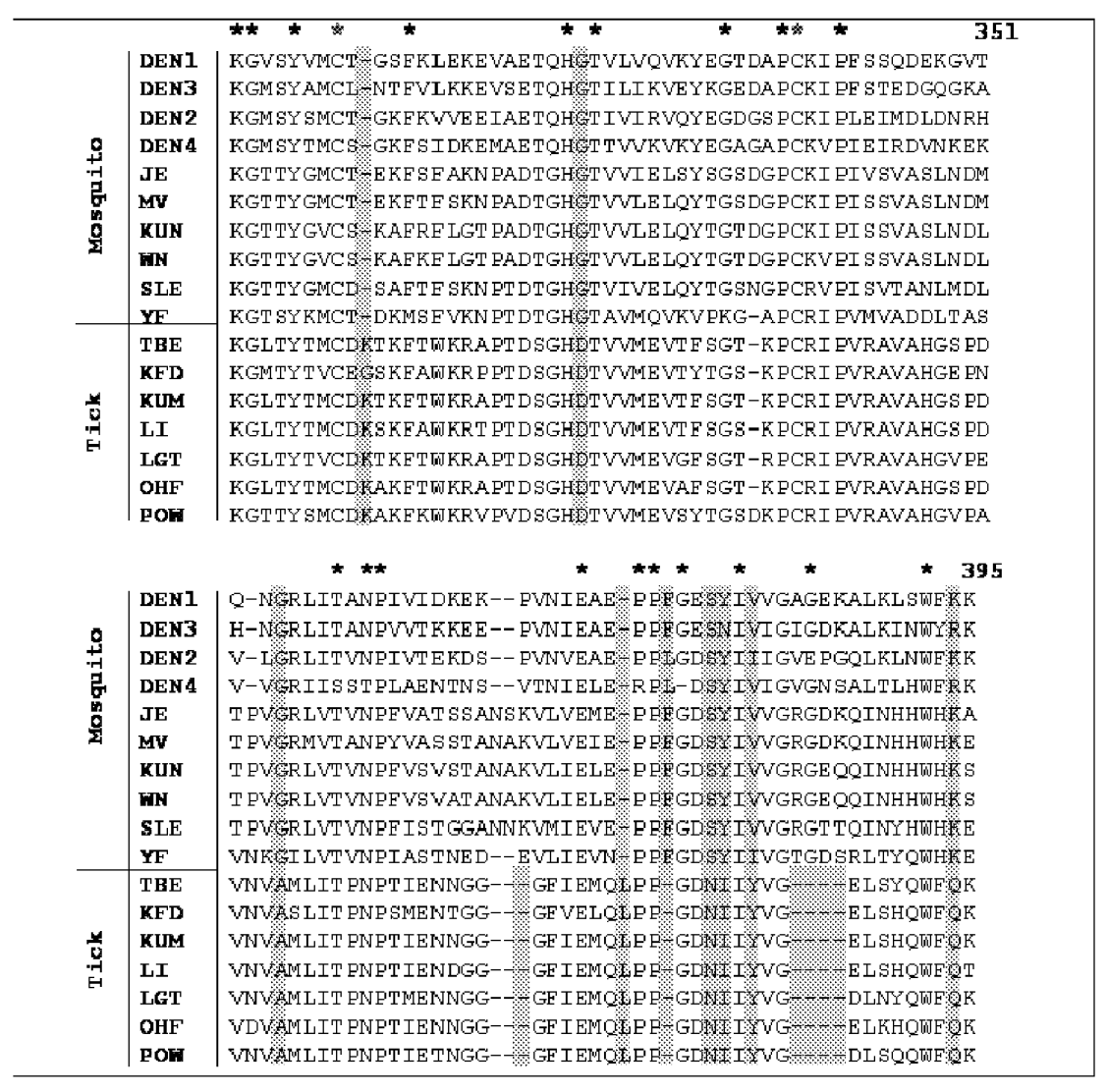

FIG. 1 shows the E protein domain III (approximately 100 amino acids) aligned for different mosquito- and tick-borne viruses. The symbol * indicates homologous amino acids for different *flaviviruses*.

Dengue fever is an important emerging public health concern, with several million viral infections occurring annually, for which no effective therapy currently exists. The NS3 protein from Dengue virus is a multifunctional protein of 69 kDa, endowed with protease, helicase, and nucleoside 5'-triphosphatase (NTPase) activities. Thus, NS3 plays an important role in viral replication and represents a very interesting target for the development of specific antiviral inhibitors. We present the structure of an enzymatically active fragment of the Dengue virus NTPase/helicase catalytic domain to 2.4 A resolution. The structure is composed of three domains, displays an asymmetric distribution of charges on its surface, and contains a tunnel large enough to accommodate single-stranded RNA. Its C-terminal domain adopts a new fold compared to the NS3 helicase of hepatitis C virus, which has interesting implications for the evolution of the Flaviviridae replication complex. A bound sulfate ion reveals residues involved in the metal-dependent NTPase catalytic mechanism. Comparison with the NS3 hepatitis C virus helicase complexed to single-stranded DNA would place the 3' single-stranded tail of a nucleic acid duplex in the tunnel that runs across the basic face of the protein. A possible model for the unwinding mechanism is proposed.

Yellow fever virus (YFV), a member of the *Flavivirus* genus, has a plus-sense RNA genome encoding a single polyprotein. Viral protein NS3 includes a protease and a helicase that are essential to virus replication and to RNA capping. The 1.8-A crystal structure of the helicase region of the YFV NS3 protein includes residues 187 to 623. Two familiar helicase domains bind nucleotide in a triphosphate pocket without base recognition, providing a site for nonspecific hydrolysis of nucleoside triphosphates and RNA triphosphate. The third, C-terminal domain has a unique structure and is proposed to function in RNA and protein recognition. The organization of the three domains indicates that cleavage of the viral polyprotein NS3-NS4A junction occurs in trans.

V. Detection of West Nile Virus

The West Nile virus variants of the present invention may be detected by any suitable means in the art. For example, and in general, the presence of the virus may be tested by isolation in cell culture. Upon isolation, its identification may be performed by immunofluorescence assays or by RT-PCR and/or TaqMan assays for a more rapid means of detection, such as from mosquito pools and avian tissues (Lanciotti et al., 2003; Martin et al., 2000; Shi et al., 2001). Furthermore, human infections can be deduced by IgM capture and IgG ELISAs, although confirmation of the type may be performed when there is a fourfold or greater rise in virus-specific neutralizing antibody titers in either serum or cerebrospinal fluid upon plaque reduction neutralization assay with several *flaviviruses* (Johnson et al., 2000; Martin et al., 2000).

In other exemplary methods, nucleic acid sequence-based amplification assays may be employed (Lancioitt and Kerst, 2001). In these approaches, two novel detection schemes may be utilized, including a postamplification detection step comprising a virus-specific internal capture probe and electrochemiluminescence and a real-time assay with 6-carboxyfluorescein-labeled virus-specific molecular beacon probes.

VI. *Flavivirus* Variants as Immunogenic Compositions/Vaccines

The *Flavivirus* variants of the present invention may be utilized or otherwise employed to generate an immunogenic composition, such as a vaccine, and in doing so thus relates to means for preventing and/or combating one or more diseases caused by the viruses, including those caused by WNV. The invention encompasses methods for inducing an immunological and/or protective immune response against *Flavivirus* in an animal comprising administering to the animal the immunogenic or vaccine composition of the present invention.

Advantageously, the immunogenic compositions and vaccines according to the invention comprise an effective quantity to elicit an immunological response and/or a protective immunological response for any of the compositions of the present invention, and an effective quantity can be determined from this disclosure, including the documents incorporated herein, and the considerable knowledge in the art.

The invention relates to immunogenic and vaccine compositions suitable for use in different animal (target or host) species susceptible to disease caused by *Flavivirus*, including, for example, mammals, especially humans, companion mammals, or animals such as canines, felines, or equines; reptiles; birds; and the like.

A. Immunogenic Compositions

In a particular embodiment of the invention, an immunogenic composition comprises one or more of the *Flavivirus* variants, including the WNV variants. A skilled artisan recognizes that the immunogenic composition may be a vaccine, although in alternative embodiments it is not a vaccine. The immunogenic composition may be any substance that is capable of provoking an immune response in an individual upon delivery of the composition to the individual. For example, the immunogenic composition may be at least part of the WNV variants of the invention comprising one or more modifications that impart phenotypic variation to the isolate, particularly in comparison to a reference strain. The immunogenic composition may comprise one or more agents to facilitate provoking the immune response, such as for eliciting a greater immune response than would be generated in the absence of the agent(s). In a specific embodiment, the agent is an adjuvant.

B. Vaccines

A variety of vaccines may be generated and employed according to the compositions of the present invention, including live vaccines, killed vaccines, attenuated vaccines, chimeric vaccines, and so forth. In a specific embodiment of the invention, the vaccine comprises an infectious clone of the variant and is a live vaccine.

For the preparation of conventional inactivated vaccines including recombinantly-prepared inactivated vaccines, for example, it is necessary to produce sufficient amounts of infectious and virulent virus. However, for embodiments wherein a live vaccine is employed, the amounts to be produced may be smaller, since the vaccine itself is propagated within the body of the vaccinated subject. In a specific embodiment, conventional inactivated *flavivirus* vaccines are prepared by inactivating infectious particles by treatment with formalin, resulting in a particular change of the antigen structure. In the vaccinated subject, primarily a humoral immune response to structure proteins whose antigen structure does not exactly correspond to the native form is induced. In contrast, with live vaccines according to the invention a humoral and cellular immune response to surface and non structure proteins can be achieved, whereby, according to the present state of the art, a substantially longer-lasting protective immune response can be achieved than with an inactivated vaccine.

C. Antibodies and Antibody Production

In certain embodiments, the present invention provides antibodies that bind with high specificity to the West Nile variants provided herein. These antibodies may be used for any suitable purpose, but in specific embodiments they are employed in various diagnostic or therapeutic applications described herein.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. Antibodies are typically tetramers of immunoglobulin molecules. The antibodies in the present invention exists in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

Means for preparing and characterizing antibodies are also well known in the art (See, e.g., Antibodies: A Laboratory Manual, Cold Spring Harbor Laboratory, 1988; incorporated herein by reference). Specific embodiments of antibodies include monoclonal antibodies or polyclonal antibodies. The term "antibody" may also refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin, for example, but due to the ease of preparation and availability of reagents, murine monoclonal antibodies will often be preferred. However, humanized antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more complementarity-determining regions (CDRs) from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

As is well known in the art, a given composition can vary in its immunogenicity. It is often necessary therefore to boost the host immune system, as is achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions. Exemplary adjuvants include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens can even be used. Other exemplary, often preferred, adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it is desirable to co-administer biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

1. Production of Polyclonal Antibodies

Polyclonal antibodies are prepared by immunizing an animal with an immunogenic WNV variant composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies.

2. Production of Monoclonal Antibodies

Monoclonal antibodies (MAb) are be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified WNV variant. The immunizing composition is administered in a manner effective to stimulate antibody producing cells.

Following immunization, somatic cells with the potential for producing antibodies, specifically B lymphocytes (B cells), are selected for use in the MAb generating protocol. These cells are obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells is used, as are known to those of skill in the art (Goding, pp. 65-66, 1986; Campbell, 1984). For example, where the immunized animal is a mouse, one can use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one can use R210.RCY3, Y3-Ag 1.2.3, IR983F and 4B210; and U-266, GM1500-GRG2, LICR-LON-HMy2 and UC729-6 are all useful in connection with human cell fusions. One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that is used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion can vary from about 20:1 to about 1:1, respectively, in the presence of an agent or agents (chemical or electrical) that promote the fusion of cell membranes. Fusion methods using Sendai virus are described by Kohler and Milstein (1975; 1976), and those using polyethylene glycol (PEG), such as 37% (v/v) PEG, by Gefter et al., (1977). The use of electrically induced fusion methods is also appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be either serially diluted and cloned into individual antibody-producing cell lines or individual cells physically cloned by means of pipetting, which clones can then be propagated indefinitely to provide MAbs. The cell lines are exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means are further purified, if desired, using filtration, centrifugation and various chromatographic methods such as HPLC or affinity chromatography. Fragments of the monoclonal antibodies of the invention can be obtained from the monoclonal antibodies so produced by methods, which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach can be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in *E. coli*.

VII. Immunodetection Methods

In still further embodiments, the present invention concerns immunodetection methods for binding, purifying, removing, quantifying and/or otherwise generally detecting biological components such as *Flavivirus* variants, including WNV variants of the present invention. The antibodies prepared in accordance with the present invention may be employed to detect WNV variants, including those that may be isolated, naturally-occuring, synthetic, or a combination thereof. As described throughout the present application, the use of WNV variant specific antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot, to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing a *Flavivirus* variant, such as a WNV variant (which will be referred to as the exemplary embodiment for the purposes of this discussion), and contacting the sample with an antibody in accordance with the present invention, as the case may be, under conditions effective to allow the formation of immunocomplexes. These methods may include methods for purifying WNV from patient samples and/or for purifying recombinantly expressed WNV variant. In these instances, the antibody removes the antigenic WNV variant from a sample. The antibody will preferably be linked to a solid support, such as in the form of a column matrix, and the sample suspected of containing the WNV variant will be applied to the immobilized antibody. The undesired components will be washed from the column, leaving the antigen immunocomplexed to the immobilized antibody, which WNV variant may then be identified and/or collected by removing the WNV variant from the column, or otherwise detected.

The immunobinding methods also include methods for detecting and quantifying the amount of a WNV variant reactive component in a sample and the detection and quantification of any immune complexes formed during the binding process. Here, one would obtain a sample suspected of containing a WNV variant, and contact the sample with an antibody against WNV variant, and then detect and quantify the amount of immune complexes formed under the specific conditions.

In terms of antigen detection, the biological sample analyzed may be any sample that is suspected of containing a WNV variant, such as a mammalian, avian, or arthropod tissue section or specimen, such as blood, a cell, and/or separated and/or purified forms of any of the above WNV variant-containing compositions. WNV-related diseases that may be suspected of containing a WNV variant include, but are not limited to, those having symptoms similar to WNV-related diseases, including fever (which may be biphasic), headache, backache, generalized myalgia, anorexia, generalized lymphadenopathy, pharyngitis, rash, and gastrointestinal symptoms, for example.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any WNV variant antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The WNV variant antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target WNV variant antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Exemplary immunoassays are listed below.

1. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the WNV variant antibodies of the invention are immobilized onto a selected surface exhibiting protein affinity, such as a well in a polystyrene microtiter plate. Then, a test composition suspected of containing the WNV variant antigen, such as a clinical sample, is added to the wells. After binding and/or washing to remove non-specifically bound immune complexes, the bound WNV variant antigen may be detected. Detection is generally achieved by the addition of another antibody that is linked to a detectable label. This type of ELISA is a simple "sandwich ELISA".

Detection may also be achieved by the addition of a second WNV variant antibody, followed by the addition of a third antibody that has binding affinity for the second antibody, with the third antibody being linked to a detectable label. Other exemplary ELISA methods are well-known in the art.

2. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

3. Immunoelectron Microscopy

The antibodies of the present invention may also be used in conjunction with electron microscopy to identify intracellular tissue components. Briefly, an electron-dense label is conjugated directly or indirectly to the WNV variant antibody. Examples of electron-dense labels according to the invention are ferritin and gold. The electron-dense label absorbs electrons and can be visualized by the electron microscope.

VIII. Nucleic Acids Encoding *Flavivirus* Variants

In particular embodiments, the present invention provides isolated nucleic acid sequences encoding at least part of a West Nile virus variant or a structurally-related *Flavivirus* variant. In further particular embodiments, the present invention provides isolated nucleic acid sequences of at least part of West Nile virus variants comprising Bird 1153 (AY712945; SEQ ID NO:3); Bird 1171 (AY712946; SEQ ID NO:4); Bird 1461 (AY712947; SEQ ID NO:5); and/or MosqV4369 (AY12948; SEQ ID NO:6). The term "comprises SEQ ID NO:3, SEQ ID NO:4, SEQ ID NO:5, and/or SEQ ID NO:6" means that the nucleic acid sequence substantially corresponds to at least a portion of SEQ ID NO:3, SEQ ID NO:4, SEQ ID NO:5, and/or SEQ ID NO:6.

The term "nucleic acid" generally refers to at least one molecule or strand of DNA, RNA or a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. An "isolated nucleic acid" as contemplated in the present invention may comprise transcribed nucleic acid(s), regulatory sequences, coding sequences, or the like, isolated substantially away from other such sequences, such as other naturally occurring nucleic acid molecules, regulatory sequences, polypeptide or peptide encoding sequences, etc.

Nucleic acids according to the present invention may comprise an entire *Flavivirus* variant, such as WNV variant, polynucleotide, or any fragment or variant of a WNV variant as set forth herein. A nucleic acid of the present invention may be derived from genomic RNA, i.e., cloned directly from the genome of a particular *Flavivirus*, such as West Nile virus. It is contemplated that the nucleic acids of the present invention may comprise complementary DNA (cDNA). The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a polynucleotide of a given WNV variant may be represented by natural or synthetic variants that have slightly different nucleic acid sequences but, nonetheless, encode the same or homologous protein (Table 4). As used in this application, the term "polynucleotide" refers to a nucleic acid molecule that has been at least substantially isolated free of total cellular nucleic acid. In exemplary embodiments, the invention concerns a nucleic acid sequence essentially as set forth in SEQ ID NO:3, SEQ ID NO:4, SEQ ID NO:5, and SEQ ID NO:6.

TABLE 4

Amino Acids and the Corresponding Codons

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

Allowing for the degeneracy of the genetic code, sequences that have at least about 60%, at least about 70%, at least about 80%, preferably at least about 90% and most preferably about 95% of nucleotides that are identical to the nucleotides of SEQ ID NO:3, SEQ ID NO:4, SEQ ID NO:5, and/or SEQ ID NO:6 are contemplated. Sequences that are essentially the same as those set forth in SEQ ID NO:3, SEQ ID NO:4, SEQ ID NO:5, and/or SEQ ID NO:6 may also be functionally defined as sequences that are capable of hybridizing to a nucleic acid sequence containing the complement of SEQ ID NO:3, SEQ ID NO:4, SEQ ID NO:5, and/or SEQ ID NO:6 under standard conditions. The term "functionally equivalent codon" is used herein to refer to codons that encode the same amino acid, such as the six codons for arginine or serine (Table 4), and also refers to codons that encode biologically equivalent amino acids, as discussed herein.

Naturally, the present invention also encompasses nucleic acid sequences that are complementary, or essentially complementary, to the sequences set forth herein, for example, in SEQ ID NO:3, SEQ ID NO:4, SEQ ID NO:5, and/or SEQ ID NO:6. Nucleic acid sequences that are "complementary" are those that are capable of base-pairing according to the standard Watson-Crick complementarity rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein, for example SEQ ID NO:3, SEQ ID NO:4, SEQ ID NO:5, and/or SEQ ID NO:6 under relatively stringent conditions such as those described herein. Such sequences may encode an entire WNV variant molecule or functional or non-functional fragments thereof.

The hybridizing sequences may be short oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of about 15, 16, 17, 18, 19, 20, 21, 22, 23, 24, 25, 30, 35, 40, 45, 50, 55, 60, 70, 80 or more base pairs will be used, although longer polynucleotides are contemplated. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of the probe and the target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other instances, hybridization may be achieved under conditions of, for example, 50 mM Tris-HCl (pH 8.3), 75 mm KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C. Formamide and SDS also may be used to alter the hybridization conditions.

IX. Biological Functional Equivalents

The present invention provides *Flavivirus* variants, such as WNV variants, having one or more modifications that produce phenotypic variation, in the context that the modifications are in comparison to a reference strain, such as WNV-NY99, for example. However, a skilled artisan recognizes that additional modifications may be provided and the variants would still retain phenotypic variation. Thus, as modifications and/or changes may be made in the sequence or structure of the polynucleotides and and/or proteins according to the present invention, while obtaining molecules having similar or improved characteristics, such biologically functional equivalents are also encompassed within the present invention.

A. Modified Polynucleotides and Polypeptides

The biological functional equivalent may comprise a polynucleotide that has been engineered to contain distinct sequences while at the same time retaining the capacity to encode the WNV variant. This can be accomplished to the degeneracy of the genetic code, i.e., the presence of multiple codons, which encode for the same amino acids (see Table 4). In one example, one of skill in the art may wish to introduce a restriction enzyme recognition sequence into a polynucleotide while not disturbing the ability of that polynucleotide to encode a protein.

In another example, a polynucleotide may be (and encode) a biological functional equivalent with more significant changes. Certain amino acids may be substituted for other amino acids in a protein structure (see Table 4) without appreciable loss of the desired function, such as the interactive binding capacity with structures including, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

The term "conservative substitution" as used herein refers to replacing an amino acid in a peptide or polypeptide with a different amino acid of a similar chemical nature. For example, a nonpolar amino acid may be conservatively substituted with another nonpolar amino acid. In specific embodiments, a hydrophobic amino acid may be substituted with another hydrophobic amino acid; a polar amino acid may be conservatively substituted with another polar amino acid; and/or a hydrophilic amino acid may be conservatively substituted with another hydrophilic amino acid.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) wherein selected amino acids (or codons) may be substituted. Functional activity of providing phenotypic variation is retained therein, however.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5) (Kyte and Doolittle, 1982).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (0.4); proline (−0.5±1); alanine (0.5); histidine (0.5); cysteine (1.0); methionine (1.3); valine (1.5); leucine (1.8); isoleucine (1.8); tyrosine (2.3); phenylalanine (2.5); tryptophan (3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

B. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table of exemplary, but not limiting, modified and/or unusual amino acids is provided herein below.

TABLE 5

Modified and/or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

C. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

X. Kits of the Invention

In one embodiment of the present invention, there are kits provided that regard the *Flavivirus* variant compositions (such as the exemplary WNV variant compositions), immunodetection reagents thereto, and/or immunogenic compositions, all of which are housed in a suitable container.

In some embodiments of the invention, the kit comprises one or more of SEQ ID NO:3, SEQ ID NO:4, SEQ ID NO:5, SEQ ID NO:6. In additional embodiments, the kit comprises a primer for polymerase chain reaction. In specific embodiments, the kit comprises an oligonucleotide for site-directed mutagenesis, such as one of the exemplary SEQ ID NOS:7-18.

The kits related to the WNV variant compositions include one or more of the variant polynucleotides, polypeptides, or fragments and derivatives thereof. The kits may be further defined as comprising an immunogenic composition, such as a vaccine, comprising one or more WNV variants of the invention.

In still further embodiments, the present invention concerns immunodetection kits for use with the immunodetection methods described above. As the WNV variant antibodies are generally used to detect WNV variants, the antibodies will preferably be included in the kit. However, kits including both such components may be provided. The immunodetection kits will thus comprise, in suitable container means, a first antibody that binds to a WNV variant, and/or optionally, an immunodetection reagent and/or further optionally, a WNV variant itself.

In preferred embodiments, monoclonal antibodies will be used, although in alternative embodiments polyclonal antibodies are used. In certain embodiments concerning the kit, the first antibody that binds to the WNV variant may be pre-bound to a solid support, such as a column matrix and/or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present invention.

The kits can include methods and/or reagents to collect a sample for detection of a WNV of the invention. Sample collecting reagents may include a syringe or catheter, for example.

The kits may further comprise a suitably aliquoted composition of the WNV variant, whether labeled and/or unlabeled, as may be used to prepare a standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will generally include at least one vial, test tube, flask, bottle, syringe and/or other container means, into which the antibody may be placed, and/or preferably, suitably aliquoted. Where a WNV variant, and/or a second and/or third binding ligand and/or additional component is provided, the kit will also generally contain a second, third and/or other additional container into which this ligand and/or component may be placed. The kits of the present invention will also typically include a means for containing the antibody, antigen, and/or any other reagent containers in close confinement for commercial sale. Such containers may include injection and/or blow-molded plastic containers into which the desired vials are retained.

XI. Site-directed Mutagenesis

Although the present invention regards, in one embodiment, naturally-occuring *Flavivirus* variant, such as the exemplary WNV variant, having phenotypic variation, in another embodiment a WNV variant having phenotypic variation is generated in accordance with one or more of the alterations described herein. One exemplary method for manufacturing alterations includes site-directed mutagenesis of a nucleic acid.

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation.

This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

XII. Using the Attenuating Alterations to Identify Antiviral Drugs

In particular aspects of the invention, one or more of the attenuating alterations of the WNV of the invention is utilized to identify antiviral drugs for one or more of the target attenuating alteration(s). The drug is then manufactured and administered to an individual in need thereof, such as one susceptible to being infected with a Flavivirus or one who is infected with a Flavivirus.

In one specific embodiment, rational drug design is employed to identify one or more targets for one or more of the attenuating alterations of the invention. The goal of rational drug design can be to produce structural analogs of biologically active compounds. By creating such analogs, it is possible to fashion drugs that are more active or stable than the natural molecules, which have different susceptibility to alteration or that may affect the function of various other molecules. In one approach, one would generate or obtain a three dimensional structure for the WNV with the attenuating alteration(s) of the invention or a fragment thereof. This could be accomplished by X-ray crystallography, computer modeling or by a combination of both approaches, for example.

It also is possible to isolate a specific antibody that binds at least part of a region of the WNV having the one or more alterations of the invention and then solve its crystal structure. In principle, this approach yields a pharmacore upon which subsequent drug design can be based. It is possible to bypass protein crystallography altogether by generating anti idiotypic antibodies to a functional, pharmacologically active antibody. As a mirror image of a mirror image, the binding site of anti idiotype would be expected to be an analog of the original antigen. The anti idiotype could then be used to identify and isolate peptides from banks of chemically or biologically produced peptides. Selected peptides would then serve as the pharmacore. Anti idiotypes may be generated using the methods described herein for producing antibodies, using an antibody as the antigen.

Thus, one may design drugs that have enhanced and improved biological activity, for example, the ability to target and render ineffective a WNV. Alternatively, a library of compounds known to recognize the one or more proteins comprising the one or more alterations is employed to identify a drug that binds the attenuating mutation.

The present invention further includes manufacturing of the one or more compounds that target the alteration(s) of the invention. In specific embodiments, the manufactured compound is administered to an individual susceptible to being infected with a Flavivirus or to an individual already infected with Flavivirus.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Small Plaque and Temperature Sensitive Isolates

Six of 29 isolates made by the inventors during the 2003 WNV transmission season were identified with a sp phenotype (FIG. 2). All sp isolates were collected in Harris Co. or Montgomery Co., Tex. and were made over a four-month period (May 9-Sep. 8, 2003). Previous studies with other related flaviviruses (yellow fever, dengue, tick-borne encephalitis, St. Louis encephalitis, and Japanese encephalitis viruses) have shown that some viruses with sp phenotypes are also temperature-sensitive (ts) when grown in cell culture at temperatures higher than their permissive temperature (37.0° C. for WNV) (Blaney et al., 2003; Ledger et al., 1992; Hollingshead et al., 1983; Eastman and Blair, 1985; Wallner et al., 1996). Thus, experiments were conducted to determine if sp and non-sp producing isolates of WNV collected in 1999, 2002, and 2003 displayed a ts phenotype (Table 6).

sp, ts, and Mouse Attenuation Phenotypes of West Nile Viruses isolated in Texas, 2003

| | | | Mean virus titer ($\log_{10}$ PFU/ml) at indicated temperature (° C.) | | | Mouse neuroinvasiveness and neurovirulence | | | |
| --- | --- | --- | --- | --- | --- | --- | --- | --- | --- |
| | | | Vero | | | Intraperitoneal inoculation | | Intracranial inoculation | |
| Virus | Source | Small plaque | 37° C. | 39.5° C. | Δ | $LD_{50}$ (PFU) | AST ± s.d.(days) | $LD_{50}$ (PFU) | AST ± s.d.(days) |
| WN-NY99 (382-99) | Flamingo brain | — | 8.1 | 7.6 | 0.5 | 0.8 | 8.0 ± 1.2 | 0.1 | 6.4 ± 0.9 |
| WN-99 (385-99) | Owl brain | — | 7 | 7.3 | 0.3 | 0.4 | 7.2 ± 0.6 | 0.4 | 6.0 ± 0.2 |
| TWN 93 (2002) | Bird 113 | — | 7.9 | 7.7 | 0.2 | 0.5 | 8.0 ± 1.0 | 0.1 | 6.7 ± 0.3 |

-continued sp, ts, and Mouse Attenuation Phenotypes of West Nile Viruses isolated in Texas, 2003

| | | | | Mean virus titer ($\log_{10}$ PFU/ml) at indicated temperature (° C.) | | | Mouse neuroinvasiveness and neurovirulence | | | |
| --- | --- | --- | --- | --- | --- | --- | --- | --- | --- | --- |
| | | | Small | Vero | | | Intraperitoneal inoculation | | Intracranial inoculation | |
| | Virus | Source | plaque | 37° C. | 39.5° C. | Δ | $LD_{50}$ (PFU) | AST ± s.d. (days) | $LD_{50}$ (PFU) | AST ± s.d. (days) |
| | TWN 84 (2002) | Bird 114 | — | | | | 4.2 | 7.5 ± 1.2 | n.d. | n.d. |
| | TWN 117 (2002) | Bird 476 (Bolivar) | — | | | | 1.8 | 8.6 ± 0.7 | n.d. | n.d. |
| 2003 | TWN 269 | Bird 1171 | sp | 6 | 3.3 | 2.7 | ≧1,000 | n/a | n.d. | n.d. |
| WNV | TWN 270 | Bird 1175 | sp | 3.5 | 1 | 2.5 | ≧1,000 | n/a | n.d. | n.d. |
| Isolates | TWN 271 | Bird 1240 | — | 3.5 | 3.4 | 0.1 | ≦100 | 8.0 ± 2.0 | n.d. | n.d. |
| | TWN 274 | Bird 1153 | sp | 7.7 | 5 | 2.7 | ≧1,000 | n/a | 0.3 | 6.2 ± 0.4 |
| | TWN 300 | Bird 1427 | — | 5.4 | 5.9 | 0.5 | ≦100 | 7.0 ± 1.0 | n.d. | n.d. |
| | TWN 301 | Bird 1461 | — | 7 | 6.7 | 0.3 | ≦100 | 7.0 ± 1.0 | 0.2 | 6.2 ± 0.6 |
| | TWN 302 | Bird 1479 | sp | 6.3 | 7 | 0.7 | ≧100 | n/a | n.d. | n.d. |
| | TWN 303 | Bird 1481 | — | 6 | 6.2 | 0.2 | ≦100 | 7 | n.d. | n.d. |
| | TWN 304 | Bird 1496 | — | 6.2 | 6.7 | 0.5 | ≦100 | 7.2 ± 1.0 | n.d. | n.d. |
| | TWN 305 | Bird 1519 | sp | 6.3 | 6.6 | 0.3 | ≧1,000 | n/a | 0.1 | 6.9 ± 0.2 |
| | TWN 358 | Mosq. v2769 | — | 6.1 | 6.3 | 0.2 | ≦100 | 7.5 ± 3.0 | n.d. | n.d. |
| | TWN 359 | Mosq. v3437 | — | 6.2 | 6.6 | 0.4 | ≦100 | 7.0 ± 1.0 | n.d. | n.d. |
| | TWN 360 | Mosq. v3567 | — | 7.1 | 6.7 | 0.4 | ≦100 | 8.6 ± 2.0 | n.d. | n.d. |
| | TWN 361 | Mosq. v3693 | — | 7.2 | 7.2 | 0 | ≦100 | 8.4 ± 1.0 | n.d. | n.d. |
| | TWN 362 | Mosq. v3941 | — | 7.2 | 7 | 0.2 | ≦100 | 7.3 ± 1.0 | n.d. | n.d. |
| | TWN 363 | Mosq. v3942 | — | 7.2 | 7.3 | 0.1 | ≦100 | 8.2 ± 1.0 | n.d. | n.d. |
| | TWN 364 | Mosq. v4007 | — | 8 | 8 | 0 | ≦100 | 8.0 ± 2.0 | n.d. | n.d. |
| | TWN 365 | Mosq. v4095 | — | 7.5 | 7.7 | 0.2 | ≦100 | 8.4 ± 1.5 | n.d. | n.d. |
| | TWN 366 | Mosq. v4181 | — | 7.9 | 8 | 0.1 | ≦100 | 11 ± 3.7 | n.d. | n.d. |
| | TWN 367 | Mosq. v4195 | — | 7.7 | 7.9 | 0.2 | ≦100 | 7.2 ± 1.3 | n.d. | n.d. |
| | TWN 378 | Bird 2071 | — | 8 | 7.9 | 0.1 | ≦100 | 8.4 ± 1.2 | n.d. | n.d. |
| | TWN 379 | Bird 2073 | — | 7.4 | 7.6 | 0.2 | ≦100 | 8.1 ± 2.0 | n.d. | n.d. |
| | TWN 382 | Mosq. v4369 | sp | 7.1 | 5.3 | 1.8 | ≧1,000 | n/a | 0.1 | 5.8 ± 0.4 |
| | TWN 383 | Mosq. v4380 | mixed | 6.6 | 6.3 | 0.3 | ≧100 | n/a | n.d. | n.d. |
| | TWN 399 | Bird 2066 | — | 7.8 | 7.7 | 0.1 | ≦100 | 7.2 ± 0.6 | n.d. | n.d. |
| | TWN 400 | Bird 2067 | — | 7.5 | 7.1 | 0.4 | ≦100 | 7.1 ± 0.2 | n.d. | n.d. |
| | TWN 401 | Bird 2075 | — | 7.9 | 7.7 | 0.2 | ≦100 | 7.0 ± 1.3 | n.d. | n.d. |
| | TWN 402 | Bird 1556 | — | 7.5 | 7.3 | 0.2 | ≦100 | 7.8 ± 2.0 | n.d. | n.d. |
| | TWN 404 | Bird 1881 | mixed | 6.4 | 7 | 0.3 | ≧1,000 | n/a | n.d. | n.d. | sp = small plaque size at 37° C.; small plaques have a diameter of <1.0 mm compared to plaque diameter of 1.5-2.0 mm in Vero cells.

mixed = both small and large plaques measured

Δ = Change in titer ($\log_{10}$ PFU/ml) at 39.5° C. compared to titer at permissive temperature (37.0° C.).

Underline indicates >2.5 $\log_{10}$ PFU/ml reduction in titer in Vero cells at 39.5° C. when compared to permissive temperature.

For a dose of $10^3$ PFU of virus; only strains causing mortality in at least 4 of 5 animals have average survival time (AST).

≧1,000 indicates attenuated phenotype.

≧100 = $LD_{50}$ > 100 PFU but <1,000 PFU.

Note.

n.d., not determined

Figure 3:
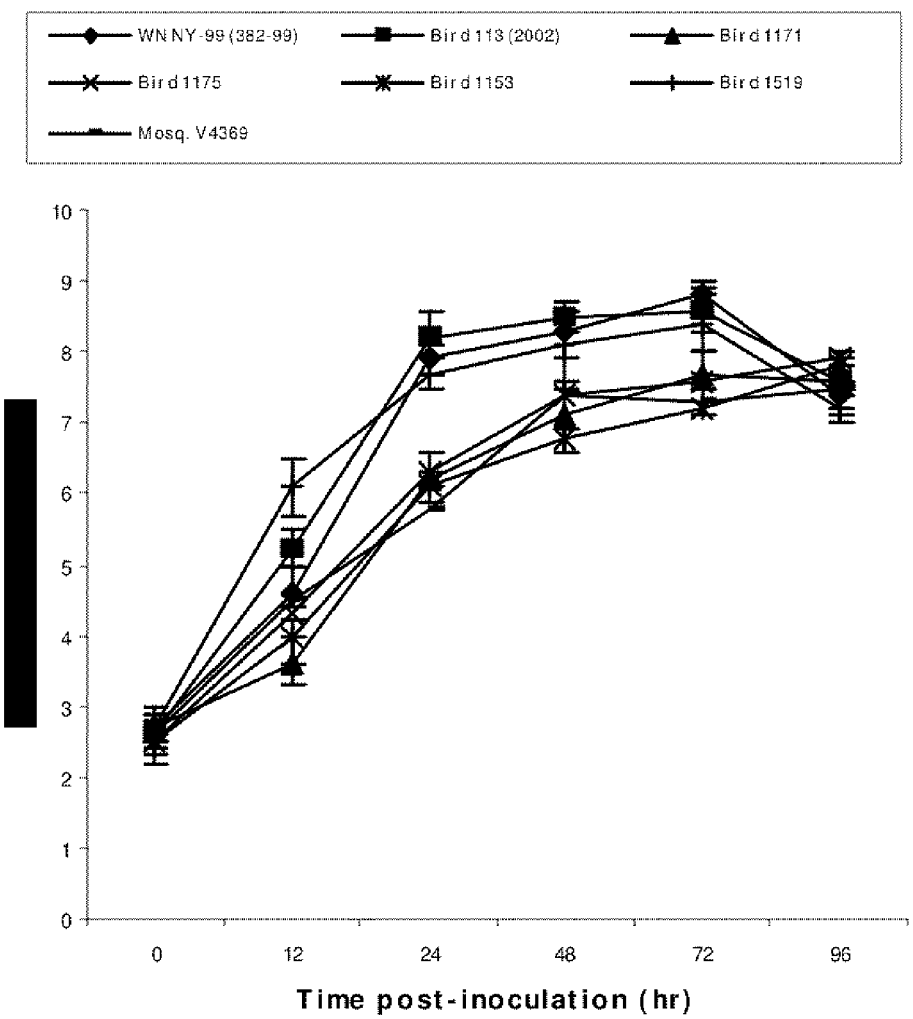
FIG. 3 is a viral growth curve of 2003 sp WNV isolates in comparison to isolates from 1999 and 2002. Vero cells infected with WNV isolates at an MOI of 0.1 PFU/cell in triplicate in 12-well plates. Virus titers were then determined at indicated time points by plaque assay in Vero cells.

Three isolates exhibiting a sp phenotype were identified as also having a ts phenotype, while other sp and non-sp WNV isolates collected during 1999, 2002, and 2003 did not. Following the identification of isolates with sp and/or ts phenotypes, in vitro multiplication studies were done comparing these isolates to WN-NY99 (strain 382-99) and a 2002 large plaque (lp), non-ts Texas WNV isolate (Bird 113). Results from this analysis suggested that viral isolates with sp and/or ts phenotypes have reduced levels of replication in Vero cells at early time points in comparison to WN-NY99 and isolates from 2002 with lp phenotypes (FIG. 3). These isolates also exhibited a 1-2 $\log_{10}$ decrease in viral titer at each time point during the course of infection and did not reach the peak viral titers observed for other WNV isolates at 72 hours postinfection.

Example 2
Mouse Attenuation Phenotypes

The identification of viral isolates exhibiting sp and/or ts phenotypes with reduced replication in cell culture led us to investigate the virulence phenotypes of these isolates, using a mouse model. Small plaque and ts phenotypes have previously been shown to be indicative of attenuation of neuroinvasiveness and neurovirulence in mouse models for many of the encephalitic *flaviviruses* (Hanley et al., 2003; Hanley et al., 2002; Blaney et al., 2003; Puri et al., 1997; Wallner et al., 1996). Consequently, each of the 2003 WNV isolates that were tested for sp and ts phenotypes were also tested for attenuation of neuroinvasiveness and neurovirulence in female 3-4 week-old Swiss Webster mice. Using this model, it has been possible to determine both intraperitoneal (i.e., neuroinvasiveness) and intracranial (i.e., neurovirulence) virulence values of several U.S. WNV isolates collected prior to 2003. Because the intraperitoneal (ip) lethal dose$_{50}$ (LD$_{50}$, which is the dose of virus required to kill half of the animals) of U.S. WNV isolates from 1999 and 2002 ranged from 0.4-4.2 pfu, WNV isolates collected in 2003 were screened for attenuation of neuroinvasiveness by administering intraperitoneal doses of either $10^2$ or $10^3$ pfu of each isolate (Beasley et al., 2003; Table 6). After identification of six isolates that were attenuated for neuroinvasiveness (ip LD$_{50}$≧1,000 pfu), the degree of attenuation of neurovirulence was examined for three of the attenuated isolates (Bird 1153, Bird 1519, Mosquito V4369) by intracranial (ic) inoculation. The results of these studies revealed that isolates attenuated for neuroinvasiveness were not attenuated for neurovirulence (Table 6).

Example 3

Attenuation of Mouse Neuroinvasiveness

In order to establish the degree of attenuation of neuroinvasiveness in a Swiss Webster mouse model, precise neuroinvasiveness for sp and/or ts isolates that exhibited a ≧1,000 pfu LD$_{50}$ was determined. The extent of attenuation of neuroinvasiveness ranged from an ip LD$_{50}$ of 2,000 pfu (Bird 1171) to 645,000 pfu (Mosq.v4369) representing up to 100,000-fold attenuation when compared to the prototypic WNV isolate made in New York in 1999 (Table 7).

TABLE 7

| West Nile virus isolate | Mouse neuroinvasive/neurovirulence phenotypes | | | |
|---|---|---|---|---|
| | ip LD$_{50}$ (PFU) | ic LD$_{50}$ (PFU) | A.S.T. ± s.d. (P) | ip PD$_{50}$ (PFU) |
| WN-NY99 (382-99) | 0.8 | 0.1 | 7.5 ± 0.6 | 1.3 |
| Texas 2002 (Bird 113) | 0.5 | 0.1 | 8.0 ± 1.0 (0.2)* | 1.5 |
| Texas 2003 (Bird 1461) | 0.6 | 0.2 | 7.0 ± 1.0 (0.7)* | 1.2 |
| Texas 2003 (Bird 1153) | 23,000 | 0.3 | 9.5 ± 1.0 (0.12)* | 0.8 |
| Texas 2003 (Bird 1519) | 51,000 | 0.1 | 9.0 ± 4.0 (0.15)* | 0.4 |
| Texas 2003 (Mosquito 4369) | 645,000 | 0.1 | 8.3 ± 3.0 (0.4)* | 0.1 |
| Texas 2003 (Bird 1171) | 2,000 | n.d. | 9.7 ± 3.3 (0.1)* | 1.0 |
| Texas 2003 (Bird 1175) | 10,000 | n.d. | 9.3 ± 6.0 (0.13)* | 0.2 |

A.S.T. ± s.d. (ip) = Average survival time.
ip PD$_{50}$ = the number of pfu required to immunize mice by the ip route to protect against challenge with 100 LD$_{50}$ WN-NY99 (382-99).
P values determine by two-tailed Mann-Whitney test compared to WN-NY99.
Asterisks indicate no significance.
n.d. = not determined Also, the percent mortality following infection with each isolate was greater at higher doses, suggesting the dose-dependent manifestation of encephalitis in this mouse model (data not shown). At 21 days post-inoculation (dpi), surviving mice were challenged with 100 LD$_{50}$ of WN-NY99 (strain 385-99) to measure the dose of each isolate required to protect 50% of mice from death following challenge with a highly neuroinvasive strain (PD$_{50}$). These experiments suggest that attenuated isolates administered at even very low doses ($10^{-1}$ to $10^0$ pfu) are able to induce a protective immune response in the mouse. To test the mechanism by which these isolates were attenuated, serum viremia curves and brain infectivity levels were determined for a single sp, ts, mouse attenuated WNV isolate (Bird 1153) and compared to the levels of viremia in the mouse following parallel infection with WN-NY99. Groups of mice were infected ip with $10^3$ pfu of either WN-NY99 (strain 382-99) or isolate Bird 1153 and three mice from each group were sacrificed daily for 8 days for collection of serum and whole brain preparations. As expected, WN-NY99 followed the typical course of infection of a highly neuroinvasive WNV, whereby serum viremia increased daily following inoculation, peaked at day three, and was followed by the detection of virus in the brain as early as day four and continued until death at day seven-eight (Table 8).

TABLE 8

Serum and brain viremia in mice following ip inoculation of
$10^3$ pfu of WN-NY99 (neuroinvasive) vs. Bird 1153 (non-neuroinvasive)

| Days post inoculation | Animal | WN-NY99 (382-99) Serum titer (pfu/ml) | WN-NY99 (382-99) Brain titer (pfu/brain) | Bird 1153 Serum titer (pfu/ml) | Bird 1153 Brain titer (pfu/brain) |
|---|---|---|---|---|---|
| 1 | 1 | 2,000 | 0 | 3,000 | — |
|   | 2 | 4,000 | 0 | 1,500 | — |
|   | 3 | 1,400 | 0 | 4,000 | — |
| 2 | 1 | 4,000 | 0 | 1,650 | — |
|   | 2 | 11,500 | 0 | 250 | — |
|   | 3 | 1,650 | 0 | 750 | — |
| 3 | 1 | 17,000 | 0 | 100 | — |
|   | 2 | 15,000 | 0 | 100 | — |
|   | 3 | 6,000 | 0 | 250 | — |
| 4 | 1 | — | 2,000 | — | — |
|   | 2 | — | 500 | — | — |
|   | 3 | — | 4,000 | — | — |
| 5 | 1 | — | 3,000 | — | — |
|   | 2 | — | 1,000 | — | — |
|   | 3 | — | 750 | — | — |
| 6 | 1 | — | 135,000 | — | — |
|   | 2 | — | 300,000 | — | — |
|   | 3 | — | 750,000 | — | — |
| 7 | 1 | — | 1,150,000 | n.d. | n.d. |
| 8 | 1 | — | 1,350,000 | n.d. | n.d. |

* indicates no virus detected

Isolate Bird 1153, however, did not produce increased levels of serum viremia following infection. Viral titers remained at levels comparable to the titer of the inoculum for at least 24 hours post-inoculation, but decreased by 48 or 72 hours and became undetectable in the serum by day four. At an ip dose of $10^3$ pfu, no virus was detectable in the brains of these mice at any time post inoculation. These results suggest that attenuation of at least one of the non-neuroinvasive 2003 WNV isolates is due to the inability of the virus to replicate to high levels in the blood sufficient for the invasion of the central nervous system of the mouse.

Example 4

Nucleotide and Deduced Amino Acid Sequence Comparisons

In order to determine those mutations to the WNV genome responsible for the above phenotypic changes, the complete viral genome of 2003 WNV isolate Bird 1153 was sequenced (GenBank Accession No. AY712945 (SEQ ID NO:3)). Phylogenetic comparison of this sequence to all of the other complete genomes of WNV available from GenBank revealed that this isolate is a member of the North American clade of WNV isolates (data not shown). While there were a total of 36 nucleotide mutations in the genome of this virus relative to the prototype WN-NY99 strain, these mutations resulted in only 4 amino acid substitutions in the WNV polyprotein (prM-156, E-159, NS4B-249 and NS5-804) and 4 nucleotide substitutions in the 3'UTR (Table 9). One of the nucleotide changes in the 3' UTR (A10851G) was also identified in the WN-NY99 infectious clone (Beasley et al., 2005).

TABLE 9

Nucleotide Changes and Deduced Amino Acid Substitutions of 2002-2003 Texas WNV
isolates compared to WN-NY99 (AF196835)

| Virus | Plaque size | Temperature sensitivity 37° C.[a] | Temperature sensitivity 41.0° C.[a] | Δ | Mouse neuroinvasiveness and neurovirulence Intraperitoneal inoculation LD50 (PFU) | AST ± s.d. | Intracerebral inoculation LD50 (PFU) | AST ± s.d. |
|---|---|---|---|---|---|---|---|---|
| WN-NY99 (382-99) | lp | 8.1 | 7.6 | 0.5 | 0.8 | 8.0 ± 1.2 | 0.1 | 6.4 ± 0.9 |
| WN-NY99 ic | lp | 7.0 | 7.3 | 0.3 | 1.0 | 7.2 ± 0.6 | 0.4 | 6.0 ± 0.2 |
| Bird 1153 | sp | 7.7 | 4.8 | 2.9\* | 23,000 | n/a | 0.1 | 6.7 ± 0.3 |
| Mosq. V4369 | sp | 7.2 | 6.8 | 0.4 | 645,000 | n/a | 0.2 | 6.2 ± 0.3 |
| NS4B E249G (sp, ts, att) | lp | 6.2 | 6.0 | 0.2 | 1.2 | 7.5 ± 0.4 | 0.1 | 6.0 ± 0.2 |
| prM V156I (sp, ts, att) | lp | 5.9 | 6.1 | 0.2 | 0.7 | 8.6 ± 1.4 | n.d. | n.d. |
| 3'UTR (sp, ts, att) | lp | 6.4 | 5.0 | 1.4\* | 0.6 | 8.8 ± 2.0 | n.d. | n.d. |
| prM V156I + NS4B E249B (sp, ts, att) | lp | 7.0 | 7.2 | 0.2 | 1.4 | 8.8 ± 1.5 | n.d. | n.d. |
| prM V156I + 3'UTR (sp, ts, att) | lp | 6.6 | 5.1 | 1.5\* | 4.2 | 9.0 ± 1.0 | n.d. | n.d. |
| NS4B E249B + 3'UTR (sp, ts, att) | sp | 5.0 | 3.2 | 1.8\* | >10,000 | n/a | n.d. | n.d. |
| NS4B E249B + NS5 A804V (sp, ts, att) | sp | 6.2 | 6.4 | 0.2 | 2,000 | 9.2 ± 1.2 | n.d. | n.d. |

TABLE 9-continued

Nucleotide Changes and Deduced Amino Acid Substitutions of 2002-2003 Texas WNV isolates compared to WN-NY99 (AF196835)

| Virus | Plaque size | Temperature sensitivity | | | Mouse neuroinvasiveness and neurovirulence | | | |
|---|---|---|---|---|---|---|---|---|
| | | | | | Intraperitoneal inoculation | | Intracerebral inoculation | |
| | | 37° C.[a] | 41.0° C.[a] | Δ | LD50 (PFU) | AST ± s.d. | LD50 (PFU) | AST ± s.d. |
| prM N4D (sp, att) | lp | 7.3 | 7.1 | 0.2 | 1.2 | 9.4 ± 1.6 | n.d. | n.d. |
| NS4B T240A + NS5 H295Y (sp, att) | lp | 5.9 | 6.1 | 0.2 | 0.7 | 7.3 ± 0.5 | n.d. | n.d. |

Small plaque (sp) morphology = <1.0 mm (shown as bold/underlined)
Large plaque (lp) morphology = >1.5 mm
[a]$Log_{10}$ Plaque titer at each temperature (pfu/ml)
Δ = difference in plaque titer at 37.0 and 41.0
ts = temperature-sensitivite phenotype at 41.0° C. (shown as bold/italics)
att = attenuated for mouse neuroinvasiveness (shown in bold)
3'UTR = A10596G, C10774U, A10799G, and A10851G
P values were calculated versus average non-ts plaque titer reduction by Student t-Test;
*Indicates statistical significance.

In order to identify nucleotide/amino acid substitutions shared by sp, ts, and/or attenuated isolates, each of the genes/regions of isolate Bird 1153 containing amino acid substitutions or nucleotide mutations in the case of the 3'UTR was sequenced in other isolates with a sp, ts, and/or attenuated phenotype. Table 8 shows the distribution of mutations among WNV isolates from 2002 and 2003 in comparison to WN-NY99 in those genes/regions where mutations were identified in the completely sequenced isolate. While several conserved mutations were identified among isolates from both 2002 and 2003, a single amino acid substitution (NS4B-E249G) was found to be conserved in three isolates with a sp, ts, and mouse attenuated phenotype (Bird 1153, Bird 1171, Bird 1175). Although this mutation was not identified in all attenuated 2003 isolates, in specific embodiments the substitution in NS4B was responsible for the altered phenotype(s) of these three isolates. Comparisons of this particular amino acid substitution between other North American WNV isolates revealed that no other isolates described to date contained this mutation. It is interesting to note that several Old World WNV isolates (i.e., Volgograd, Romania, Italy) contain different amino acid substitutions other than E→G at residue 249 of NS4B (Lanciotti et al., 2002).

Because the complete genome sequence of Bird 1153 did not reveal a single nucleotide/amino acid substitution shared only by sp and/or attenuated isolates, it indicated that multiple mutations were responsible for the range of phenotypes identified, in some embodiments of the invention. Therefore, the complete genomes of three other 2003 WNV isolates (Bird 1461, GenBank accession No. AY712947 (SEQ ID NO:5); Bird 1171, GenBank accession No. AY712946 (SEQ ID NO:4); and Mosquito V4369, GenBank accession No. AY712948 (SEQ ID NO:6)) were sequenced and compared to WN-NY99 (382-99) to identify additional mutations that were likely to be responsible for the phenotypes (Table 9).

With the exception of E-V159A, nucleotide mutations in the genome of Bird 1461 (large plaque, non-ts, non-attenuated) encoded four unique amino acid substitutions compared with sp, ts, and/or attenuated isolates (NS3-E180D; NS3-E327K; NS4A-V134M; NS5-A618S). The genome sequence of Bird 1171 (sp, ts, and attenuated) was nearly homologous to that of Bird 1153 with two additional amino acid substitutions (NS5-R199L; NS5-A687D) and one additional substitution in the 3'UTR (G→U at residue 11000). Mosquito V4369 (sp, non-ts, attenuated) also shared the E-V159A amino acid substitution and the 3'UTR nucleotide change at residue 10851, but this isolate revealed three additional amino acid substitutions (prM-N4D; NS4B-T240A; NS5-H295Y) and an additional nucleotide change in the 3'UTR (A→U at residue 10984). The prM-N4D substitution found in Mosquito V4369 was shared by another sp, non-ts, attenuated isolate, Bird 1519, indicating its role in the altered phenotype(s) of these two isolates, inspecific embodiments.

Example 5

Figure 4:
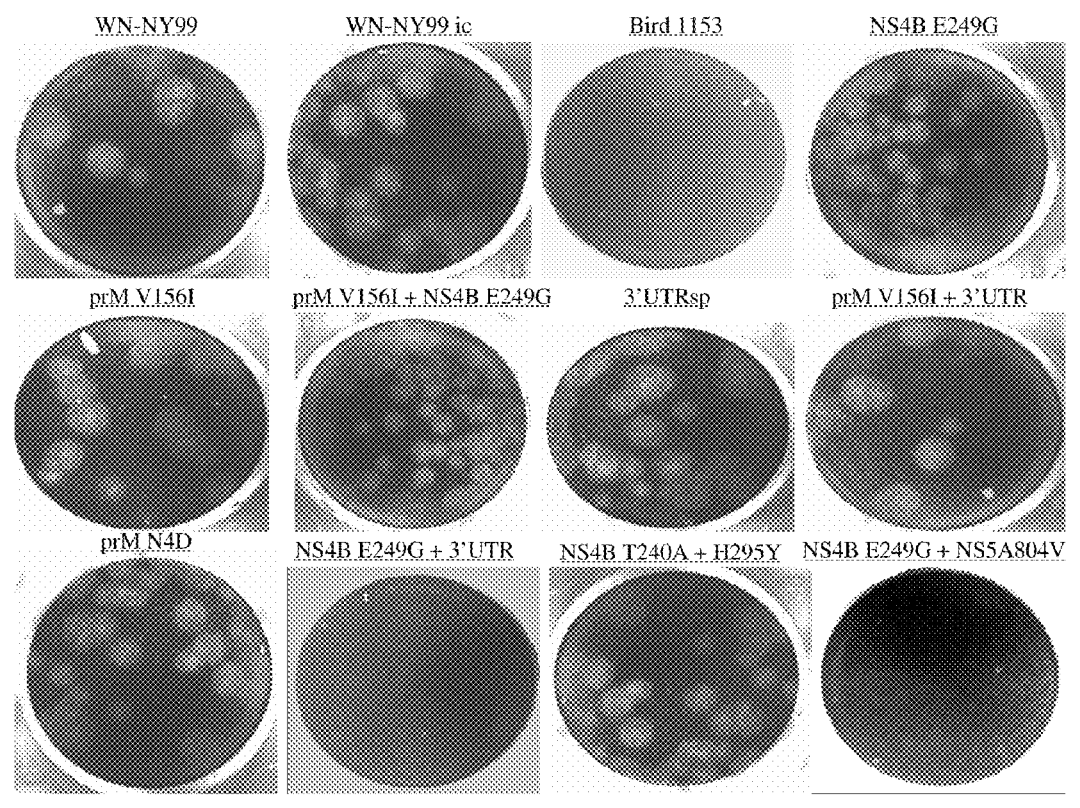
Figure 8:
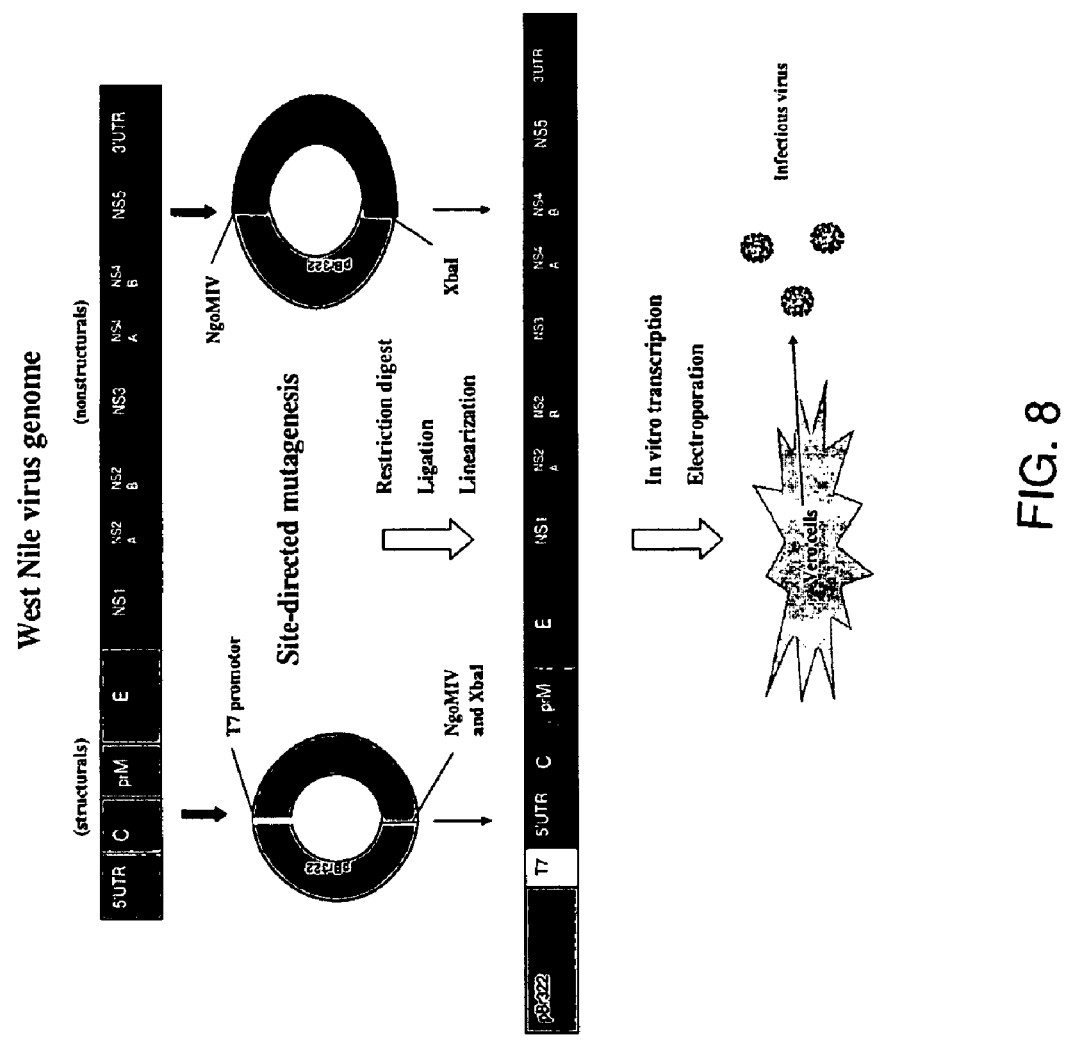

Site-Directed Mutagenesis of West Nile Virus, WN-NY99, INFECTIOUS Clone and Infectious Virus Rescue A WNV infectious clone was obtained from Dr. Richard Kinney of CDC, Ft. Collins. The QuikChange® XL Site-Directed Mutagenesis Kit was used to mutate the pWN-CG plasmid containing the 3' half of the WNV genome to alter amino acid residue 249 of NS4B from Glu to Gly as described in Example 10 (FIG. 8). Infectious virus recovered from transfected Vero cells was aliquoted into ampoules containing 0.5 ml of supernatant. Viral RNA extracted from supernatant was amplified by RT-PCR using primers specific for the region containing the NS4B mutation to confirm the presence of the desired mutation. Plaque morphology and ts assays were performed and revealed the rescued virus to be a lp, non-ts variant (FIG. 4, Table 10). Lethality experiments comparing the NS4B E249G mutant to the NY99 infectious clone demonstrated that this mutant had the highly mouse neuroinvasive phenotype with an ip $LD_{50}$ of 1.0 PFU.

TABLE 10

Mutant infectious clone derived viruses and their phenotypic properties

| Virus | Plaque size | Temperature sensitivity | | | Mouse neuroinvasiveness and neurovirulence | | | |
|---|---|---|---|---|---|---|---|---|
| | | | | | Intraperitoneal inoculation | | Intracerebral inoculation | |
| | | 37° C.[a] | 41.0° C.[a] | Δ | LD50 (PFU) | AST ± s.d. | LD50 (PFU) | AST ± s.d. |
| WN-NY99 (382-99) | lp | 8.1 | 7.6 | 0.5 | 0.8 | 8.0 ± 1.2 | 0.1 | 6.4 ± 0.9 |
| WN-NY99 ic | lp | 7.0 | 7.3 | 0.3 | 1.0 | 7.2 ± 0.6 | 0.4 | 6.0 ± 0.2 |
| Bird 1153 | sp | 7.7 | 4.8 | *2.9 | 23,000** | n/a | 0.1 | 6.7 ± 0.3 |
| Mosq. V4369 | sp | 7.2 | 6.8 | 0.4 | 645,000 | n/a | 0.2 | 6.2 ± 0.3 |
| NS4B E249G (sp, ts, att) | lp | 6.2 | 6.0 | 0.2 | 1.2 | 7.5 ± 0.4 | 0.1 | 6.0 ± 0.2 |
| prM V156I (sp, ts, att) | lp | 5.9 | 6.1 | 0.2 | 0.7 | 8.6 ± 1.4 | n.d. | n.d. |
| 3'UTR (sp, ts, att) | lp | 6.4 | 5.0 | *1.4** | 0.6 | 8.8 ± 2.0 | n.d. | n.d. |
| prM V156I + NS4B E249G (sp, ts, att) | lp | 7.0 | 7.2 | 0.2 | 1.4 | 8.8 ± 1.5 | n.d. | n.d. |
| prM V156I + 3'UTR (sp, ts, att) | lp | 6.6 | 5.1 | *1.5** | 4.2 | 9.0 ± 1.0 | n.d. | n.d. |
| NS4B E249G + 3'UTR (sp, ts, att) | sp | 5.0 | 3.2 | *1.8 | >10,000** | n/a | n.d. | n.d. |
| NS4B E249G + NS5 A804V (sp, ts, att) | sp | 6.2 | 6.4 | 0.2 | 2,000 | 9.2 ± 1.2 | n.d. | n.d. |
| prM N4D (sp, att) | lp | 7.3 | 7.1 | 0.2 | 1.2 | 9.4 ± 1.6 | n.d. | n.d. |
| NS4B T240A + NS5 H295Y (sp, att) | lp | 5.9 | 6.1 | 0.2 | 0.7 | 7.3 ± 0.5 | n.d. | n.d. |

Small plaque (sp) morphology = <1.0 mm (shown as bold/underlined)
Large plaque (lp) morphology = >1.5 mm
[a]$Log_{10}$ Plaque titer at each temperature (pfu/ml)
Δ = difference in plaque titer at 37.0 and 41.0
ts = temperature-sensitivite phenotype at 41.0° C. (shown as bold/italics)
att = attenuated for mouse neuroinvasiveness (shown in bold)
3'UTR = A10596G, C10774U, A10799G, and A10851G
P values were calculated versus average non-ts plaque titer reduction by Student t-Test;
*Indicates statistical significance.

Because the NS4B E249G mutant did not produce any of the phenotypes found in the field variants, additional mutant viruses were generated by incorporating several combinations of amino acid mutations and 3'UTR nucleotide mutations in both the pWN-AB and CG plasmids (i.e., 5' half and 3' half of the WNV genome, respectively (Table 10). In order to incorporate 3'UTR mutations found in the sp, ts, and attenuated isolates, a complete 3'UTR exchange was made between the NY99 infectious clone and Bird 1153, as described in Example 10. All of the engineered mutations and 3'UTR exchanges in the infectious clone pWN-AB and pWN-CG plasmids were confirmed by nucleotide sequencing of the modified plasmids in the regions containing the desired mutation(s). Transcription and transfection reactions were carried out as described in Example 10. Sequences of primers used for mutagenesis are shown in Table 11.

TABLE 11

Exemplary Mutagenic Primers used for Site-directed Mutagenesis

NS4B E249G (sp, ts, att)

7645 For
(SEQ ID NO:7)
CTCATAAAGAACATGGAAAACCAGGACTAAAAAGAGGTGGGGC

7689 Rev
(SEQ ID NO:8)
GCCCCACCTCTTTTTAGTCCTGGTTTTCCCATGTTCTTTATGAG prM V156I (sp, ts, att)

915 For
(SEQ ID NO:9)
GCAGAGAGTTGTGTTTATCGTGCTATTGCTTTTGGTGGCCCCAGC

959 Rev
(SEQ ID NO:10)
GCTGGGGCCACCAAAAGCAATAGCACGATAAACACAACTCTCTGC

TABLE 11-continued

Exemplary Mutagenic Primers used for Site-directed Mutagenesis prM N4D (sp, att)

451 For
(SEQ ID NO:11)
GCCAGCGTAGGAGCAGTTACCCTCTCTGACTTCCAAGGGAAGG

493 REV
(SEQ ID NO:12)
CCTTCCCTTGGAAGTCAGAGAGGGTAACTGCTCCTACGCTGGC

NS4B T240A (sp, att)

7636 For
(SEQ ID NO:13)
GGT TGG TTG TCA TGT CTA TCC ATA GCA TGG ACA CTC

7636 Rev
(SEQ ID NO:14)
GAG TGT CCA TGC TAT GGA TAG ACA TGA CAA CCA ACC

NS5 H295Y (sp, att)

8566 For
(SEQ ID NO:15)
CGT GAG TAC AGT TCG ACG TGG CAC TAC GAT GAG AAC CAC CC

8566 Rev
(SEQ ID NO:16)
GG GTG GTT CTC ATC GTA GTG CCA CGT CGA ACT GTA CTC ACG

TABLE 11-continued

Exemplary Mutagenic Primers used for Site-directed Mutagenesis

NS5 A804V (sp, ts, att)

10091 For
(SEQ ID NO:17)
CCA CGT GGT CCA TCC ATG TAG GAG GAG AGT GG

10091 Rev
(SEQ ID NO:18)
CC ACT CTC CTC CTA CAT GGA TGG ACC ACG TGG

Example 6

Phenotypic Characterization of WN-NY99 Infectious Clone-Derived Virus

A total of nine mutant viruses were constructed that incorporated mutations found in field isolates from Texas in 2003 that possessed phenotypic variation from the typical North American WNV (Table 10). Following rescue of infectious virus from transfected Vero cell cultures, viral supernatants were used for plaque titration, plaque morphology assays, and ts assays. All mutant viruses had plaque titers of $\geq 1.0 \times 10^{04}$ pfu/ml. Plaque morphology was visualized by crystal violet staining of 6-well plates after 3 dpi using WN-NY99 to control for variation in plaque size. Two mutant viruses were found to have a sp phenotype (NS4B E249G+3UTR and NS4B E249G+NS5A804V), while all others displayed a typical lp morphology (FIG. 4). Only mutants containing the 3'UTR from the sp, ts, att isolates (Bird 1153) were found to be ts, although the degree of temperature sensitivity at 41.0° C. was not as significant in comparison to ts field isolates (P<0.05 for each mutant ts isolate; P<0.001 for ts field isolates versus non-ts plaque titer reduction by Student's t-Test).

Example 7

Phenotypic Characterization of Infectious Clone Derived Mutants

Preliminary experiments revealed that the infectivity titers of virus derived from the infectious clone prior to site-directed mutagenesis were similar to those generated by inoculating cell cultures with wild-type WNV. Experiments also compared the mouse neuroinvasive/neurovirulence phenotypes of the parental strain WN-NY99 with virus derived from the infectious clone and found that both viruses have an ip $LD_{50}$ of approximately 1.0 PFU and an ic $LD_{50}$ ranging from 0.1 to 0.4 PFU (Table 10). Thus, the infectious clone derived virus is representative of the prototypical U.S. WNV strain from which the infectious clone was derived in its mouse neuroinvasive/neurovirulence phenotype and plaque morphology (FIG. 4) and serves as an appropriate genetic backbone with which to incorporate mutations of interest.

Lethality experiments involving intraperitoneal inoculation in the Swiss Webster mouse model revealed that both sp mutant viruses (NS4B E249G+3UTR and NS4B E249G+NS5A804V) were highly attenuated for mouse neuroinvasion (LD50=>10,000 pfu and 2,000 pfu, respectively). Interestingly, incorporation of each point mutation alone, or even an entire exchange of the 3'UTR from the sp, ts, att isolate into the NY99ic, exhibited a highly neuroinvasive phenotype. All other mutant viruses produced ip LD50 survival time values similar to wild-type NY99 and the NY99 infectious-clone derived virus.

Example 8

Multiplication Kinetic Studies

Figure 5:
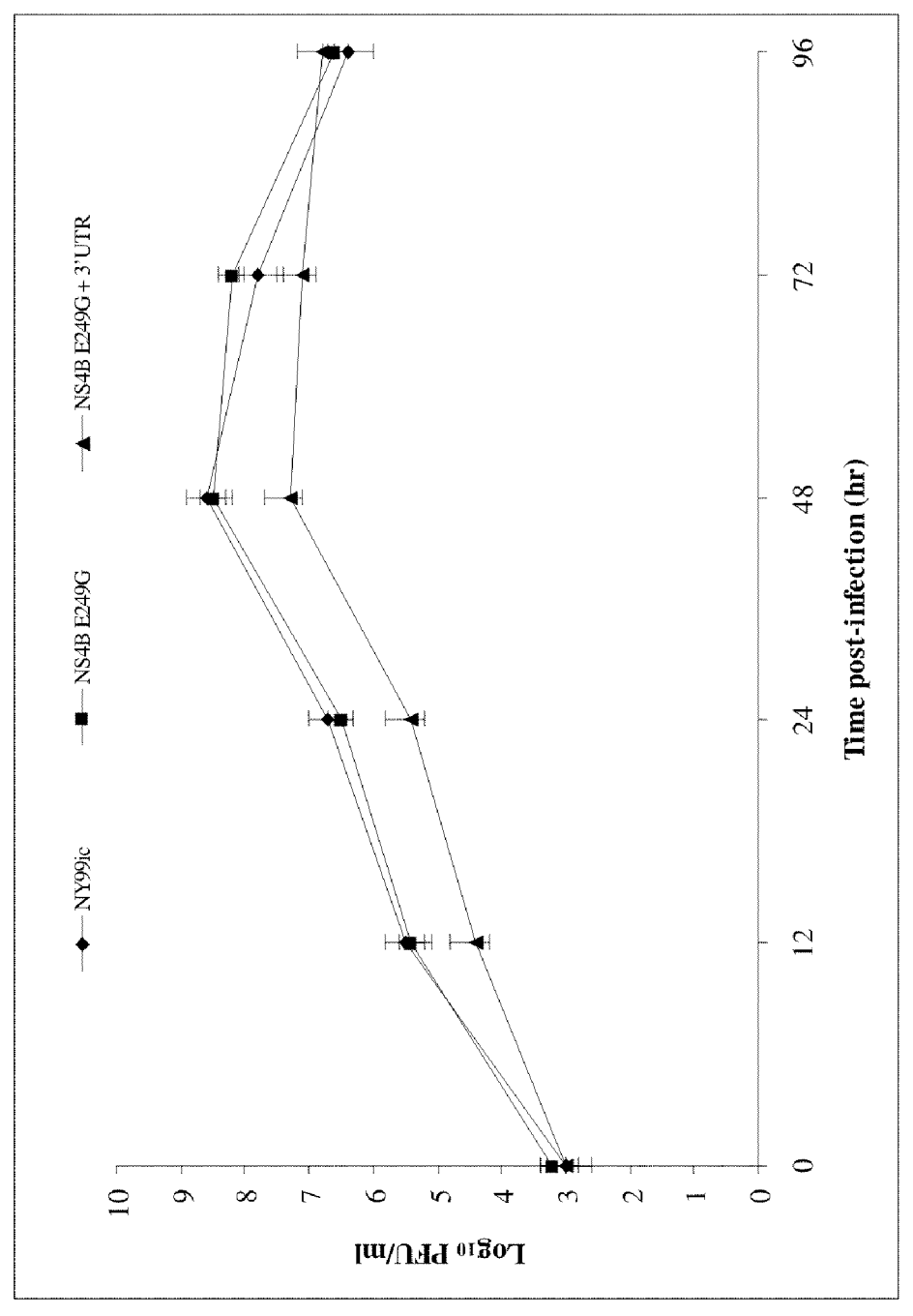

In order to measure the multiplication characteristics of the attenuated mutant viruses, Vero cells were infected in triplicate at an MOI of 0.1 pfu/cell in 12-well plates with NY99ic, NS4B E249G+3'UTR (att), and NS4B E249G (non-att). FIG. 5 shows the viral growth curve of each virus at various time points. While both NY99ic and NS4B E249G derived viruses reached titers as high as 8.5 $\log_{10}$ pfu/ml, the sp, ts, att NS4BE249G+3'UTR mutant failed to reach infectivity titers of greater than 7.0 $\log_{10}$ pfu/ml suggesting that this mutant has reduced levels of replication in Vero cells in comparison to prototypical WNV isolates. Additionally, there was an approximately 10-fold decrease in viral titers at many of the time points (12-72 hours), a finding that suggests inefficient replication at all time points post-infection.

Example 9

Significance of the Present Invention

The emergence of phenotypic variants of WNV in Texas in 2003 led to an investigation to identify those mutations responsible and to understand how the mutations affected the phenotypic characteristics of WNV. By sequencing the complete genomes of several phenotypic variants of the North American WNV genotype and incorporating the identified mutations into the NY99 infectious clone, this study has identified several mutations in the WNV genome that reduce viral multiplication in vitro, confer temperature-sensitivity, and attenuate the ability of the virus to induce encephalitic disease in a mouse model. It was hypothesized that a single point mutation in the viral nonstructural protein NS4B would be responsible for imparting the sp, ts, and/or att WNV phenotype, however, this study has demonstrated that a combination of either single point mutations resulting in amino acid substitutions or nucleotide mutations in the 3'UTR were responsible for the previously described phenotypic variation. This study demonstrates that a point mutation at residue 249 of the NS4B protein from a Glu to Gly in combination with a mutation in the NS5 protein at residue 804 (Ala to Val) or with three mutations to the viral 3'UTR (A10596G, C10774U, and A10799G) produce variants with sp, ts, and/or mouse attenuated phenotypes. Interestingly, the NS4B E249G mutation alone did not alter the phenotype of the infectious clone suggesting that the phenotypic variation observed in the field isolates was the result of more than one mutation to the viral genome. Additionally, evidence from ts mutants containing the 3'UTR exchange suggests that the ts phenotype is encoded by the 3'UTR but may be the result of more than a single nucleotide mutation in the 3'UTR. The requirement of multiple mutations to modify the phenotype of the North American WNV variants may explain why such variants are rarely isolated.

Figure 6:
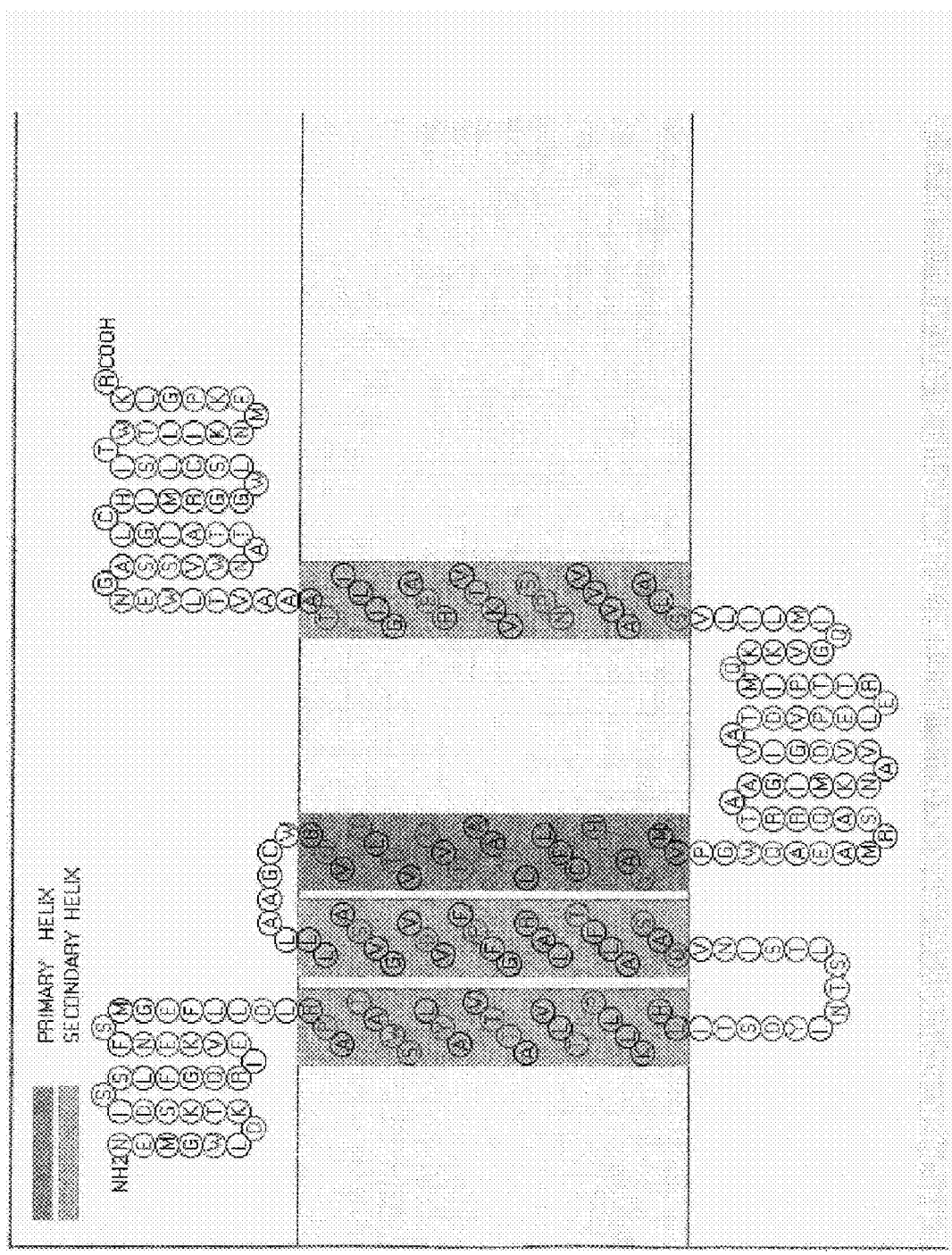
FIG. 6 illustrates a predicted hydrophobicity plot of the NS4B protein generated by the SOSUI program. The location of the NS4B E249G amino acid alteration (denoted by arrow) was predicted to reside in the lumenal C-terminal tail of the WNV NS4B protein SEQ ID NO:70 (courtesy of J. Wicker, unpublished).

The NS4B protein of WNV is of unknown function and inferences concerning the influence of the E249G mutation remain speculative at best. However, previous studies of WNV and other closely related *flaviviruses* have shown this protein to be important to viral replication and pathogenesis. Westaway and others have described the accumulation of Kunjin virus NS4B protein the perinuclear region of infected cells and the ability of NS4B to translocate to the nucleus (Westaway et al., 1997). A live, attenuated vaccine strain (SA14-14-2) of Japanese encephalitis virus possesses an amino acid substitution in NS4B thought to be important in viral pathogenesis (Ni et al., 1995). Studies by Hanley and others have identified NS4B mutations that influence the susceptibility of SCID mice to dengue-4 virus infection (Hanley et al., 2003). Also, a mutation to the NS4B protein of dengue-2 virus has been associated with changes in the ability of the virus to inhibit the interferon-signaling cascade, presumably by blocking STAT-1 phosphorylation (Munoz-Jordan et al., 2005). It is interesting to note that several Old World WNV isolates (e.g., Volgograd, Romania, Italy) contain different amino acid substitutions other than E to G at residue 249 of NS4B (Lanciotti et al., 2002). Also, a recent study by Rossi et al. (2004) identified the same mutation in a West Nile virus replicon that had established a persistent infection in different mammalian cell lines. Predictive structural models of this protein suggest that residue 249 is located in the carboxy-terminal portion of the protein in a region of the lumenal tail suggesting that this residue may form an interaction with components of the WNV replication complex or with other viral or cellular proteins (FIG. 6). In specific embodiments of the invention concerning the functional role of NS4B, amino acid substitutions to the protein destabilize the conformation of the protein by disrupting bonds between amino acids important to protein stability or function.

Figure 7:
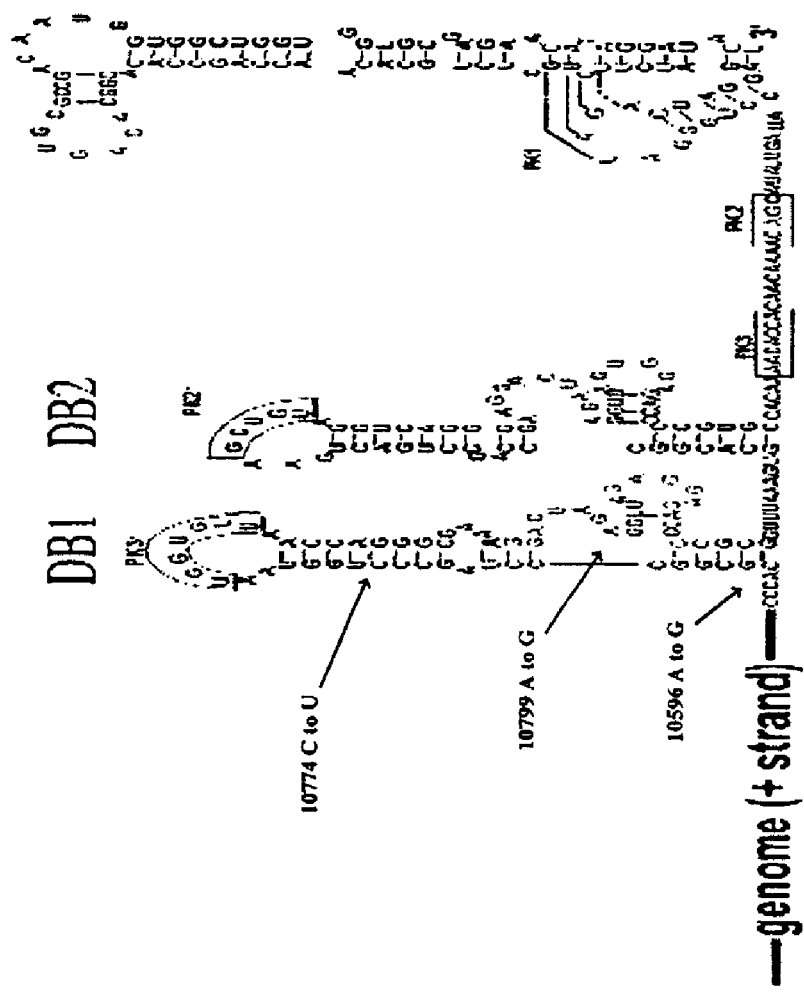
FIG. 7 illustrates predicted secondary structure of WNV 3'UTR (SEQ ID NO:71) showing the location of nucleotide point mutations in sp, ts, att isolates. DB1 and DB2: dumbbell 1 and 2 (adapted from Brinton, 2002).

Embodiments of the present invention also indicate that mutations in the 3'UTR play a role in the generation of virus variants with a temperature-sensitive phenotype. All three mutant viruses exhibiting a ts phenotype possessed a 3'UTR gene swap from Bird 1153 (sp,ts,att). Genetic analysis showed that the 3'UTR contained three nucleotide mutations in comparison to NY99 each of which were located in or near the 5' stemloop structure (dumbbell-1; DB1) of the 3'UTR (FIG. 7). The mapping of these mutations to a 3'UTR DB1 suggests their involvement in maintaining the secondary structure of the DB1, which in previous studies has been shown to be important for maintaining the function of the 3'UTR (Tilgner et al., 2005). Studies have shown that deletions and mutations of conserved nucleotides in any one of the three stemloop structures predicted in the WNV 3'UTR reduced the replication efficiency of the mutant viruses produced (Brinton, 2002). In studies of dengue-4 and tick-borne encephalitis viruses, 3'UTR mutants have been highly attenuated with impaired growth characteristics (Proutski et at, 1999; Mandl et at, 1998). It has been proposed that mutations/deletions to the dumbbell structures lead to a structural rearrangement of the dumbbell directly or to pseudoknots located at the tips of the predicted dumbbells (See FIG. 7). Consequently, in specific embodiments this disrupts the ability of the stemloop to stabilize and compartmentalize the replication complex during viral replication or to form binding sites for viral or cellular proteins important for replication or RNA synthesis (Brinton, 2002). Interestingly, the mutation at nucleotide 10799 is located in a region of the 5' dumbbell that is highly conserved in the *Flavivirus* genus, known as conserved sequence 2 (CS2). Although the function of this region remains unknown, it has been suggested that the CS2 region is involved in viral replication (Markoff, 2003). Mutation of a C to U at nucleotide 10774 is also of interest because of the possibility that this change may influence proper base pairing and folding patterns of the DB1 stemloop structure. The mutation at nucleotide 10596 is less likely to influence the structure of the 3'UTR because it is found outside of the conserved stemloop region. Regardless, in particular aspects of the invention the ts phenotype of isolates containing these mutations are the result of alterations to the 3'UTR secondary structure, rendering the dumbbell structure sensitive to high temperature conditions. Under these conditions, in specific embodiments the function of the dumbbell region is impaired, resulting in reduced replication. While in particular embodiments of the invention the mutations in the 3'UTR influence temperature-sensitivity, the 3'UTR mutations alone did not attenuate the infectious clone-derived virus, indicating that these mutations alone do not alter viral replication under the physiological conditions of the mouse model.

In addition to mutations in the 3'UTR, a sp and mouse attenuated mutant was generated with a substitution at residue 804 in the NS5 protein along with the NS4B substitution. The NS5 gene of WNV encodes a single protein believed to possess both an N-terminal region with methyltransferase activity and a C-terminal region with RNA-dependent RNA polymerase (RdRp) activity. The NS5 A804V mutation is located in the C-terminal region of the protein, but is found outside of any of the conserved motifs previously described as important to RdRp activity (Ackermann and Padmanabhan, 2001). The presence of a mutation in this region that results in a sp and mouse attenuated viruses indicates that the Ala at residue 804 is important for the activity of the RdRp, in specific embodiments of the invention. This hypothesis warrants further investigation as the growth kinetics of the NS5 A804V mutant in cell culture have not been performed. More detailed analyses of the consequences of this mutation on polymerase function are required.

Despite the identification of several multi-site mutations that impart the sp, ts, and mouse attenuated phenotypes observed in WNV field isolates, it is clear from genomic sequencing of variant viruses (e.g., Mosq. v4369) that additional mutations resulting in sp and attenuated mutants were not found. Even though several mutations from the Mosq. v4369 were incorporated into the NY99ic, no mutant viruses were produced that had a sp or attenuated phenotype. Additional studies of infectious clone mutants will be required to further characterize other mutations in the viral genome that may result in phenotypic variation in WNV.

Example 10

Exemplary Materials and Methods

Collection of Isolates

Dead birds and mosquitoes were collected by the Harris County Mosquito Control Division from Harris and Montgomery Co., Tex. during the summer of 2003. Virus isolations were made by inoculation of bird brain or mosquito homogenates on Vero cells as described elsewhere (Lillibridge et al, 2004). Upon confirmation that isolates were WNV positive by either hemagluttination inhibition assay or RT-PCR, each isolate was passaged once in Vero cells to derive virus for use in these studies and was submitted to the World Reference Center for Emerging Viruses and Arboviruses at the University of Texas Medical Branch.

Small Plaque (sp) Morphology and Temperature-Sensitivity (ts) Assays

In order to establish the plaque morphology and ts phenotypes of isolates collected in 2003, plaque assays were carried out by infecting monolayer cultures of Vero cells (ATCC) in 6-well plates with serial dilutions of WNV isolates. All plaque assays were run in parallel with WN-NY99 (strain 382-99) as a control. Each isolate was grown at both 37.0° C. and 39.5° C. for 72 hours to measure temperature-sensitivity, plaque morphology, and plaque titer. At 72 hours post-infection, wells were stained with crystal violet to visualize plaques. The small plaque (sp) phenotype was described as a <1.0 mm plaque diameter whereas large plaque (lp) WNV was >1.5 mm in plaque diameter. The ts phenotype was described as a ≧2.5 log10 reduction in infectivity titer determined in Vero cell plaque assay at 39.5° C. when compared to permissive temperature 37.0° C.

Mouse Attenuation Studies

Screening WNV isolates for attenuation of neuroinvasiveness was performed by intraperitoneal (ip) inoculation of groups of five female 3-4 week-old Swiss Webster mice with 100 µl of $10^2$ and $10^3$ pfu of virus. WN-NY99 (isolate 385-99)

was used as a positive control; mice inoculated with saline served as negative controls. Mice were evaluated daily for signs of illness (ruffled fur, hunched posture, lethargy, ocular or nasal discharge, hindlimb/forelimb paralysis) or death. All deaths occurred between twice-daily observations. At 21 days post-inoculation (dpi) surviving mice were challenged with 100 LD50 of WN-NY99 (385-99) to ensure that replication of virus had occurred in each mouse inoculated, as indicated by protection following challenge with a lethal dose. In order to determine if isolates that were attenuated in neuroinvasiveness were also attenuated for neurovirulence, attenuated isolates (20 μl) were inoculated intracerebrally into groups of five female 3-4 week-old Swiss Webster mice at dosages of $10^3$ to $10^{-1}$ pfu of virus. Severe illness and/or death were the end-points as before. All procedures with animals were carried out according to guidelines of the Committee on Care and Use of Laboratory Animals under an animal-care protocol approved by the University of Texas Medical Branch. All work with infected animals and virus was carried out in Biosafety Level 3 facilities.

Determination of Mouse LD50 Values

In order to establish the extent of attenuation of neuroinvasiveness in a Swiss Webster mouse model, a precise LD50 for WNV isolates that exhibited a ≧1,000 pfu LD50 was determined. This was done by intraperitoneal (ip) inoculation of groups of five female 3-4 week-old Swiss Webster mice with 100 μl of serial ten-fold dilutions of virus from 106 to 10-1 pfu of virus. WN-NY99 (385-99) was used as a positive control. Mice were evaluated for signs of illness or death, as before. At 21 days post-inoculation (dpi), surviving mice were challenged with 100 LD50 of WN-NY99 (385-99) to ensure replication of virus and to calculate the dose that protects 50% of mice from death against a lethal challenge of WN-NY99 (PD50).

Viremia Kinetics and Brain Infectivity Levels of an Attenuated WNV Isolate

The 3-4 week-old Swiss Webster mouse model was used to compare the viremia and brain infectivity levels of an attenuated WNV isolate to the highly neuroinvasive WNV isolate, WN-NY99. Two groups of 24 mice were infected ip with 100 μl of $10^3$ pfu of either WN-NY99 (385-99) or an attenuated 2003 WNV isolate (Bird 1153) and monitored daily for signs of illness. Following infection, three mice from each of the two groups were bled daily for eight days and serum samples were titrated, using standard Vero cell viral plaque assays in six well plates. Briefly, animals were bled daily by cardiac puncture after euthanasia in order to recover at least 2 ml of whole blood. Blood was allowed to clot and then centrifuged; the serum was extracted and diluted $10^{-1}$ to $10^{-6}$ for titration by plaque assay. Virus titers in brain were measured daily by removing the entire brain from each of three euthanized mice, followed by homogenization in 2% MEM. Brain homogenates were then diluted $10^{-1}$ to $10^{-6}$ for titration by plaque assay. Virus titers in blood and brain at each time interval were measured in three mice and the averages of these were used to construct a viremia and brain infectivity curve. These results were compared to a viremia curve and brain infectivity curve for WN-NY99, which was performed in parallel under the same experimental conditions. All procedures were carried out according to guidelines of the Committee on Care and Use of Laboratory Animals under an animal-care protocol approved by the University of Texas Medical Branch. All work with infected animals and virus was carried out in Biosafety Level 3 facilities.

RNA Extraction, Reverse Transcription (RT), and PCR for Genome Sequencing

Viral RNA was extracted directly from 140 μL of infected Vero or BHK cell culture supernatants using the QiaAMP viral RNA extraction kit (Qiagen). RT was performed in a 50 μL volume containing 5 μL of viral RNA, 1 mL of random hexamer primer, 10 μL of 5×RT buffer, 4 μL of 10 mM dNTPs, 0.4 μL of cloned RNAse inhibitor, 0.5 μL of Moloney murine leukemia virus (MMLV) reverse transcriptase, and 29.1 μL of HPLC water. PCR was performed in a 25 μL volume containing 2.0 μL cDNA template from RT, 1.0 μL forward primer, 1.0 μL reverse primer, 2.5 μL 10×PCR buffer, 0.5 μL 10 mM dNTPs, 0.5 μL of 1 U/μL Taq polymerase, and 17.5 μL of HPLC water. For complete genome sequencing and sequencing of genes/regions of interest, primer sets were designed based on the genome of WN-NY99 (382-99). PCR products were then gel purified using the QIAquick kit (Qiagen) according to the manufacturer's protocol, and the resulting template was directly sequenced using the amplifying primers. Sequencing reactions were performed in the UTMB Biomolecular Resource Facility's DNA sequencing laboratory. Analysis and assembly of sequencing data was performed using the Vector NTI Suite software package (Informax; Bethesda, Md.). Nucleotide and deduced amino acid sequences of the complete genome of each isolate were aligned using the AlignX program in the Vector NTI Suite and then compared to a previously published sequence of WN-NY99 (GenBank accession no. AF196835; SEQ ID NO:1).

Viral RNA Extraction

Viral RNA was extracted directly from 140 μL of infected Vero or BHK cell culture supernatants using the QiaAMP viral RNA extraction kit according to protocol provided by manufacturer (Qiagen).

Reverse Transcription-Polymerase Chain Reaction (RT-PCR)

RT was performed in a 50 μL volume containing 5 μL of viral RNA, 1 μL of random hexamer primer, 10 μL of 5×RT buffer, 4 μL of 10 mM dNTPs, 0.4 μL of cloned RNAse inhibitor, 0.5 μL of Moloney murine leukemia virus (MMLV) reverse transcriptase, and 29.1 μL of HPLC purified water. RNA and primer were first heated at 72° C. for 10 minutes, followed by addition of reaction reagents for 10 minutes at 55° C. and 60 minutes at 45° C. RNA was stored at −80° C. until further use. PCR was performed in a 25 μL volume containing 2.0 μL cDNA template from RT, 1.0 μL forward primer, 1.0 μL reverse primer, 2.5 μL 10×PCR buffer, 0.5 μL 10 mM dNTPs, 0.5 μL of 1 U/μL Taq polymerase, and 17.5 μL of HPLC water. PCR conditions were as follows: 94° C. for 5 minutes—1x; 94° C. for 40 seconds; 54° C.* for 40 seconds—34x; 72° C. for 3 minutes; 72° C. for 7 minutes—1x (* Annealing temperatures varied depending on the melting temperatures of each primer used for the reaction.)

Each reaction was cooled to 4° C. and stored until PCR products were separated by gel electrophoresis in 2% agarose gels containing ethidium bromide (0.5 μL/ml in TAE buffer). Following visualization under UV light, PCR bands were cut out of gels and purified for sequencing/cloning using a Gel Extraction Kit according to the manufacturer's instructions (Qiagen).

Primers and Primer Design

Primers were designed based on the prototypical North American West Nile virus strain, NY99 (382-99), which was isolated from the brain of a dead flamingo in the Bronx Zoo in 1999. The complete genome of this strain was previosly sequenced by Lanciotti et al. (1999) and stored in GenBank (Accession no. AY196835). A set of eight primers with varying annealing temperatures were made to allow a consensus sequence to be constructed from overlapping amplicons aligned using the ContigExpress program in the Vector NTI software package (Informax, Version 8.0). RT-PCR primers were used as sequencing primers. A complete list of primers used is found in Table 12.

Following gel purification of PCR products, the resulting template was directly sequenced using the amplifying primers. Sequencing reactions were performed in the UTMB Biomolecular Resource Facility's DNA sequencing laboratory using the ABI PRISM Big Dye Terminator v3.0 cycle sequencing kits (Applied Biosystems, Foster City, Calif.) according to the manufacturer's protocol and analyzed on an ABI PRISM 3100 Genetic Analyzer (Applied Biosystems). Analysis and assembly of sequencing data were performed using the Vector NTI Suite software package (Informax).

Viral Plaque Morphology Assays and Titration

In order to establish the plaque morphology and titer of isolates collected in 2003 and 2004, plaque assays were carried out by infecting Vero cells in 6-well plates with WNV isolates at dilutions of $10^{-1}$ to $10^{-6}$. All plaque assays were run in parallel with WN-NY99 as a positive control and PBS as a negative control. Plaque morphology was measured by staining plaque assays with crystal violet followed by digital photography of plaques. Images were visualized in Microsoft Photoshop and diameters of plaques were measured from these images. The small plaque (sp) phenotype is described as a <1.0 mm difference in plaque diameter compared to the control WN-NY99 large plaque (lp) size >1.5 mm.

Temperature-Sensitivity Assays

In some embodiments, the temperature assays were as follows. Each isolate was also plaqued at 37.0° C., 39.0° C., and 41.0° C. for 72 hours to measure temperature-sensitivity (ts). The ts phenotype is described as a >2.0 $\log_{10}$ PFU reduction in titer determined by Vero cell plaque assay at either 39.5° C. or 41.0° C. when compared to permissive temperature 37.0° C.

In Vitro Replication Kinetic Assays

Growth curves were performed in triplicate by infecting Vero cells in 12-well plates with WNV isolates at an MOI of 0.1 PFU/cell. A low MOI was used in order to compare the multiplication kinetics of the variant viruses as a contributing factor to their attenuated phenotype rather than to compare their replication kinetics in a single step growth curve. Supernatants were then harvested at 0, 12, 24, 48, 72, and 96 hours post-infection. Vero cell plaque assays were used to determine mean virus titers at each time point.

West Nile Virus Infectious Clone Technology

The WNV NY99 virus-specific infectious cDNA clone was constructed in two plasmids, utilizing a derivative of plasmid pBRUC-139S (FIG. 8). Plasmid pWN-AB contained WNV nucleotides 1 to 2495, which were preceded by restriction sites SstI and MluI and the promoter for T7 polymerase. Plasmid pWN-CG contained WNV nucleotides 2495 to 11029 and an engineered 3'-terminal XbaI site for plasmid linearization just prior to transcription of genomic RNA. Nucleotide sequencing of the NY99 infectious clone-derived virus (NY99ic) and the parental NY99 stock from which it was derived identified seven nucleotide differences from the published NY99 sequence (GenBank accession no. AF196835), including two that encoded amino acid substitutions: C1428U, U1855C, C3880U (NS2A-118 His to Tyr), A4922G (NS3-104 Lys Arg), G7029U, U8811C, and A10851G. Full-genomic-length cDNA was prepared by cleaving the pWN-AB and pWN-CG plasmids at the natural NgoMIV-nucleotide 2495 site of WNV followed by ligating the two plasmids at this NgoMIV site. The in vitro-ligated DNA fragment containing the full-genome-length WNV cDNA was then purified by phenol/chloroform extraction and pelleted following an overnight ethanol precipitation. Following resuspension of the purified cDNA in TE buffer (pH 8.0), viral genomic RNA was transcribed by using the AmpliScribe T7 kit (Epicentre Technologies, Madison, Wis.). Transcription was carried out in the presence of m7-GpppA cap analog for 2 to 3 h at 37° C., and Vero cells were transfected with the transcribed RNA by electroporation in 0.2 cm electrode gap cuvettes (Biorad) at 1.5 kV, infinite Ohms, and 25 μF. Transfections were then transferred to T75 flasks with 8% MEM and observed daily for CPE. Rescued virus was harvested following the appearance of CPE or after 6 days post-infection.

Site-Directed Mutagenesis Using the Infectious Clone

In order to identify mutations to the WNV genome conferring phenotypic variation, site-directed mutagenesis of the infectious clone was used to substitute an amino acid that was identified by sequencing studies to differ between WN-NY99 and isolates displaying phenotypic variation. The inventors have identified several isolates with sp, ts, and attenuated phenotypes that also share amino acid substitutions when compared to WN-NY99. The substitution at NS4B (E249G), which is shared by three of the sp, ts, and attenuated 2003 WNV isolates, was the starting point at which site-directed mutations were made to the infectious clone. Mutations to the infectious clone were made using the QuikChange® XL Site-Directed Mutagenesis Kit (Stratagene). Briefly, this system can be used to make amino acid substitutions in the infectious clone by designing mutagenic primers which anneal to the region of interest of the WNV DNA inserted in the plasmid (e.g., nucleotide 7666 (NS4B E249G) of the WNV genome). The plasmid from the infectious clone containing the insert is denatured, allowing the mutagenic primers to anneal to the region of interest. The primers, which are each complementary to opposite strands of the plasmid insert, are extended during temperature cycling using PfuTurbo DNA polymerase. Incorporation of the mutagenic primers produces a mutated plasmid containing staggered nicks. When the temperature cycling is complete, the product is treated with Dpn I (an endonuclease which recognizes and digests methylated and hemimethylated DNA). Digestion with Dpn I digests the parental DNA template and selects for only synthesized DNA containing the mutation of interest. The synthesized DNA is then transformed into XL10-Gold ultracompetent cells to allow for nicked ends of the plasmid DNA to be repaired and to produce the mutated plasmid in larger quantities. Following generation of the desired plasmid, the reverse genetics system described above was used to generate an infectious WNV with the same mutation found in the sp, ts, and attenuated WNV isolates. Because it was possible that the observed phenotypes of 2003 WNV isolates were the result of an accumulation of mutations in the genome, it was necessary to continue to add mutations to the infectious clone in order to generate virus with measurable phenotypic variation. Mutations to the infectious clone (those unique to sp, ts, and attenuated isolates) were made as both single amino acid substitutions and as combinations of substitutions in order to account for the possibility of accumulated mutations resulting in specific viral phenotypes.

3'UTR Exchange Between Isolate Bird 1153 and WN-NY99 Infectious Clone

In order to completely exchange the 3'UTR of WNV strain Bird 1153 with the 3'UTR of the NY99 infectious clone, the 3'UTR of Bird 1153 was amplified by reverse transcriptase PCR (RT-PCR) using primers that introduced a 5' SalI site (3'UTR For: CAACTTTGGTCGACGACACAGTACTGT; SEQ ID NO:19) and a 3' XbaI site (3'UTR Rev: TCTAGAAGATCCTGTGTTCTCGACC; SEQ ID NO:20). This PCR product was then cloned into pGEM-T for substitution into the pWN-CG plasmid of the NY99 infectious clone. In order to do an exact exchange of the Bird 1153 3'UTR into the NY99 backbone, the Quikchange site-directed mutagenesis kit (Stratagene, La Jolla, Calif.) was used using the same primers to engineer those restriction sites at either end of the pWN-CG 3'UTR. None of these mutations resulted in changes to the nucleotide sequence as the restriction site motifs in the 3'UTR forward and reverse primers were contained outside of the WNV nucleotide sequence.

Infectious Clone Virus Rescue

In order to confirm that infectious virus was recovered following transfection, cell cultures were followed for a period ranging from 3-6 days post-transfection and observed for the presence of CPE. Upon indication of sufficient CPE, RT-PCR was performed on cell culture supernatants using primers that amplified the prM and E protein genes of the WNV genome. If the RT-PCR produced a positive result, the cell culture supernatants were harvested into at least 12×0.5 ml ampoules and stored at −80.0° C. for future use.

Genetic Characterization of Mutant Viruses

For those transfections that produced positive RT-PCR results, primers specific to regions containing the desired mutation(s) were used to amplify and sequence the PCR product to determine if the desired mutation was incorporated into the genome of the virus.

Phenotypic Characterization of Mutant Viruses

Upon successful viral rescue and and confirmation of site-directed mutations to the viral genome, a plaque morphology assay and ts assay were used to examine the phenotypic characteristic of each isolate. Viral multiplication kinetic studies were undertaken to measure the multiplication capacity of mutant viruses displaying sp and/or ts phenotypes. The ip $LD_{50}$ of each mutant virus was also measured using the same 3-4 week old female Swiss Webster mouse model as described above.

TABLE 12

Exemplary Primers used for Partial and Complete Genome Sequencing.

PrM-E

401+
AAA AGA AAA GAG GAG GAA AG          SEQ ID NO:21

1219−
GTT TGT CAT TGT GAG CTT CT          SEQ ID NO:22

1101+
GAT GAA TAT GGA GGC GGT CA          SEQ ID NO:23

1816−
CCG ACG TCA ACT TGA CAG TG          SEQ ID NO:24

1751+
TGC ATC AAG CTT TGG CTG GA          SEQ ID NO:25

2504−
TCT TGC CGG CTG ATG TCT AT          SEQ ID NO:26

5' UTR

1+
AGT AGT TCG CCT GTG TGA             SEQ ID NO:27

533−
CAG CAG CTG TTG GAA T               SEQ ID NO:28

Capsid

WN 132+
GAA AAC ATC AAG TAT GAG G           SEQ ID NO:29

WN 240−
GAG GTT CTT CAA ACT CCA T           SEQ ID NO:30

TABLE 12-continued

Exemplary Primers used for Partial and Complete Genome Sequencing.

Nonstructural protein genes

2418+
TGG AGG AGT TTT GCT CTT C           SEQ ID NO:31

3238−
TGT ACC CTG GTC TCC TGT             SEQ ID NO:32

3112+
GAA GTC AAA TCA TGC ACC             SEQ ID NO:33

4037−
CTG TAC ACA TCA AGG TTT AAG         SEQ ID NO:34

3849+
TTT CTT CCA AAT GGC TTA C           SEQ ID NO:35

4603−
CTC CTC TCT TTG TGT ACT GA          SEQ ID NO:36

4444+
GAT GAT GAT GGA AAT TTT C           SEQ ID NO:37

5417−
GGA GAC ATC AGC CTG              SEQ ID NO:38

5364+
TGA GAT CGT TGA TGT C                SEQ ID NO:39

6351−
CGT GAT GAC TTC AAC                  SEQ ID NO:40

6269+
CAT ACC ATG ACC GGA AAT              SEQ ID NO:41

7282−
CCA TGT AAG CAT AGT GGC              SEQ ID NO:42

7087+
ACG TCA GAC TAC ATC AAC ACT T        SEQ ID NO:43

8060−
ACT CCA CTC TTC ATG GTA A            SEQ ID NO:44

7999+
CAT GAA GAA CCA CAA CTG GT           SEQ ID NO:45

9043−
CCA TCA TGT TGT AGA TGC A            SEQ ID NO:46

8968+
TTT TGG GAG ATG GTG GAT GAG GAG      SEQ ID NO:47

9804−
AAC CTG CTG CCA GTC ATA CCA CCC C    SEQ ID NO:48

9730+
AAT GCT ATG TCA AAG GTC C            SEQ ID NO:49

3' UTR

10660−
CCT GGG GCA CTA TCG                  SEQ ID NO:50

10460+
GCC ACC GGA AGT TGA GTA              SEQ ID NO:51

10958−
CCT GTG TTC TAG CAC CAC              SEQ ID NO:52

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents and Patent Applications

U.S. Pat. No. 5,440,013
U.S. Pat. No. 5,618,914
U.S. Pat. No. 5,670,155
U.S. Pat. No. 5,446,128
U.S. Pat. No. 5,710,245
U.S. Pat. No. 5,840,833
U.S. Pat. No. 5,859,184
U.S. Pat. No. 5,929,237
U.S. Pat. No. 5,475,085
U.S. Pat. No. 5,672,681
U.S. Pat. No. 5,674,976
U.S. Pat. No. 4,554,101
U.S. Pat. No. 6,576,757
U.S. Patent Application Publication 2004/0052818
U.S. Patent Application Publication 2004/0037848
WO 03/061555

PUBLICATIONS

Bartelma, G., Padmanabhan, R., 2002. Expression, purification, and characterization of the RNA 5'-triphosphatase activity of dengue virus type 2 nonstructural protein 3. Virology 299, 122-132.

Beasley, D. C. W., Davis, C. T., Guzman, H., Vanlandingham, D. L., Travassos da Rosa, A. P. A., Parsons, R. E., Higgs, S., Tesh, R. B., Barrett, A. D. T., 2003. Limited evolution of West Nile virus has occurred during its southwesterly spread in the United States. Virology 309, 190-195.

Beasley, D. W. C., Davis, C. T., Whiteman, M., Granwehr, B., Kinney, R. M., Barrett, A. D. T., 2004. Molecular determinants of virulence of West Nile virus in North America. Calisher, C. H., DE Griffin, D. E. (Eds.), In: Emergence and control of zoonotic viral encephalitides. Arch. Virol. Supplement 18, pp. 35-41.

Beasley, D. W. C., Li, L., Suderman, M. T., Barrett, A. D. T., 2002. Mouse neuroinvasive phenotype of West Nile virus strains varies depending upon virus genotype. Virology 296, 17-23.

Beasley, D. W. C., Whiteman, M. C., Zhang, S.-L., Huang, C. Y.-H., Schneider, B. S., Smith, D. R., Higgs, S., Kinney, R. M., Barrett, A. D. T. Envelope protein glycosylation status influences mouse neuroinvasion phenotype of genetic lineage 1 West Nile virus strain. Submitted.

Blaney Jr., J. E., Manipon, G. G., Murphy, B. R., Whitehead, S. S., 2003. Temperature sensitive mutations in the genes encoding the NS1, NS2A, NS3, and NS5 nonstructural proteins of dengue virus type 4 restrict replication in the brains of mice. Arch. Virol. 148, 999-1006.

Blitvich, B. J., Femandez-Salas, I., Contreras-Cordero, J. F., Marlenee, N. L., Gonzalez-Rojas, J. I., Komar, N., Gubler, D. J., Calisher, C. H., Beaty, B. J., 2003. Serologic evidence of West Nile virus infection in horses, Coahuila State, Mexico. Emerg. Infect. Dis. 9, 853-856.

Bunning, M. L., Bowen, R. A., Cropp, C. B., Sullivan, K. G., Davis, B. S., Komar, N., Godsey, M. S., Baker, D., Hettler, D. L., Holmes, D. A., Biggerstaff, B. J., Mitchell, C. J., 2002. Experimental infection of horses with West Nile virus. Emerg. Infect. Dis. 8, 380-6.

CDC., 2002. Provisional surveillance summary of the West Nile virus epidemic-United States, January-November 2002. MMWR. 51, 1129-1133.

Charrel, R. N., Brault, A. C., Gallian, P., Lemasson, J.-J., Burgue, B., Murri, S., Pastorino, B., Zeller, H., de Chesse, R., de Micco, P., and de Lamballerie, X., 2003. Evolutionary relationship between Old World West Nile virus strains: evidence for viral gene flow between Africa, the Middle East, and Europe. Virology 315, 381-388.

Davis, C. T., Beasley, D. C. W., Guzman, H., Raj, P., D'Anton, M., Novak, R. J., Unasch, T. R., Tesh, R. B., Barrett, A. D. T., 2003. Genetic variation among temporally and geographically distinct West Nile virus isolates collected in the Unites States, 2001 and 2002. Emerg. Infect. Dis. 9, 1423-1429.

Dokland, T., Walsh, M., Mackenzie, J. M., Khromykh, A. A., Ee, K.-H., Wang, S., 2004. West Nile Virus core protein: tetramer structure and ribbon formation. Structure 12, 1157-1163.

Dunster, L. M., Gibson, C. A., Stephenson, J. R., Minor, P. D., Barrett, A. D. T., 1990. Attenuation of virulence of *flaviviurses* following passage in HeLa cells. J. Gen. Vir. 71, 601-607.

Dupuis 2nd, A. P., Marra P, Kramer L D., 2003. Serological evidence of West Nile virus transmission, Jamaica, West Indies. Emerging Infectious Diseases 9: 860-863.

Eastman, P. S., Blair, C. D., 1985. Temperature-sensitive mutants of Japanese encephalitis virus. J. Virol. 55, 611-616.

Egloff, M.-P., Benarroch, D., Selisko, B., Romette, J.-L., and Canard, B., 2002. An RNA cap (nucleoside-2'-O-)-methyltransferase in the *Flavivirus* RNA polymerase NS5: crystal structure and functional characterization. The EMBO J., 21, 2757-2768.

Estrada-Franco, J. G., Navarro-Lopez, R., Beasley, D. W., Coffey, L., Carrara, A. S., Travassos da Rosa, A., Clements, T., Wang, E., Ludwig, G. V., Cortes, A. C., Ramirez, P. P., Tesh, R. B., Barrett, A. D., Weaver, S. C., 2003. West Nile virus in Mexico: evidence of widespread circulation since July 2002. Emerg. Infect. Dis. 9, 1604-1607.

Hanley, K. A., Lee, J. J., Blaney Jr., J. E., Murphy, B. R., Whitehead, S. S., 2002. Paired charge-to-alanine mutagenesis of dengue virus type 4 NS5 generates mutants with temperature-sensitive, host range, and mouse attenuation phenotypes. J. Virol. 76, 525-531.

Hanley, K. A., Manlucu, L. R., Gilmore, L. E., Blaney, J. E., Hanson, C. T., Murphy, B. R., Whitehead, S. S., 2003. A trade-off in replication in mosquito versus mammalian systems conferred by a point mutation in the NS4B protein of dengue virus type 4. Virology 312, 222-232.

Hollingshead Jr., P. G., Brawner, T. A., Fleming, T. P., 1983. St. Louis encephalitis virus temperature-sensitive mutants. I. Induction, isolation and preliminary characterization. Arch. Virol. 75, 171-179.

Johannesson et al., 1999, "Bicyclic tripeptide mimetics with reverse turn inducing properties." J. Med. Chem. 42:601-608.

Johnson, A. J., D. A. Martin, Karabatsos, N., and Roehrig, J. T., 2000. Detection of antarboviral immunoglobulin G by using a monoclonal antibody-based capture enzyme-linked immunosorbent assay. J. Clin. Microbiol. 38, 1827-1831.

Johnson et al., 1993

Jones, C. T., Ma, L., Burgner, J. W., Groesch, T. D., Post, C. B., Kuhn, R. J., 2003. *Flavivirus* capsid is a dimeric alpha-helical protein. J. Virol. 77, 7143-7149.

Komar, N., Langevin, S., Hinten, S., Nemeth, N., Edwards, E., Hettler, D., Davis, B., Bowen, R., Bunning, M., 2003. Experimental infection of North American birds with the New York 1999 strain of West Nile virus. Emerg. Infect. Dis. 9, 311-22.

Komar, O., Robbins, M. B., Klenk, K., Blitvich, B. J., Marlenee, N. L., Burkhalter, K. L., Gubler, D. J., Gonzalvez, G., Pena, C. J., Peterson, A. T., Komar, N., 2003. West Nile virus transmission in resident birds, Dominican Republic. Emerg. Infect. Dis. 9, 1299-1302.

Lai, C. J., and Monath, T. P., 2004. Chimeric *Flaviviruses*: novel vaccines against dengue fever, tick-borne encephalitis, and Japanese encephalitis. Adv Virus Res., 61:469-509.

Lanciotti, R. S. and Kerst, A. J., 2001. Nucleic acid sequence-based amplification assays for rapid detection of West Nile and St. Louis encephalitis viruses. J. Clin. Microbiol., 39(12), 4506-4513.

Lanciotti, R. S., Roehrig, J. T., et al., 1999. Origin of the West Nile virus responsible for the outbreak of encephalitis in the northeastern U.S. Science, 286, 2333-2337.

Lanciotti, R. S., Ebel, G. D., Deubel, V., Kerst, A. J., Murri, S., Meyer, R., Bowen, M., McKinney, N., Morrill, W. E., Crabtree, M. B., Kramer, L. D., Roehrig, J. T., 2002. Complete genome sequences and phylogenetic analysis of West Nile virus strains isolated from the United States, Europe, and the Middle East. Virology 298, 96-105.

Lanciotti, R. S., Roehrig, J. T., Deubel, V., Smith, J., Parker, M., Steele, K., Volpe, K. E., Crabtree, M. B., Scherret, J. H., Hall, R. A., MacKenzie, J. S., Cropp, C. B., Panigrahy, B., Ostlund, E., Schmitt, B., Malkinson, M., Banet, C., Weissman, J., Komar, N., Savage, H. M., Stone, W., McNamara, T., Gubler, D. J., 1999. Origin of the West Nile virus responsible for an outbreak of encephalitis in the northeastern U.S. Science. 286, 2333-2337.

Ledger, T. N., Sil, B. K., Dunster, L. M., Stephenson, J. R., Minor, P. D., Barrett, A. D. T., 1992. Yellow fever 17DD vaccine virus is temperature sensitive when grown in mosquito C6-36 cells. Vaccine 10, 652-654.

Lillibridge, K. M., Parsons, R., Randle, Y., Travassos da Rosa, A. P. A., Guzman, H., Siirin, M., Wuithiranyagool, T., Hailey, C., Beasley, D. W., Higgs, S., Pascual, R., Meyer, T., Barrett, A. D. T., Tesh, R. B., 2004. The 2002 introduction of West Nile virus into Harris County, Tex., an area historically endemic for St. Louis encephalitis. Am. J. Trop. Med. Hyg. 70, 676-681.

Liu, W. J., Chen, H. B., Khromykh, A. A., 2003. Molecular and functional analyses of Kunjin virus infectious cDNA clones demonstrate the essential roles for NS2A in virus assembly and for a nonconservative residue in NS3 in RNA replication. J. Virol. 77(14): 7804-7813.

Ma, L., Jones, C. T., Groesch, T. D., Kuhn, R. J., Post, C. B., 2004. Solution structure of dengue virus capsid protein reveals another fold. Proc. Natl. Acad. Sci. USA, 101, 3414-3419.

Martin, D. A., Muth, D. A., Brown, T., Johnson, A. J., Karabatsos, N., and Roehrig, J. T., 2000. Standardization of immunoglobulin M capture enzyme-linked immunosorbent assays for routine diagnosis of arboviral infections. J. Clin. Microbiol. 38, 1823-1826.

McMinn, P. C., 1997. The molecular basis of virulence of the encephalitogenic *flaviviruses*. J. Gen. Virol. 78, 2711-2722.

Modis, Y., Ogata, S., Clements, D., Harrison, S. C., 2003. A ligand-binding pocket in the dengue virus envelope glycoprotein. Proc. Natl. Acad. Sci. USA, 100, 6986-6991.

Monath, T. P., Heinz, F. X., 1996. *Flavivirus* es . In: Fields, B. N., Knipe, D. M., Howley, P. M. (Eds), Fields Virology. Lippincott-Raven, Philadelphia, pp. 961-1034.

Murgue, B., Zeller, H., Duebel, V., 2002. The ecology and epidemiology of West Nile virus in Africa, Europe, and Asia. Curr. Top. Microbiol. Immunol. 267, 195-221.

Murthy, H. M. K., Clum, S., Padmanabhan, R., 1999a. Dengue Virus NS3 Serine Protease. J. Biol. Chem., 274, 5573-5580.

Murthy, H. M. K., Judge, K., DeLucas, L., Clum, S., Padmanabhan, R., 1999b. Crystallization, characterization and measurement of MAD data on crystals of dengue virus NS3 serine protease complexed with mung-bean Bowman-Birk inhibitor. Acta Cryst., D55, 1370-1372.

Murthy, H. M. K., Judge, K., DeLucas, L., Padmanabhan, R., 2000. Crystal Structure of Dengue Virus NS3 Protease in Complex with a Bowman-Birk Inhibitor: Implications for Flaviviral Polyprotein Processing and Drug Design. J. Mol. Biol., 301, 759-767.

Nall T A, Chappell K J, Stoermer M J, Fang N X, Tyndall J D, Young P R, Fairlie D P, Enzymatic Characterisation and Homology Model Of A Catalytically Active Recombinant West Nile Virus NS3 Protease. J Biol. Chem. 2004 Aug. 18 [Epub ahead of print].

Puri, B., Nelson, W. M., Henchal, E. A., Hoke, C. H., Eckels, K. H., Dubois, D. R., Porter, K. R., Hayes, C. G., 1997. Molecular analysis of dengue virus attenuation after serial passage in primary dog kidney cells. J. Gen. Virol. 78, 2287-2291.

Quirin, R., Salas, M., Zientara, S., Zeller, H., Labie, J., Murri, S., Lefrancois, T., Petitclerc, M., Martinez, D., 2004. West Nile virus, Guadeloupe. Emerg Infect Dis. 10: 706-708.

Rey, F. A., Heinz, F. X., Mandl, C., Kunz, C., Harrison, S. C., 1995. The envelope glycoprotein from tick-borne encephalitis virus at 2 Å resolution, Nature, 375, 291-298.

Ryan, M. D., Monaghan, S., and Flint, M., 1998. Virus-encoded proteinases of the Flaviviridae. J. Gen. Virol. 79, 947-959.

Solomon, T., Vaughn, D. W., 2002. Pathogenesis and clinical features of Japanese encephalitis and West Nile virus infections. Curr. Top. Micro. Immun. 267, 171-194.

Vita et al., 1998, Novel miniproteins engineered by the transfer of active sites to small natural scaffolds. Biopolymers 47:93-100.

Volk et al., 2004, Solution structure and antibody binding studies of the envelope protein domain III from the New York strain of West Nile virus. J Biol. Chem., in press.

Wallner, G., Mandl, C. W., Ecker, M., Holzmann, H., Stiasny, K., Kunz, C., Heinz, F. X., 1996. Characterization and complete genome sequences of high- and low-virulence variants of tick-borne encephalitis virus. J. Gen. Virol. 77, 1035-42.

Weisshoff et al., 1999, "Mimicry of beta II'-turns of proteins in cyclic pentapeptides with one and without D-amino acids." Eur. J. Biochem. 259:776-788.

Wu J, Bera A K, Kuhn R J, Smith J L., Structure of the *Flavivirus* helicase: implications for catalytic activity, protein interactions, and proteolytic processing, J. Virol. 2005 August;79(16):10268-77.

Xiao, S. Y., Guzman, H., Zhang, H., Travassos da Rosa, A. P., Tesh, R. B., 2001. West Nile virus infection in the golden hamster (Mesocricetus auratus): a model for West Nile encephalitis. Emerg Infect Dis. 7, 714-21.

Xu T, Sampath A, Chao A, Wen D, Nanao M, Chene P, Vasudevan S G, Lescar J., Structure of the Dengue virus helicase/nucleoside triphosphatase catalytic domain at a resolution of 2.4 A, J. Virol. 2005 August;79(16):10278-88.

Yu, S., Wuu, A., Basu, R., Holbrook, M. R., Barrett, A. D. T., Lee, J. C., 2004, Solution structure and structural dynamics of envelope protein domain III of mosquito- and tick-borne *flaviviruses*. Biochemistry 43, 9168-9176.

Although the present invention and its advantages have been described in detail, it should be understood that various changes, substitutions and alterations can be made herein

What is claimed is:

1. An immunogenic virus that comprises at least part of an isolated North American West Nile virus genome, said genome having at least two alterations therein and comprising one or more coding regions, non-coding regions, or both, wherein said at least two alterations produce one or more phenotypic variations to the West Nile virus and wherein at least one of the alterations is not in a coding region for a structural protein and wherein at least one alteration is in a coding region for NS4B or is in the 3' UTR.

2. The virus of claim 1, wherein the virus comprises all of the isolated North American West Nile virus genome.

3. The virus of claim 1, wherein the virus comprises part of the isolated North American West Nile virus genome.

4. The virus of claim 1, wherein at least one of the alterations is selected from the group consisting of: NS4B E249, 3'UTR A10596, 3' UTR C10774, and 3' UTR A10799.

5. The virus of claim 1, wherein at least one of the alterations is selected from the group consisting of: NS4B E249, 3'UTR A10596G, 3' UTR C10774U, and 3' UTR A10799G.

6. The virus of claim 1, wherein at least one of the alterations is NS4B E249G.

7. The virus of claim 1, wherein at least one of the alterations is 3'UTR A10596G.

8. The virus of claim 1, wherein at least one of the alterations is 3' UTR C10774U.

9. The virus of claim 1, wherein at least one of the alterations is 3' UTR A10799G.

10. The virus of claim 1, wherein at least one of the alterations is in at least part of a β-sheet, an α-helix, a β-turn, a β-barrel, a β-hairpin, or a helix-turn-helix.

11. The virus of claim 1, wherein the phenotypic variation comprises attenuation compared to the multiplication of a reference strain, a small plaque phenotype, a temperature-sensitive phenotype, reduced replication in cell culture, attenuation of neuroinvasiveness, attenuation of neurovirulence, reduced replication in vertebrates, reduced replication in arthropods, or a combination thereof.

12. The virus of claim 1, wherein the phenotypic variation comprises attenuation compared to the multiplication of a corresponding reference strain.

13. The virus of claim 12, wherein said reference strain is NY99.

14. The virus of claim 1, wherein one or more of the alterations is comprises one or more from the following group: NS4B V173I and NS4B T240A.

15. The virus of claim 1, wherein one or more of the alterations comprises one or more from the following group: NS4B S11N, NS4B I13V, NS4B V23A, NS4B T165A, NS4B I245M, NS4B E249G, and NS4B E249D.

16. A composition comprising the virus of claim 1, and a suitable excipient.

17. A composition comprising the virus of claim 1, and an adjuvant.

18. A method of manufacturing an immunogenic composition, the method comprising providing a virus of claim 1 and mixing said virus with a suitable excipient.

* * * * *